United States Patent
Seifert et al.

(10) Patent No.: US 9,943,297 B2
(45) Date of Patent: Apr. 17, 2018

(54) SOFT TISSUE REPAIR SYSTEM

(75) Inventors: Jody L. Seifert, Birdsboro, PA (US); David C. Paul, Phoenixville, PA (US); Sean Suh, Bensalem, PA (US); Colm McLaughlin, Philadelphia, PA (US); Marcin Niemiec, Bridgeport, PA (US); Aditya Ingalhalikar, Bryn Mawr, PA (US); Daniel Davenport, Collegeville, PA (US); Jamie Carroll, Drexel Hill, PA (US); Chad Glerum, Pennsburg, PA (US); Edward Dwyer, Pittsgrove, NJ (US); Noah Hansell, King of Prussia, PA (US); Mark Weiman, Coatesville, PA (US); Douglas Cahill, Lititz, PA (US); Adam Friedrich, Cinnaminson, NJ (US); Michelle Kofron, Kunkletown, PA (US); Vipin Kunjachan, Audubon, PA (US); Ed Reilley, Boyertown, PA (US); Damien O'Halloran, Conshohocken, PA (US); William S Rhoda, Media, PA (US); Brian Malm, Arlington, VA (US)

(73) Assignee: Globus Medical, Inc., Audubon, PA (US)

( * ) Notice: Subject to any disclaimer, the term of this patent is extended or adjusted under 35 U.S.C. 154(b) by 936 days.

(21) Appl. No.: 13/105,153

(22) Filed: May 11, 2011

(65) Prior Publication Data

US 2012/0010653 A1  Jan. 12, 2012

Related U.S. Application Data

(60) Provisional application No. 61/345,485, filed on May 17, 2010.

(51) Int. Cl.
*A61B 17/00* (2006.01)
*A61F 2/44* (2006.01)
(Continued)

(52) U.S. Cl.
CPC .......... *A61B 17/0057* (2013.01); *A61F 2/441* (2013.01); *A61F 2/4611* (2013.01);
(Continued)

(58) Field of Classification Search
CPC ........ A61B 17/12181; A61B 17/12186; A61B 17/12195; A61B 17/0057;
(Continued)

(56) References Cited

U.S. PATENT DOCUMENTS

2002/0147497 A1* 10/2002 Belef et al. ................. 623/17.12
2005/0288706 A1* 12/2005 Widomski et al. ........... 606/213
(Continued)

*Primary Examiner* — Alexander Orkin

(57) ABSTRACT

A soft tissue repair system is provided for covering or filling openings in the annulus of an intervertebral disc. The soft tissue repair system uses a single plug or a combination of a first plug and a second plug. The second plug is a flowable plug such as an adhesive material or a material that hardens to a flexible plug material. Each plug is configured to close the opening in the annulus and can be positioned within the opening, over the opening at the exterior surface or over the opening at the interior surface. The plug can also be combined with a clamping mechanism that engages the annulus to secure the plug in the opening.

12 Claims, 51 Drawing Sheets

(51) Int. Cl.
  *A61F 2/46* (2006.01)
  *A61B 17/06* (2006.01)
  *A61F 2/30* (2006.01)

(52) U.S. Cl.
  CPC . *A61B 17/06166* (2013.01); *A61B 2017/0065* (2013.01); *A61B 2017/00579* (2013.01); *A61B 2017/00588* (2013.01); *A61B 2017/00606* (2013.01); *A61B 2017/00654* (2013.01); *A61B 2017/00668* (2013.01); *A61B 2017/00986* (2013.01); *A61F 2002/3052* (2013.01); *A61F 2002/30062* (2013.01); *A61F 2002/30291* (2013.01); *A61F 2002/30299* (2013.01); *A61F 2002/30405* (2013.01); *A61F 2002/30471* (2013.01); *A61F 2002/30507* (2013.01); *A61F 2002/30561* (2013.01); *A61F 2002/30576* (2013.01); *A61F 2002/30578* (2013.01); *A61F 2002/30579* (2013.01); *A61F 2002/30583* (2013.01); *A61F 2002/30584* (2013.01); *A61F 2002/30841* (2013.01); *A61F 2002/4415* (2013.01); *A61F 2002/4435* (2013.01); *A61F 2002/4495* (2013.01)

(58) Field of Classification Search
  CPC ............. A61B 2017/0065; A61F 2/441; A61F 2002/30299; A61F 2002/30583; A61F 2002/4435; A61F 2002/20584
  USPC .................... 606/213, 214; 623/17.11, 17.12
  See application file for complete search history.

(56) References Cited

U.S. PATENT DOCUMENTS

| | | | |
|---|---|---|---|
| 2006/0247784 A1* | 11/2006 | Kim | 623/17.16 |
| 2006/0293749 A1* | 12/2006 | Hudgins et al. | 623/17.11 |
| 2007/0156245 A1* | 7/2007 | Cauthen et al. | 623/17.16 |
| 2008/0172126 A1* | 7/2008 | Reynolds | 623/17.16 |
| 2011/0046670 A1* | 2/2011 | Lehmann et al. | 606/232 |

* cited by examiner

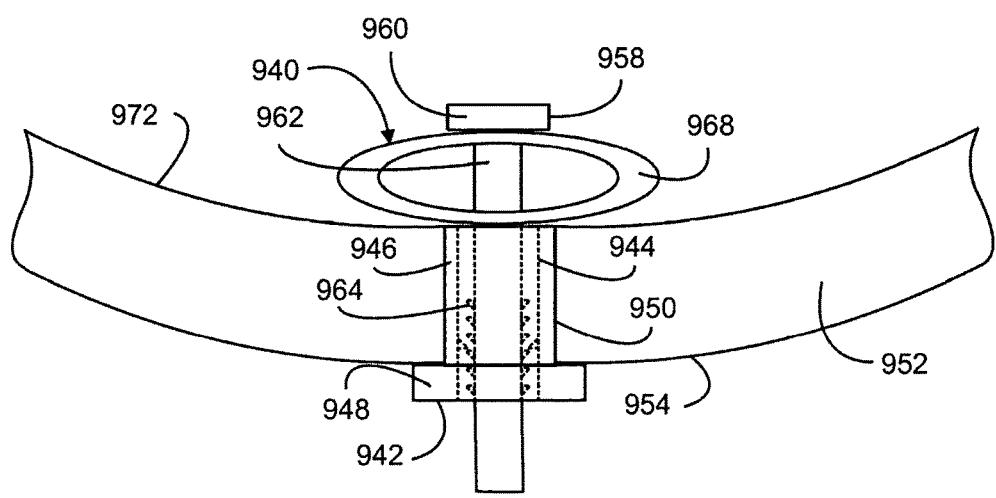
FIG. 56
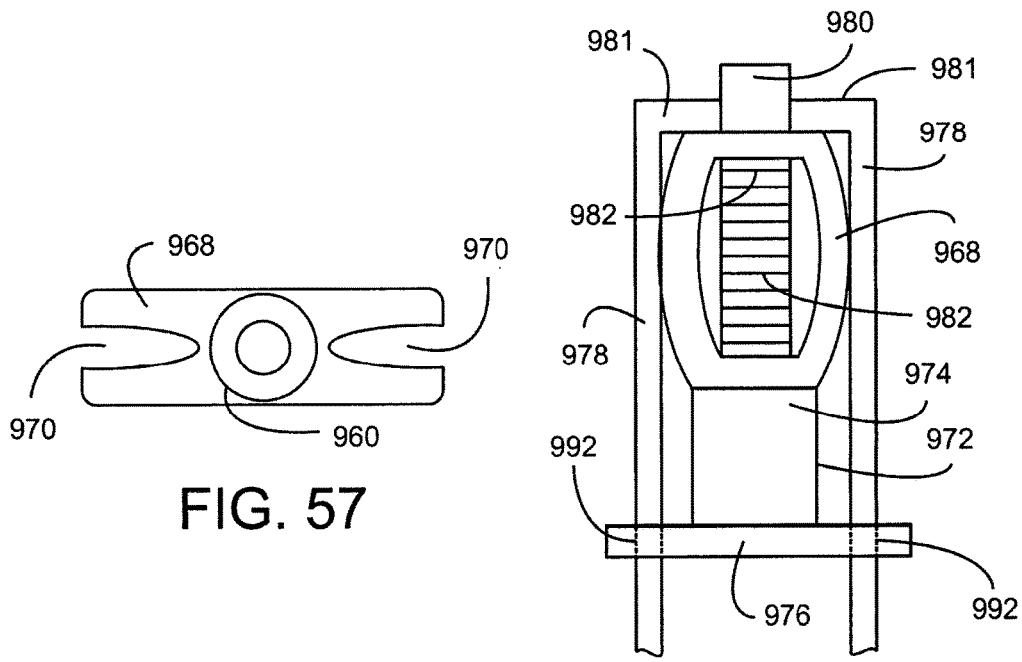
FIG. 57
FIG. 58

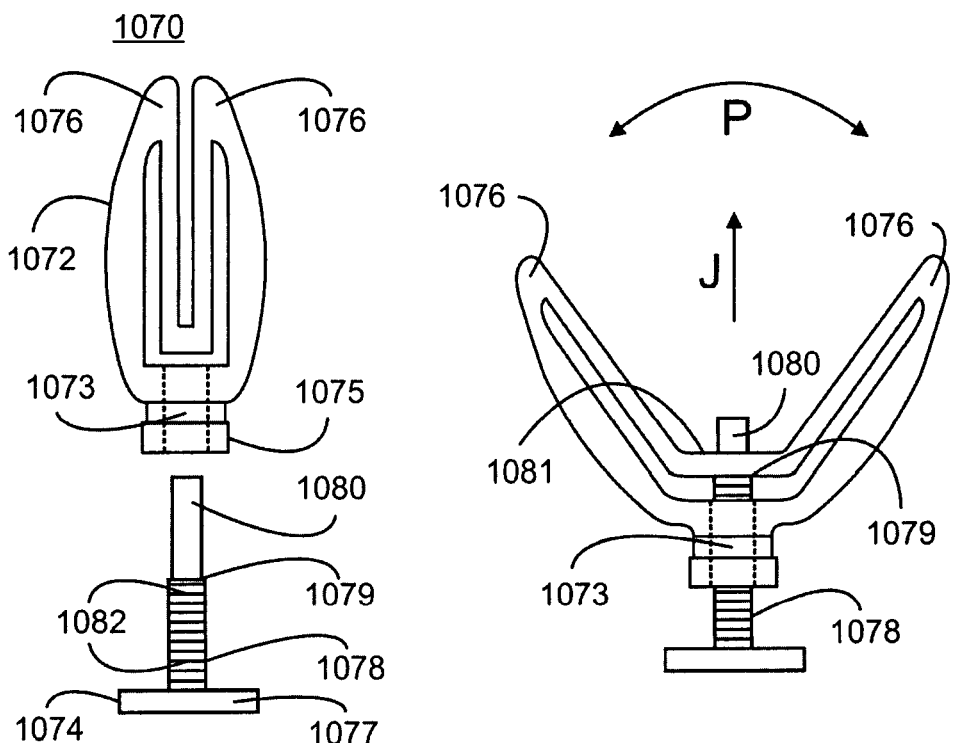
FIG. 66
FIG. 67
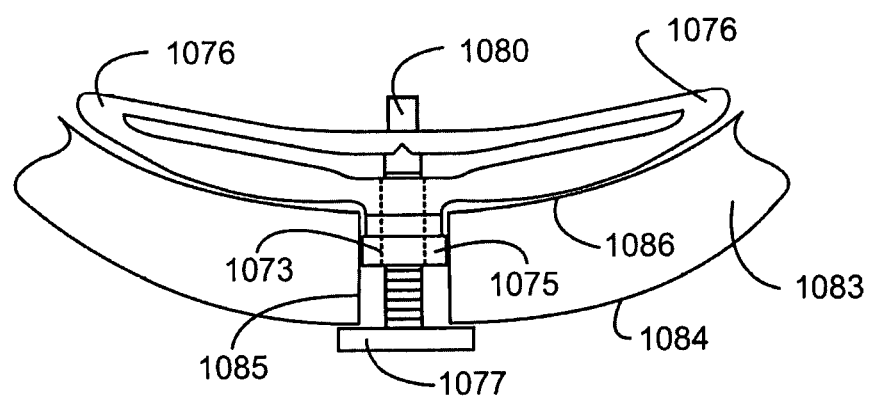
FIG. 68

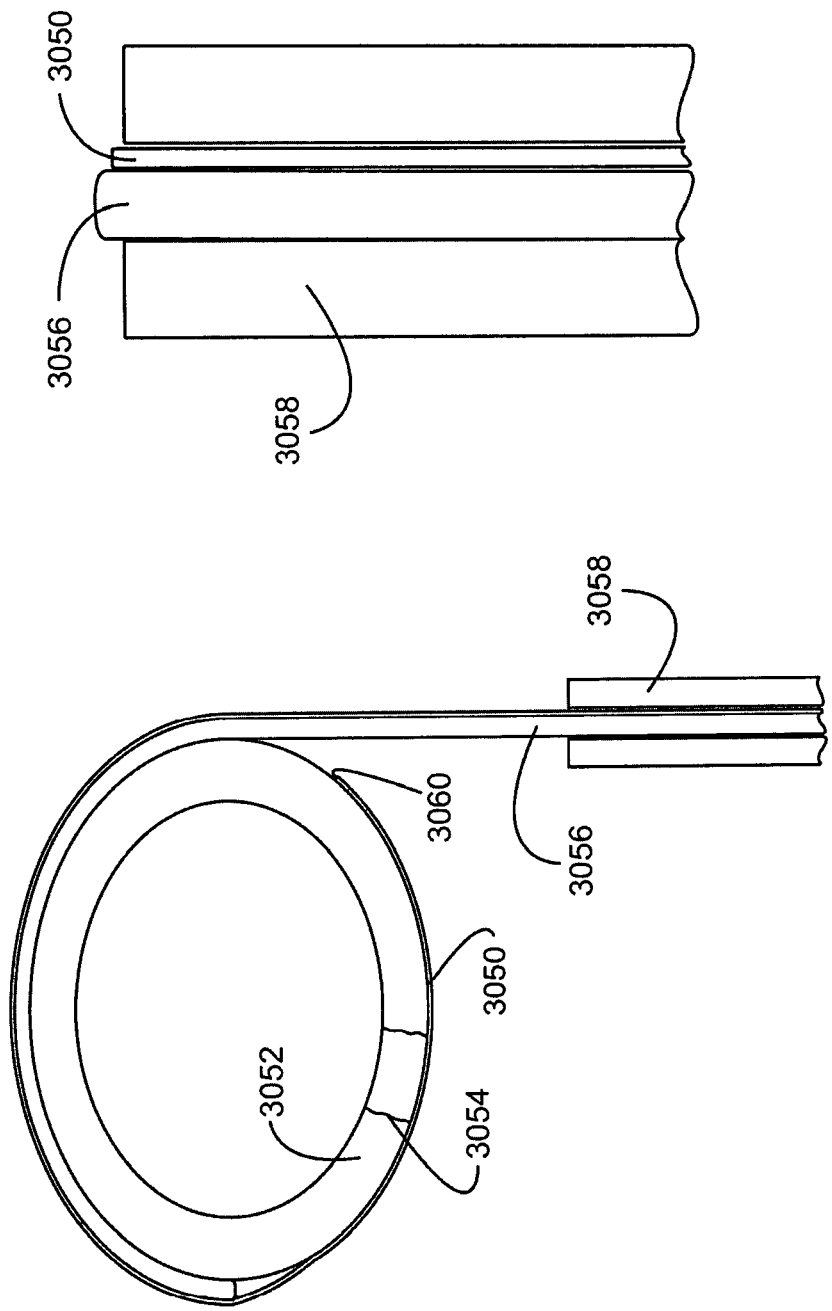

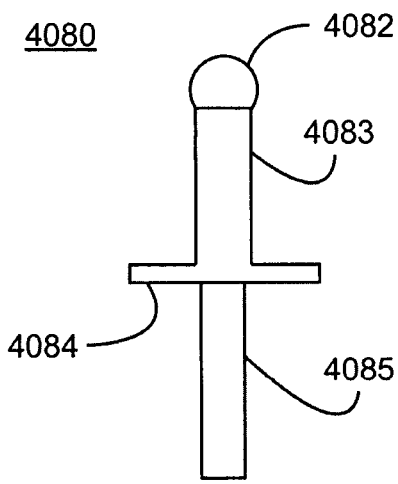
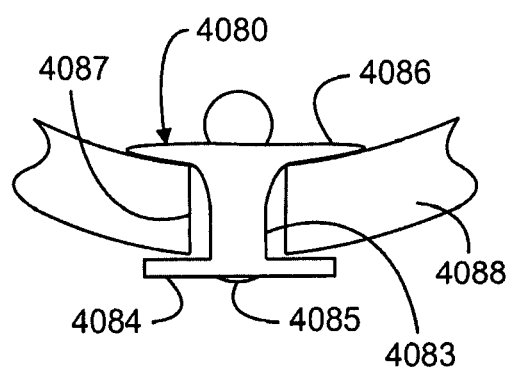
FIG. 103  FIG. 104
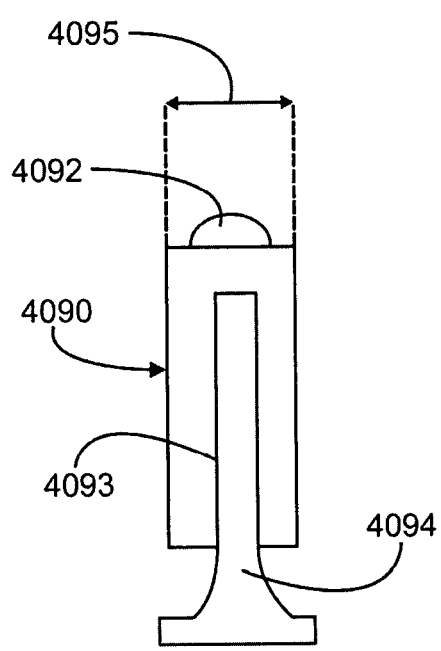
FIG. 105

SOFT TISSUE REPAIR SYSTEM

CROSS-REFERENCE TO RELATED APPLICATIONS

This application claims priority to U.S. Provisional Application Ser. No. 61/345,485 filed on May 17, 2010, which is incorporation herein in its entirety be reference.

FIELD OF THE INVENTION

The present invention relates to soft tissue repair of the annulus of intervertebral discs.

BACKGROUND OF THE INVENTION

The annulus of intervertebral discs is a soft fibrous tissue. This soft tissue can develop defects or tears, and a portion of the nucleus pulposus can be squeezed through the tear causing pain and discomfort. In addition, the annulus is opened to provide access to the nucleus pulposus during discectomy procedures. The annulus remains open at the completion of the discectomy, leading to the possibility of reherniation. A need to repair the tears or to close the openings in the annulus following surgical procedures exists.

Methods have been developed to repair tears and to close openings in the annulus. These methods include using sutures to close the tear, which can fail over time, and using plugs that are inserted into the tear. These plugs, however, are typically inserted from the exterior of the annulus and require difficult positioning or enlarging of the tear to accommodate insertion of the plug. Some plugs only cover the external side of the annulus tear. Therefore, improved systems and methods for annulus repair are desired.

SUMMARY OF THE INVENTION

Exemplary embodiments of the present invention are directed to methods and systems for repairing annulus openings, i.e., tears, ruptures and holes in an annulus. In accordance with one exemplary embodiment, the present invention is directed to a soft tissue repair system that includes a first plug in combination with a second plug. Both plugs are configured to close an opening that passes through an annulus from an exterior surface of the annulus to an interior surface of the annulus and can be positioned in within the opening, over the opening at the exterior surface over the opening at the interior surface, or any combination thereof. The second plug is separate from the first plug and is constructed of a flowable plug material.

In one embodiment, this flowable plug material is an adhesive material. In addition, the flowable plug material can set or harden to form a flexible plug material. In one embodiment, the first plug is a flexible plug configured to conform to the contours of the annulus and the opening in the annulus. The first plug can also include a clamping mechanism to secure the first plug to the annulus. For example, the clamping mechanism can engage the interior surface and the exterior surface of the annulus adjacent the opening.

The locations of the first and second plugs with regard to the annulus opening can be varied. For example, the first plug can be disposed within the opening, and the second plug can act as a filler, being disposed between portions of the first plug and walls within the opening. Alternatively, the first plug can be disposed within the opening, and the second plug used to cover opening at the interior surface or exterior surface of the annulus. In one embodiment, the first plug is a cover-type plug configured to cover the opening at the interior surface or exterior surface of the annulus. In this embodiment, the second plug can be disposed within the opening.

In one embodiment, the first plug is arranged as an inflatable balloon having an inflated position configured to fill the opening in the annulus. The second plug is disposed within the first plug when the first plug is in the inflated position. In another embodiment, the first plug is a collapsible cage having a pair of opposing ends and a plurality of arms extending between the opposing ends and fixedly secured thereto. This collapsible cage is configured to collapse and to expand to fill the opening in the annulus. The second plug is disposed within the opposing ends and the plurality of arms of the collapsible case and emerges from the collapsible cage as it is collapsed. In one embodiment, each arm includes a spike disposed along its length and extending outward from the collapsible cage. Each spike penetrates the annulus, for example within the annulus opening, when the collapsible cage is collapsed.

In one embodiment, the first plug includes a head portion configured to be larger than the opening at the exterior surface of the annulus and a tapered body attached to and extending from the head. The tapered body narrows as it extends from the head. The first plug also includes a central cylindrical shaft extending completely through the head and the tapered body. The second plug is disposed in the central cylindrical shaft. In this embodiment, the first plug further also includes a push rod that extends through the central cylindrical shaft. The push rod is configured to expel the second plug from the cylindrical shaft. In one embodiment, the first plug also includes a plurality of barbs attached to and extending from the head portion.

Exemplary embodiments of the present invention are also direction to a soft tissue repair system configured as a plug having a recess and a hole in the recess. A screw extends through the hole in the cap and rotatable in the hole without rotating the cap. The screw includes a head located in the recess and threads on a distal end opposite the head. The plug also includes spreading bar having two ends and a threaded opening disposed between the two ends. The screw threads are engaged in the threaded opening. A pair of opposing arms is provided such that each arm extends from the cap and contacts an end of the spreading bar. The plug is configured such that rotation of the screw draws the spreading bar toward the cap and pushes the arms apart. In one embodiment, each arm includes a plurality of barbs extending from that arm.

Exemplary embodiments of the present invention are also directed to a soft tissue repair system containing a plug having an integrated anchoring mechanism. The plug includes a plurality of independent and separate segmented arms arranged around a common axis to form a cylindrical shaped plug having an enlarged head. Proximal ends of the segmented arms yield the enlarged head having an overall diameter that is larger than an opening in an annulus that is to be repaired. Each segmented arm includes a plurality of segments configured such that adjacent segments can pivot with respect to each other about a pivot pin common to the adjacent segment. The plug also includes a threaded set screw running through a center of the cylindrical shape that is created by the plurality of segmented arms. The threaded set screw is concentric with the common axis of the segmented arms and engages at least one segment in each segmented arm. The plug is configured such that rotation of the threaded set screw about the common axis draws each engaged segment along the common axis, pivoting adjacent segments with respect to each other and expanding an end of the plug opposite the enlarged head. In one embodiment, the plurality of segments in each segmented arm include a primary segment having a proximal end that is enlarged and includes a hook portion, a first intermediate segment pivotally attached to one end of the primary segment opposite the proximal end, a second intermediate segment pivotally attached to the first intermediate segment and an end segment pivotally attached to the second intermediate segment. The first intermediate segment is disposed between the primary segment and the second intermediate segment, and the second intermediate segment is disposed between the first intermediate segment and the end segment.

BRIEF DESCRIPTION OF THE DRAWINGS

FIG. 56 is a schematic representation of the plug with clamping mechanism of FIG. 55 disposed in the annulus opening in a clamped position;

FIG. 57 is a representation of the plug with clamping mechanism in a clamped position as viewed from an interior of the annulus;

FIG. 58 is a representation of another embodiment of a plug with a clamping mechanism in accordance with the present invention in an initial position for insertion in an annulus opening;

FIG. 66 is a representation of another embodiment of a plug and anchoring mechanism in accordance with the present invention;

FIG. 67 is a representation of the plug and anchoring mechanism of FIG. 66 is a partially expanded position;

FIG. 68 is a representation of the plug and anchoring mechanism of FIG. 66 in a fully expanded position and disposed in an annulus opening;

FIG. 89 is a representation of another embodiment of a cover-type plug deployed over the exterior surface of an annulus;

FIG. 90 is a representation of the cover-type plug of FIG. 89 retracted into a cannula;

FIG. 103 is a representation of another embodiment of a plug with clamping mechanism in accordance with the present invention;

FIG. 104 is a representation of the plug and clamping mechanism of FIG. 103 disposed in an annulus opening with the clamping mechanism engaged;

FIG. 105 is a representation of another embodiment of a plug with clamping mechanism in accordance with the present invention;

DETAILED DESCRIPTION

Exemplary embodiments of products, e.g., implants and plugs, and methods in accordance with the present invention repair and fill openings in the annulus of intervertebral discs that range from small fissures to larger openings of approximately 6 mm. In addition to blocking or filling the opening, implants such as plugs that are inserted into the opening or cover-type plugs that are placed over the opening are secure and can withstand internal disc pressures and accommodate the range of motion of the disc. The plugs can be inserted using minimally invasive surgical techniques. Suitable materials for the implants provide a desired amount of cushioning between adjacent vertebrae, sufficient flexibility and sufficient strength to close the opening and withstand disc movement and pressure. These materials include, but are not limited to, collagen, polymers such as polycarbonate urethane (PCU), elastomers and metals such as titanium. In one embodiment, the materials are resorbable materials.

Soft tissue repair systems in accordance with the present invention utilize a variety of structures and techniques to close openings in the annulus. These structures include, but are not limited to, plugs that are inserted through and fixed within the opening, clamps or cover-type plugs that cover the opening and are secured to the annulus or the opening, combinations of plugs and cover-type plugs and other devices.

Figure 1:
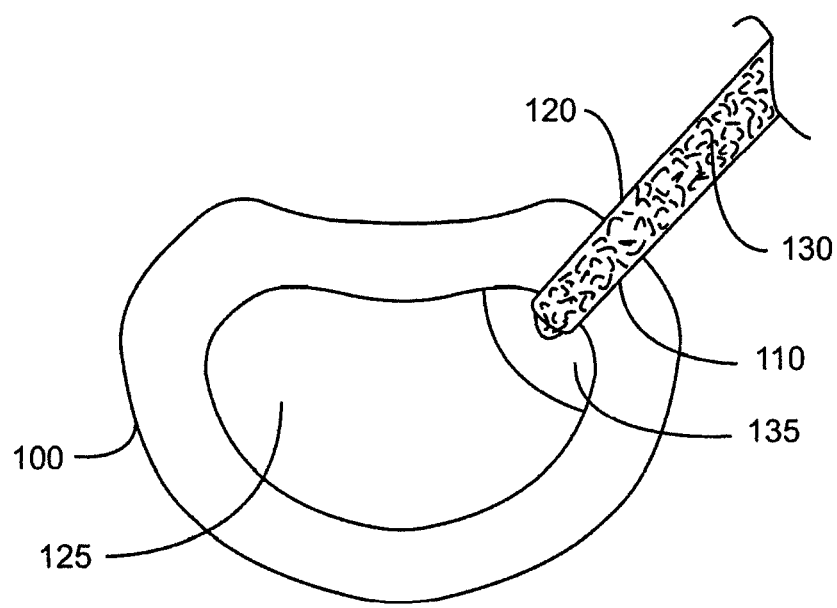
FIG. 1 is a representation of an embodiment of flowable plug material being inserted into an opening in an annulus in accordance with the present invention.
Figure 2:
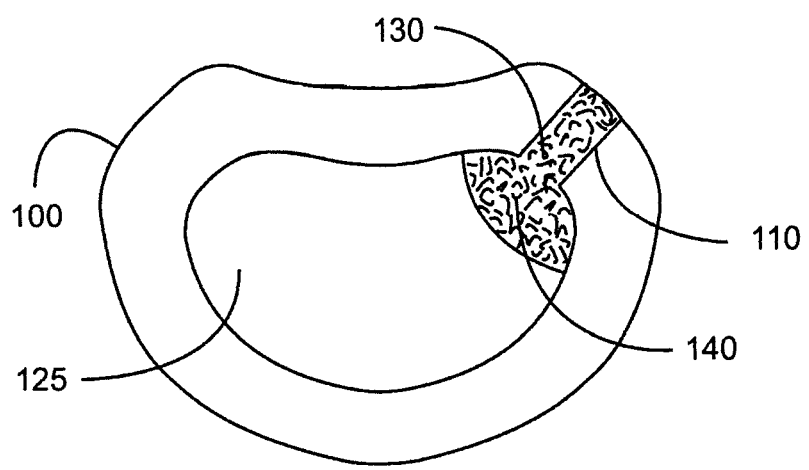
FIG. 2 is a representation of the flowable plug material filling the annulus opening and a portion of the interior of the disc.
Figure 3:
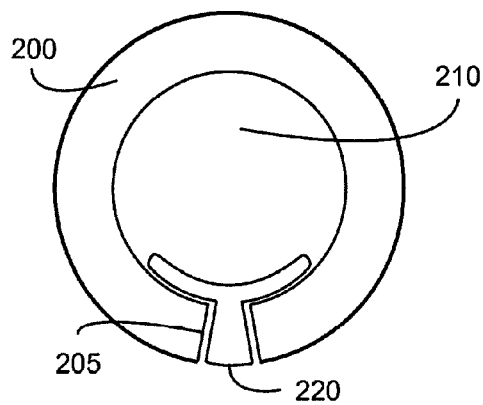
FIG. 3 is a representation of an embodiment of a flexible plug disposed in an annulus opening in accordance with the present invention.

Referring initially to FIGS. 1 and 2, an embodiment of a soft tissue repair system in accordance with the present invention is illustrated. This embodiment uses a plug to fill the opening. In this embodiment, the plug is formed from a flowable or formable material that can be inserted into an opening in the annulus and that can fill the shape of the annulus and any voids in the nucleus pulposus. The flowable material then sets or cures to a flexible material than can retain its assumed shape.

The annulus 100 has an opening 110 passing completely through the annulus and exposing the nucleus pulposus 125. This opening, or any annulus opening as disclosed herein, can result from a tear in the annulus 100 or a passage cut into the annulus 100 during a surgical procedure. A hollow and expandable insertion or injection tool or cannula 120 is inserted through the opening 110 and into the nucleus pulposus 125. In one embodiment, a portion 135 of the nucleus pulposus is removed by discectomy. In accordance with all embodiments herein that use an injection tool or cannula, the injection tool 120 can be dilated to expand the opening 110. An adhesive material 130, i.e., the flowable plug material, is passed through the hollow core of the injection tool 120 and into the portion 135 of the nucleus pulposus 125. As the injection tool 120 is withdrawn from the opening 110, the adhesive material 130 fills the opening. A large portion 140 of the adhesive material remains within the interior of the annulus 100 to aid in retaining the plug in the annulus 100 and to fill the vacated portion 135 of the nucleus pulposus 125. Therefore, the plug will not migrate inward or outward through the opening. Suitable adhesive materials include silicone adhesives and resorbable silicone adhesives.

Figure 4:
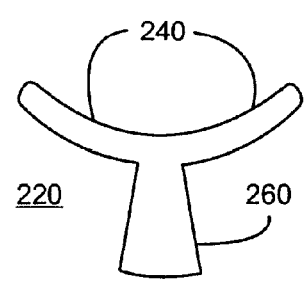
FIG. 4 is a representation of the flexible plug of FIG. 3.

Referring to FIGS. 3-7, another embodiment of a soft tissue repair system utilizing a plug is illustrated. In this embodiment, the plug 220 is formed from a soft, rubbery flexible material. The plug 220 includes a stem or plug portion 260 and an opposing pair of wing portions 240. The plug 220 has a natural or resting position as shown in FIG. 4 and is of sufficient flexibility and resiliency that the opposing pair of wing portions 240 can be bent to fit through an opening 205 in the annulus 200 and return to the natural position within the nucleus pulposus 210. In one embodiment, the wing portions 240 have a curvature in the natural position that matches the curvature of the interior of the annulus 200.

When the wing portions 240 return to their natural positions within the nucleus pulposus 210, intradiscal pressure on the wing portions 240 holds the plug 200 in position. In addition, the stem portion 260 holds the plug 220 in position by providing pressure against the sides of the opening 205. Using the stem portion 260 to hold the plug 220 in the opening 205 is enhanced by forming the stem portion 260 with a wedge shape such that the larger or fatter portion of the wedge is disposed in the opening 205 adjacent the outside of the annulus 200.

In order to insert the plug 220 into the opening 205 of the annulus 200, an injector or cannula 280 (FIG. 5) is used. The injector 280 includes a hollow outer tube 285 that has an outer diameter 225 that is selected to accommodate the size of the opening 205. In one embodiment, the outer diameter 225 is selected so that the outer tube 285 can pass into the opening 205. The outer tube 208 also has an inner diameter 245 that is selected to accommodate the plug 220 and to bend or compress the wing portions 240 of the plug 220 to a size that will pass through the opening 205 in the annulus 200. The injector 280 also includes a clamping mechanism 290 running through the inner diameter 245 of the outer tube 285. The clamping mechanism 290 holds the stem portion 260 of the plug 220. A handle portion 295 is attached to the clamping mechanism 290. The handle portion 295 can move the clamping mechanism 290 through the hollow outer tube 285 and can actuate the clamping mechanism 290 to grip or to release the plug 220. In one embodiment, the clamping mechanism 290 is formed from a pair of opposing, spring-loaded arms. As the arms are drawn into the outer tube by the handle portion, the arms are pulled together, clamping the stem of the plug between them. As the arms are pushed out from the outer tube, the arms move away from each other under the spring-loaded force, releasing the stem of the plug.

Figure 5:
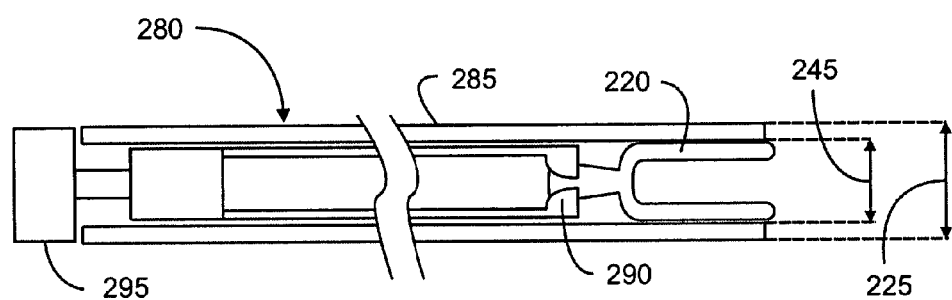
FIG. 5 is a schematic representation of an embodiment of an inserter mechanism holding the flexible plug of FIG. 3.
Figure 6:
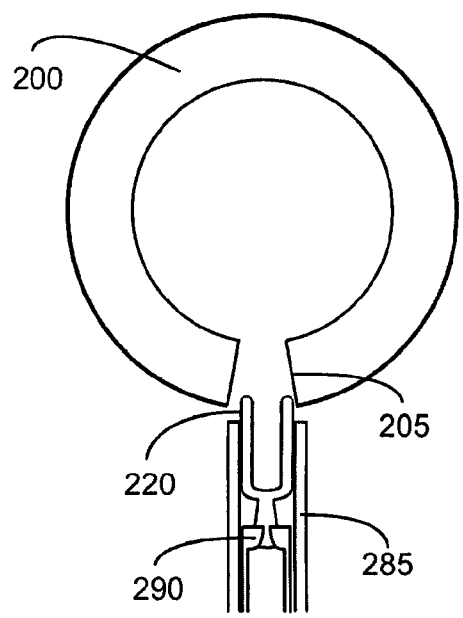
FIG. 6 is a schematic representation of the inserter mechanism of FIG. 5 inserting the flexible plug in an annulus opening.
Figure 7:
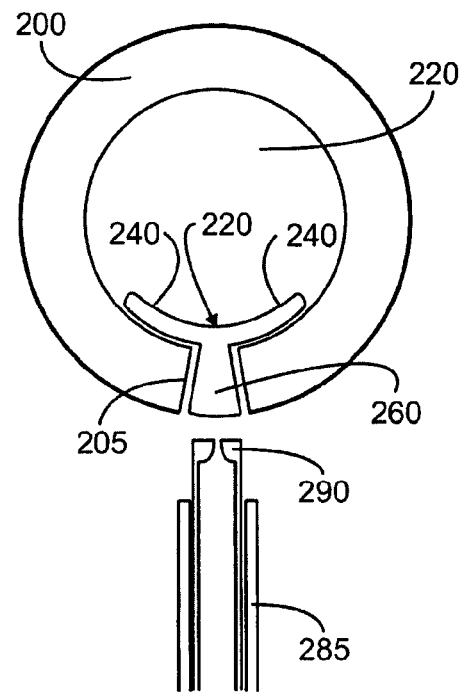
FIG. 7 is a schematic representation of the inserter mechanism of FIG. 5 following insertion of the flexible plug in the annulus opening.

In use, the handle portion 295 pushes the clamping mechanism 290 out from the inner diameter 245 of the outer tube 285, and the stem portion 260 of the plug 220 is placed within the clamping mechanism 290. The handle portion 295 then draws the clamping mechanism 290 into the outer tube 285, which pulls the plug 220 into the inner diameter 245, deforming the wing portions 240 (FIG. 5). The injector 280 is then brought adjacent the opening 205 of the annulus 200, and the handle portion 295 advances the clamping mechanism 290 and the plug 220 out from the outer tube 285 (FIG. 6). As the plug is advanced, the wing portions 240 pass within the opening 205 so that the opening prevents the wing portions 240 from returning to their natural position. Once the wing portions 240 pass sufficiently through the opening 205, they expand in the nucleus pulposus 210 to their natural state, contacting and securing the plug 220 in the opening 205 (FIG. 7). The clamping mechanism 290 releases the stem portion 260 of the plug 220, and the injector 285 is removed.

Although a plug alone sufficiently repairs and seals annulus openings, the size and shape of annulus openings vary creating mismatches and gaps between the plug and the opening. In addition the curvature of the internal or winged portions of the plug may not exactly match or mirror the interior shape of the annulus. In one embodiment of the soft tissue repair system of the present invention, a first flexible plug is used in conjunction with a second flowable plug material to compensate for the gaps or mismatches between the annulus opening and the flexible plug. The flowable plug material, for example as described above, can be used in combination with any of the plug embodiments described herein, including flexible plugs and cover-type plugs or clamps.

Figure 8:
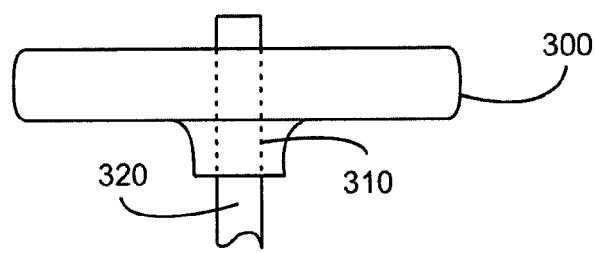
FIG. 8 is a representation of another embodiment of a flexible plug having a central hole in accordance with the present invention.
Figure 9:
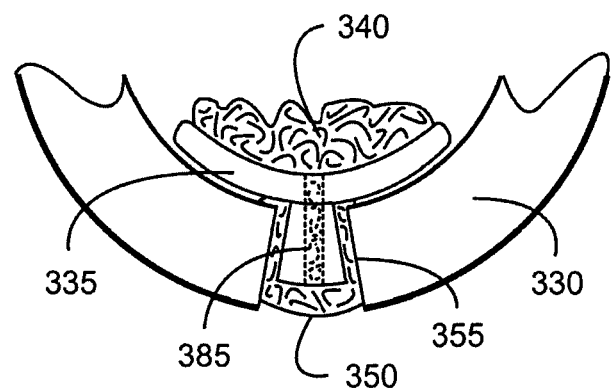
FIG. 9 is a representation of an embodiment of a flexible plug in combination with an embodiment of a flowable plug material disposed in an annulus opening.

In one embodiment, the second flowable plug material is inserted through the first plug such that the flowable plug material is located between the first plug and the nucleus pulposus. Referring to FIG. 8, any given plug 300, for example a first flexible plug, can include a hole or channel 310 that runs completely through that plug. This hole 310 accommodates a hollow tube 320. The hollow tube 320 functions as a conduit to inject flowable plug material through the flexible plug 300. As shown in FIG. 9, an embodiment of a first flexible plug 335 is inserted into an opening 355 in an annulus 330. The second flowable plug material, for example adhesive material, is passed through a central hole 385 in the flexible plug so that a portion 340 of the flowable plug material is disposed inside the annulus 330 adjacent the flexible plug 335. The flowable plug material also fills the central hole and is disposed in any spaces between the flexible plug and the opening 355. A portion 350 of the flowable plug material seals the outside of the opening 355.

Figure 10:
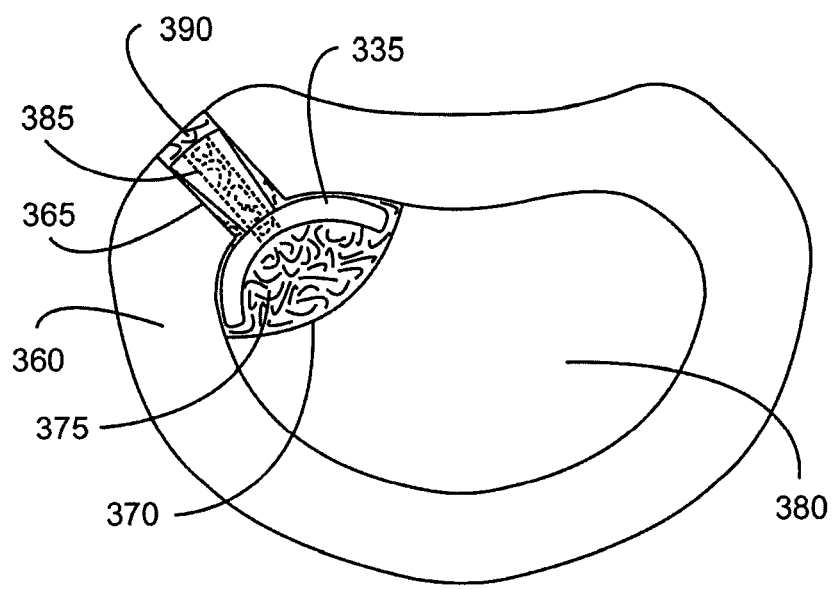
FIG. 10 is a representation of another embodiment of a flexible plug in combination with an embodiment of a flowable plug material disposed in an annulus opening.

Referring to FIG. 10, the first flexible plug 225 is inserted in another opening 365 in an annulus 360, and the second flowable plug material is passed through the central hole 385 in the opening so that a portion 375 of the flowable plug material completely fills a cavity 370 in the nucleus pulposus 380. The flowable plug material also fills the central hole and is disposed in any spaces between the flexible plug and the opening 365. A portion 390 of the flowable plug material seals the outside of the opening 365. In either embodiment, the flowable plug material sets or hardens over time to form a second flexible plug material.

Figure 11:
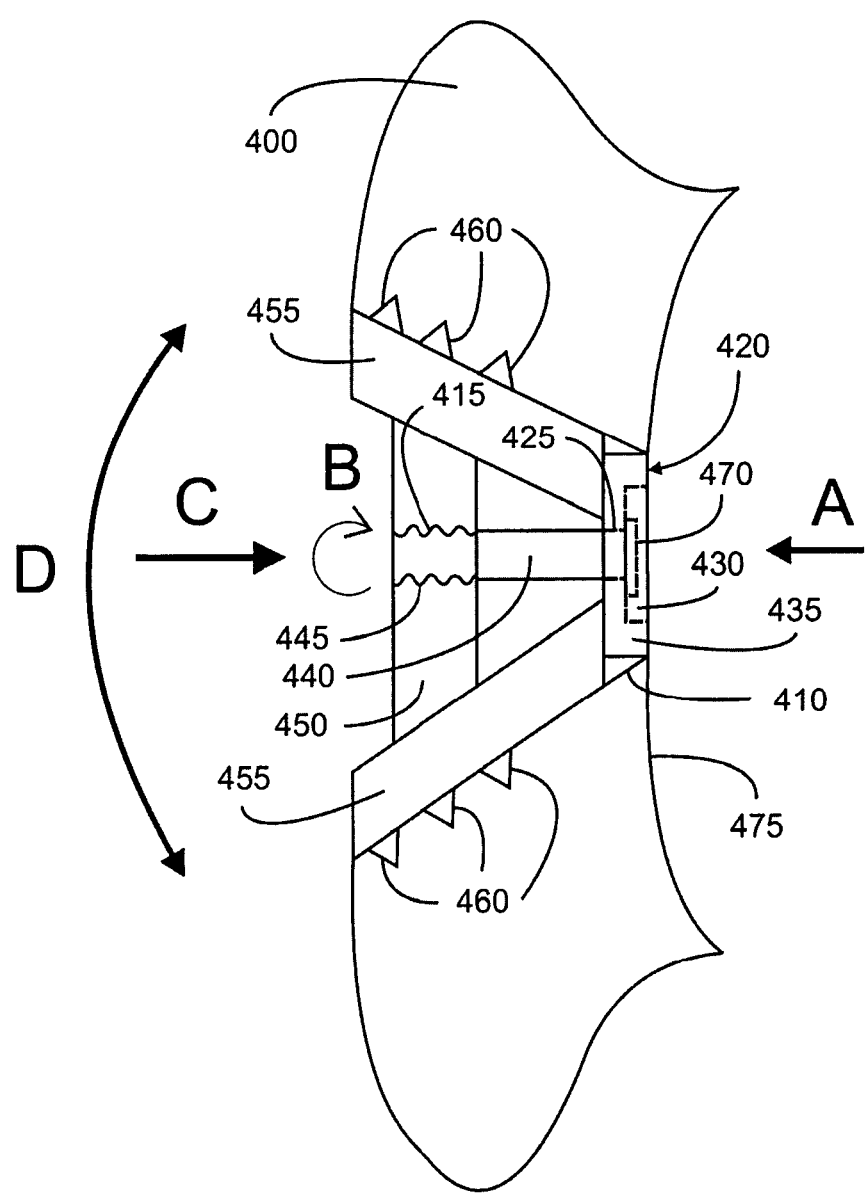
FIG. 11 is a representation of another embodiment of a plug disposed in an annulus opening in accordance with the present invention.
Figure 12:
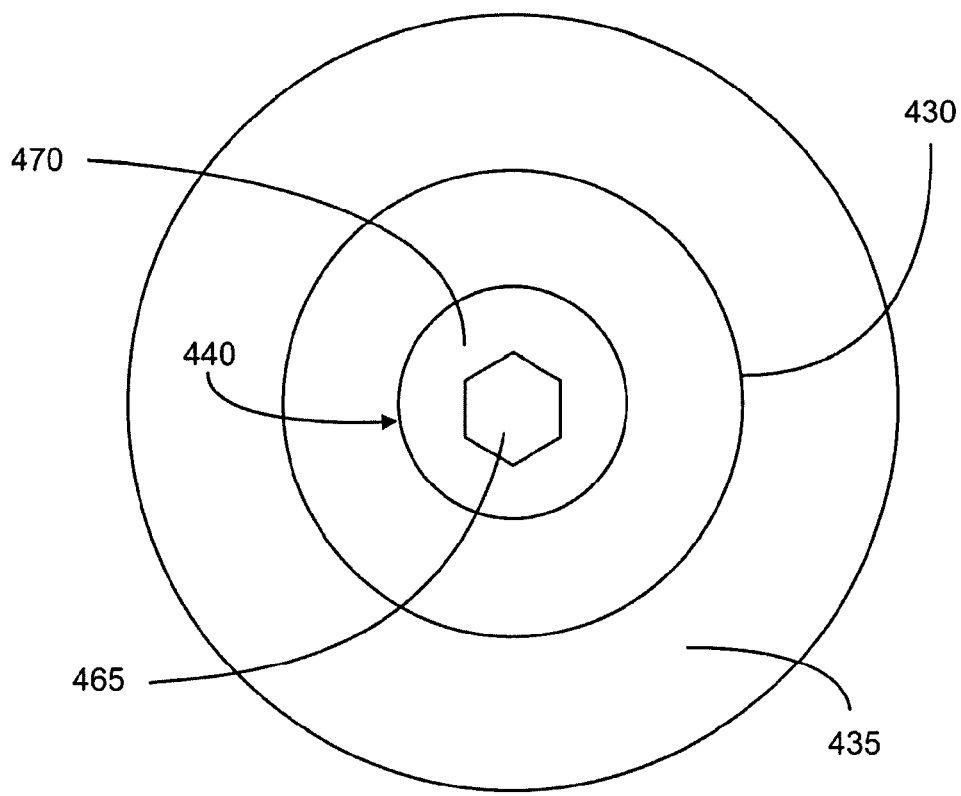
FIG. 12 is a view of an embodiment of the cap portion of the plug of FIG. 11.

Referring to FIGS. 11-12, another embodiment of the soft tissue repair system of the present invention using a plug is illustrated. The plug 420 includes a cap 435 and a screw 440 extending through a hole 425 in the cap 435. The screw 440 is free to rotate about its long axis without rotating the cap 435. The proximal end of the screw 440 includes a head 470 that is located in a recess 430 of the cap 435. Therefore, the head 470 of the screw 440 does not extend beyond the cap 435. The head 470 is larger in diameter than the hole 425 and includes a slot 465 (FIG. 12) to accept a tool for turning the screw 470. In one embodiment, the slot 465 is a hexagonal slot. Suitable materials for the cap 435 and screw 440 include, but are not limited to titanium and polyether ether ketone (PEEK). In one embodiment, the screw 440 is titanium and the cap 435 is PEEK.

The distal end of the screw includes threads 445. The threads 445 pass through a threaded opening 415 in a spreading bar 450 of the plug 420. Suitable materials for the spreading bar include, but are not limited to titanium, PEEK, polycarbonate-urethane (PCU) and combinations thereof. For example, the portion of the spreading bar 450 containing the threaded opening 415 is constructed of titanium, and the body of the spreading bar 450 including all bearing surfaces is PEEK or PCU. The plug also includes are least one pair of opposing arms 455. Each arm 455 includes a plurality of barbs or tangs 460. The opposing arms 455 are in contact with the cap 435 and with opposite ends of the spreading bar 450. Additional opposing pairs of arms can be included. The plug 420 is inserted in the direction of arrow A through an opening 410 in the annulus 400. The screw 440 is rotated in the direction of arrow B, pulling the spreading bar 450 in the direction of arrow C and spreading the opposing arms 455 in the directions indicated by arrow D. This impinges the opposing arms 455 on the walls of the opening, driving the tangs 460 into the annulus and anchoring the plug 420 in the opening 410. In one embodiment, the cap 435 is of sufficient size to completely close the opening, and the cap 435 is positioned flush with the exterior surface 475 of the annulus 400. As with all plugs described herein, this first plug can be used in combination with a second flowable plug material to compensate for any gaps between the opening 410 and the plug 420.

Figure 13:
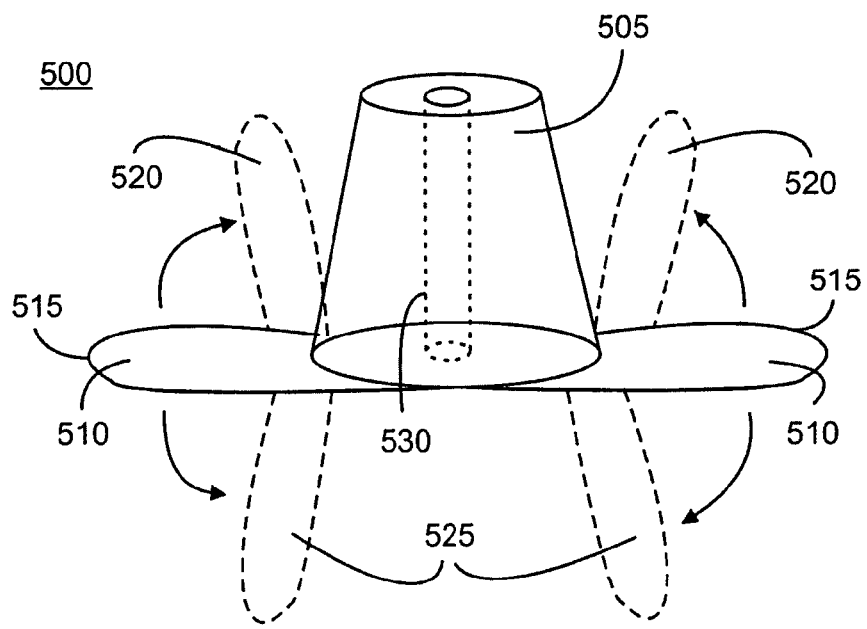
FIG. 13 is a perspective representation of another embodiment of a flexible plug in accordance with the present invention.
Figure 14:
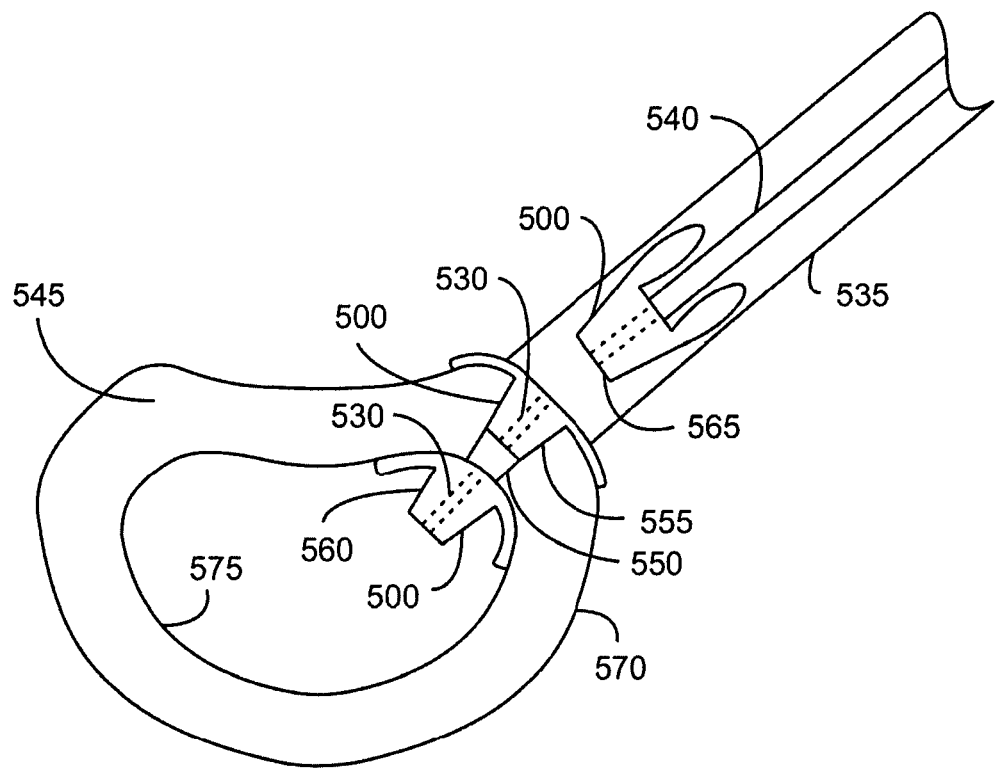
FIG. 14 is a schematic representation illustrating the insertion of the plug of FIG. 13 in an annulus opening.

Referring to FIGS. 13 and 14, another embodiment of the soft tissue repair system of the present invention using a plug is illustrated. This embodiment utilizes a plug 500 having a conical main body 505 that is constructed from a load bearing compliant material that mimics the load bearing properties of the annulus 545. The plug 500 also includes a pair of opposing flexible wings 510. In one embodiment, the flexible wings 510 are constructed from the same material as the main body 505. In this embodiment, the main body 505 and flexible wings 510 can be molded as a single unit. Alternatively, the wings 510 are constructed from a material or fabric that can be sutured to the annulus 545. In this embodiment, the flexible wings 510 are formed separate from the main body 505 and are subsequently attached to the main body 505. In one embodiment, the plug 500 includes a plurality of pairs of opposing flexible wings. In another embodiment, the plug 500, in place of opposing flexible wings, includes a ring or flange of flexible material attached to one end of the main body 505.

The flexible wings have a natural or resting position 515 and can be flexed or bent between a first position 520 adjacent the main body 505 and a second position 525. The plug 500 also includes a central hole 530 that passes completely through the main body 505. The hole facilitates attachment of an inserter 540 to grip the plug 500 during insertion and introduction of a flowable plug material through the main body 500 and into the interior of the annulus 545. The opposing flexible wings 510 can be attached to either the larger or smaller end of the conical-shaped main body 505.

In order to insert the plug 500 into the opening 550 of the annulus 545, an inserter 540 is attached to the plug 500, and the plug is pushed through the central bore of a cannula or endoscope 535 bending the flexible wings 510 into the second position 525. The smaller diameter side 565 of the main body 505 is presented to the opening 550 first. The plug can be inserted to a first position 555 where the main body is disposed in the opening 550 and the flexible wings are in contact with the exterior surface 570 of the annulus 545 or a second position 560 where the main body 500 is passed completely through the opening 550 and the flexible wings are in contact with the interior surface 575 of the annulus 545. In either the first position 555 or the second position 560, sutures (not shown) can be used to secure the flexible wings to the annulus. In addition, this plug 500 can be used in combination with the flexible plug material. The plug blocks the pressure from the nucleus pulposus and bears loads acting on the spine.

Figure 15:
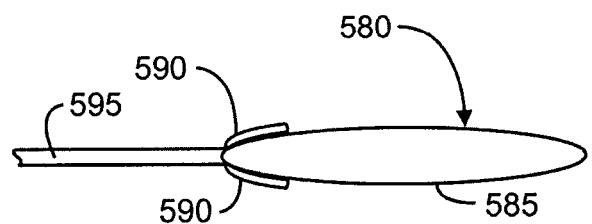
FIG. 15 is a representation an another embodiment of a plug in accordance with the present invention in a deflated position.
Figure 16:
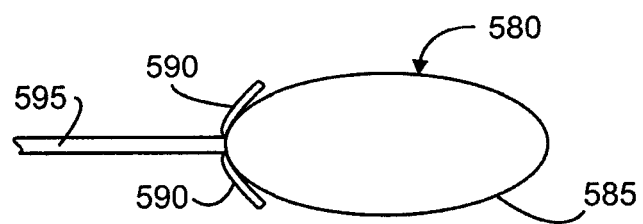
FIG. 16 is a representation of the plug of FIG. 15 in an inflated position.
Figure 17:
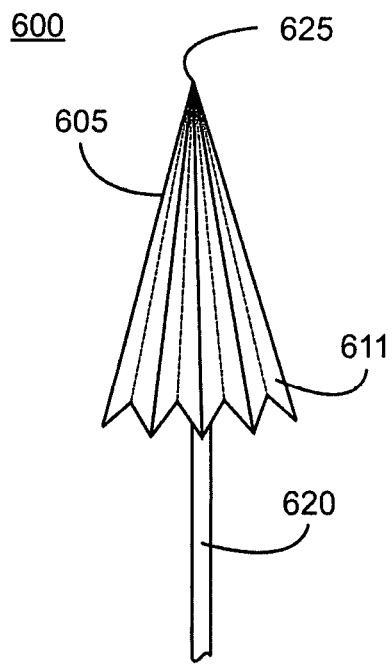
FIG. 17 is a representation of another embodiment of a plug in accordance with the present invention in a closed position.
Figure 18:
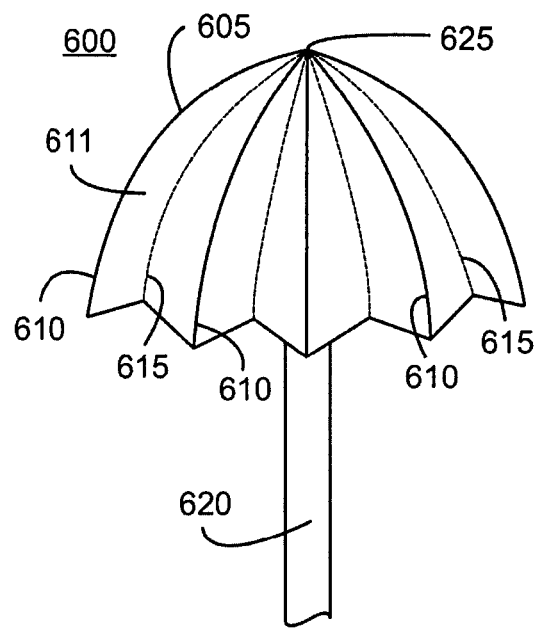
FIG. 18 is a representation of the plug of FIG. 17 in a first open position.

Referring to FIGS. 15 and 16, another embodiment of the soft tissue repair system of the present invention using a plug is illustrated. In this embodiment, the plug 580 is an inflatable balloon constructed from a material that can be inflated or stretched to fill an opening in an annulus. The plug can maintain this inflated position under the pressure of a fill gas or flowable material or can set or harden in the inflated position, obviating the need to maintain a pressurized fill gas or flowable fill material within plug. The inflatable balloon plug 580 includes a balloon portion 585 made from a polymeric material and one or more flexible wings 590 attached to one end of the balloon portion 585. The flexible wings can engage the exterior or interior surface of the annulus adjacent the opening on the annulus. A filler tube 595 is also provided in communication with the balloon for communicating filler or inflating material, e.g., gas or flowable plug material, into the balloon. Although illustrated as a uniform circular or oblong balloon, the balloon portion 585 can be constructed with a non-uniform shape and can include bulging sections that will inflate to larger sizes and that can be positioned on the interior or exterior of the annulus to hold the plug in place.

The plug 580 is inserted into an opening in the annulus with the balloon portion 585 in a deflated state (FIG. 15). The balloon portion is then inflated (FIG. 16). Inflation can be initiated using a pressurized gas such as an inert gas passed through the filler tube 595. Following gas expansion or separately as an alternative to gas expansion, a polymeric material, i.e., a flowable plug material, is introduced through the filler tube 595 into the interior of the balloon section 585. In one embodiment, the balloon section 585 is inflated and filled with elastomeric sheath. Once inflated, the balloon section 585 fills and seals the opening in the annulus, conforming to the shape of the walls of the opening. The filler tube is then removed.

Figure 19:
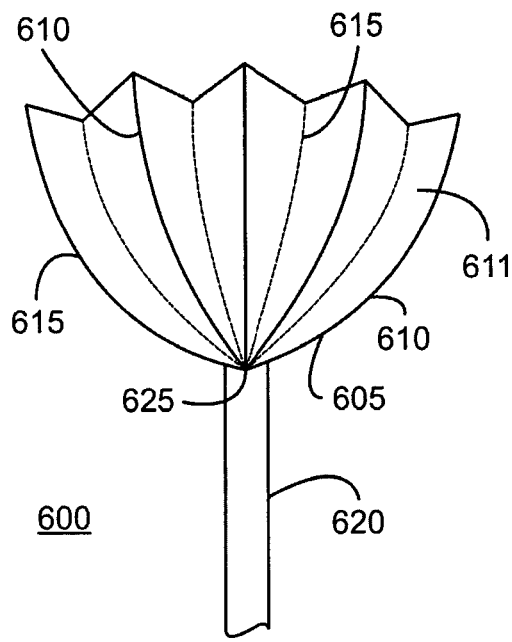
FIG. 19 is a representation of the plug of FIG. 17 in a second open position.
Figure 20:
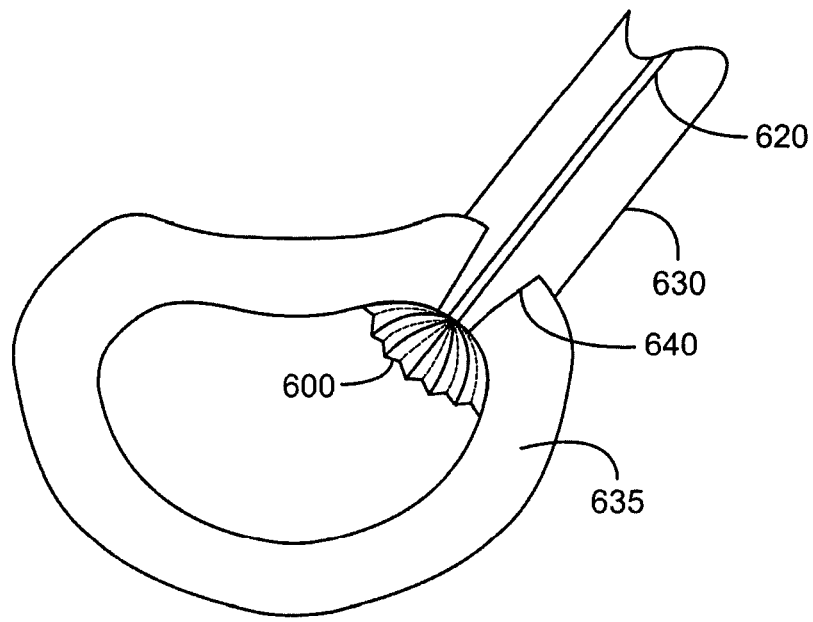
FIG. 20 is a schematic representation of the plug of FIG. 17 in the second open position deployed in an annulus opening.

Referring to FIGS. 17-20, another embodiment of the soft tissue repair system of the present invention using a plug is illustrated. In this embodiment, the plug 600 utilizes an umbrella mechanism. The plug 600 includes a plug portion 605 formed with a plurality of flexible rods 610. Each flexible rod 610 has one end attached to a pivot point 625. Suitable materials for the flexible rods 610 include titanium and polymers. A thick compliant and foldable sheet of material 611 is attached to and covers the flexible rods 610. Suitable materials for the sheet of material 611 include, but are not limited to, polymers and polymeric sheath. The sheet of material forms folds or pleats 615 between the flexible rods 610. An inserter and actuator 620 is removably attached to the pivot point 625. In one embodiment, the inserter and actuator 620 is attached to the pivot point 625 with a threaded attachment. The actuator 620 can move the plug portion 605 from a closed insertion position (FIG. 17) to either a first open position (FIG. 18) or a second inverted open position (FIG. 19). The selected open position is based on the shape of the annulus adjacent the opening, i.e., concave or convex.

To insert the plug 600 into an opening 640 in an annulus 635, the inserter 620 is attached to the pivot point 625 of the plug portion 605, and the plug 660 in the closed position is passed through a cannula 630 pivot point 625 first. The plug portion 605 is passed completely through the opening 640, and the inserter 620 moves the plug portion to the second inverted open position within the annulus 635. The sheet of material 611 is secured to the annulus 635 using sutures (not shown). The inserter 620 is unscrewed and removed. In one embodiment, a second flowable plug material is used to fill the opening and to fill the plug portion.

Figure 21:
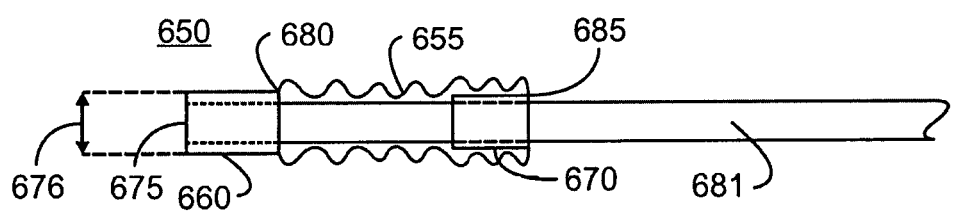
FIG. 21 is a representation of another embodiment of a plug in accordance with the present invention in an initial position.
Figure 22:
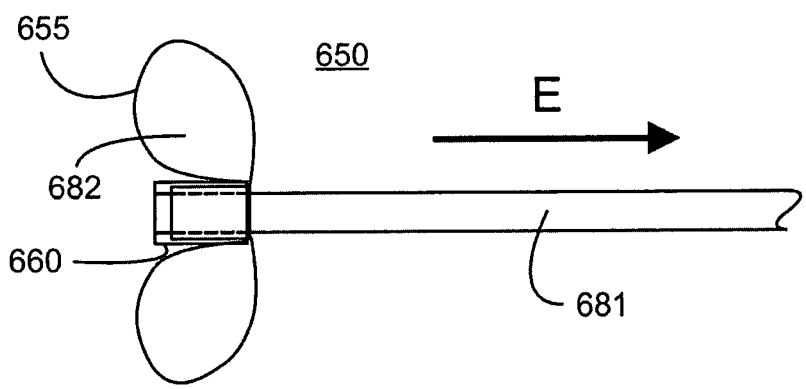
FIG. 22 is a representation of the plug of FIG. 21 in an expanded position.

Referring to FIGS. 21-22, another embodiment of the soft tissue repair system of the present invention using a plug is illustrated. In this embodiment, the plug 650 a compliant sheet 655 arranged as a tube or sock. Suitable materials for the compliant sheet 655 include, but are not limited to, polymeric sheath. The plug 650 includes a first cylindrical collar 660 and a second cylindrical collar 670. The collars are constructed of a stiff elastomeric material, and the first collar 660 has a diameter 676 that is larger than the second collar 670 such that the second collar 670 fits inside the first collar 660. In one embodiment, each collar has a length that is less than the thickness of the annulus opening to be repaired. A first end 680 of the compliant sheet 655 is attached to the first collar 660, and a second end 685 of the compliant sheet 655 is attached to the second collar 670. Since the compliant sheet 655 is arranged as a tube or sock, the compliant sheet 655 is attached around the entire outer diameter of each collar. In one embodiment, the compliant sheet 655 is attached to the first collar 660 such that in an initial state (FIG. 21) the first collar 660 is located outside the compliant sheet 655, and the compliant sheet is attached to the second collar 670 such that in the initial state the second collar 670 is located inside the compliant sheet.

The plug 650 also includes an inserter rod 681 that runs through the second collar 670, the tubular compliant sheet 655 and the first collar 660 and is releasably attached inside the first collar 660 at an end 675 opposite to where the compliant sheet 655 is attached to the first collar 660. The inserter rod 681 can be releasably attached to the using a threaded connection or a frangible connection. In one embodiment, the inserter rod 681 is hollow and the end 675 of the first collar 660 has an opening such that a flowable plug material can be passed through the inserter rod 681 and first collar 660.

The plug 650, in the initial state, is inserted into an opening in an annulus. The inserter rod is moved in the direction of arrow E (FIG. 22) until the second collar 670 is disposed inside the first collar 660, and the plug 650 is in the expanded state. In one embodiment, the first and second collars lock into this nested state, for example using a pressure fit between the two collars, interlocking tangs, ratcheted closer mechanisms or any other suitable mechanism. In the expanded state, the compliant sheet 655 gathers together and expands in size, filling the opening of the annulus. In one embodiment, the interior 682 of the compliant sheet 655 is not filled. Alternatively, the interior 682 of the compliant sheet 655 is filled with a flowable plug material. After the plug 650 is placed in the expanded position, the inserter rod 681 is removed. In one embodiment, the compliant material is sutured to the annulus.

Figure 23:
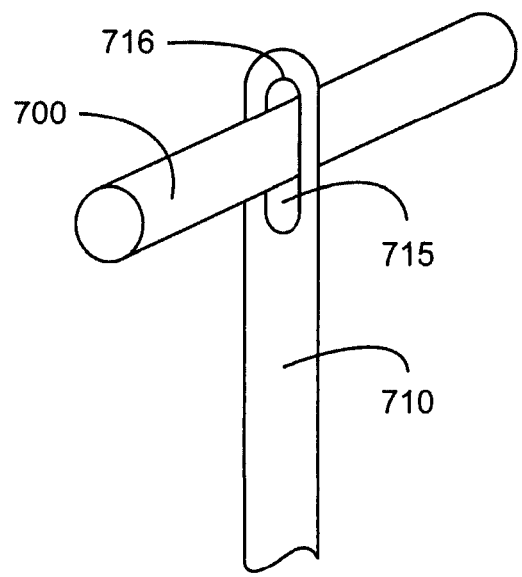
FIG. 23 is a representation of another embodiment of a flexible plug disposed in a plug inserter in accordance with the present invention.
Figure 24:
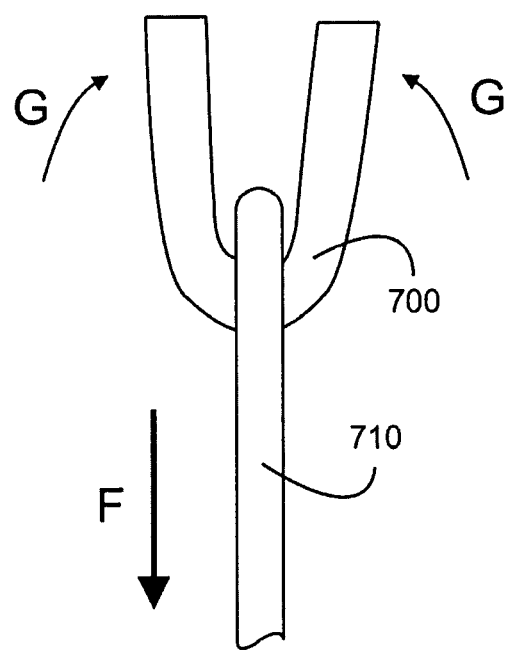
FIG. 24 is representation of the plug and plug inserter of FIG. 23 with the plug in a bent position.
Figure 25:
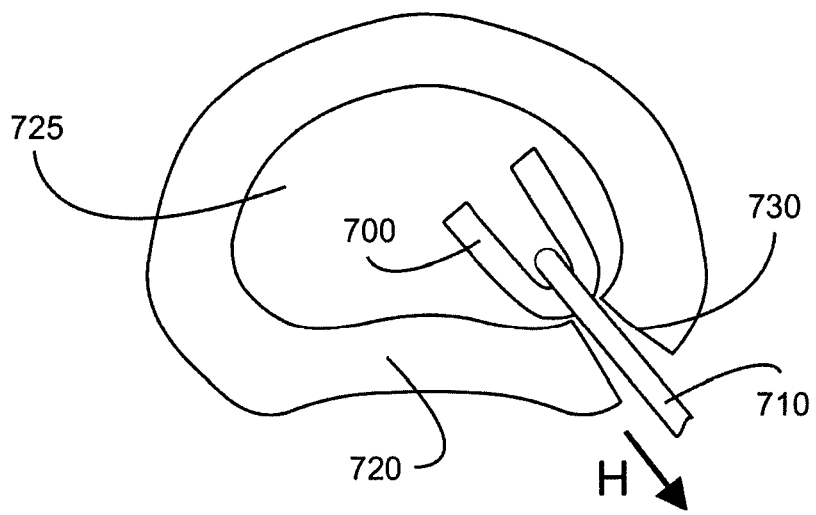
FIG. 25 is a schematic representation of the plug of FIG. 23 in the bent position disposed in an annulus opening.

Referring to FIGS. 23-25, another embodiment of the soft tissue repair system of the present invention using a plug is illustrated. In this embodiment, the plug 700 has a cylindrical or rod shape and is constructed of a flexible and resilient material. In one embodiment, the material is PCU. In one embodiment, the plug has a circular, oval, square or rectangular cross-section, although other cross-sectional geometries are also possible. The plug 700 is passed through a slot 715 in an inserter rod 710. Suitable materials for the inserter rod 710 include, but are not limited to, titanium and polymers. The slot 715 is sized to accept the plug 700 and to hold the plug securely when the plug is inserted into an opening 730 in an annulus 720. In addition, the slot 715 includes a top edge 716 formed or sharpened to cut through the plug 700. As show in FIG. 24, when the inserter rod 710 is moved in the direction of arrow F through an opening, the plug 700 on either side of the inserter rod 710 will bend in the direction of arrows G.

Referring to FIG. 25, the inserter rod 710 holding the plug 700 is passed through the opening 730 in the annulus 720 until the entire plug 700 is located in the interior 725 of the annulus 720. The inserter rod 710 is sized to move freely through the opening. The plug 700 is sized to fit tightly within the opening. As the inserter rod 710 is pulled back through the opening 730 in the direction of arrow H, the plug 700 doubles over, bending in the direction opposite to arrow H. The bent plug 700 passes back through the opening 730, becoming logged in the opening 730. Continuing to pull the inserter rod 710 slices through the plug 700, forming two pieces of plug and freeing the inserter rod 710. The two pieces of plug remain in the opening, and any portion of the two pieces that extends beyond the outer edge 721 of the annulus 720 is cut off and removed. Alternatively, the inserter rod slices through the doubled over plug as the plug and rod are initially inserted through the annulus opening. The freed inserter rod is then pulled back through the annulus opening. A second flowable plug material can also be introduced into the opening around the two plug pieces, or the plug can be dipped into or coated with a second flowable plug material prior to insertion in the opening.

Figure 26:
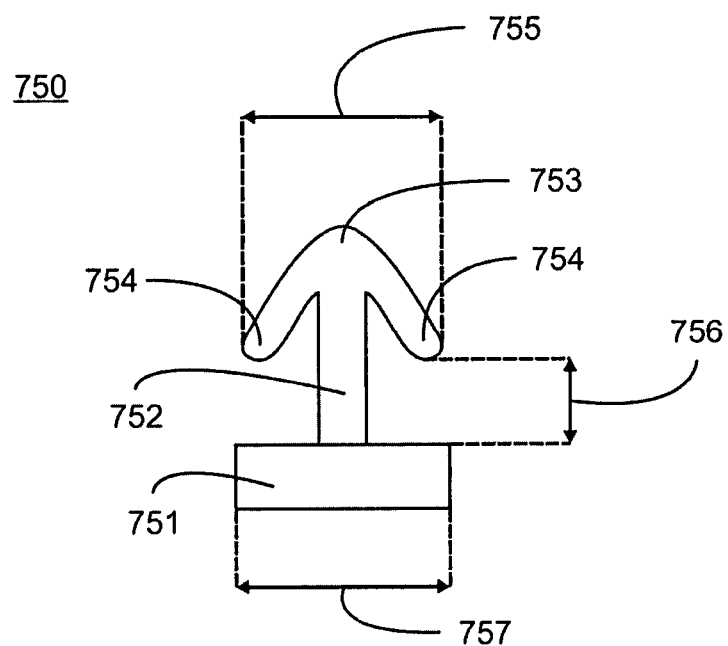
FIG. 26 is a representation of another embodiment of a flexible plug for use in accordance with the present invention.
Figure 27:
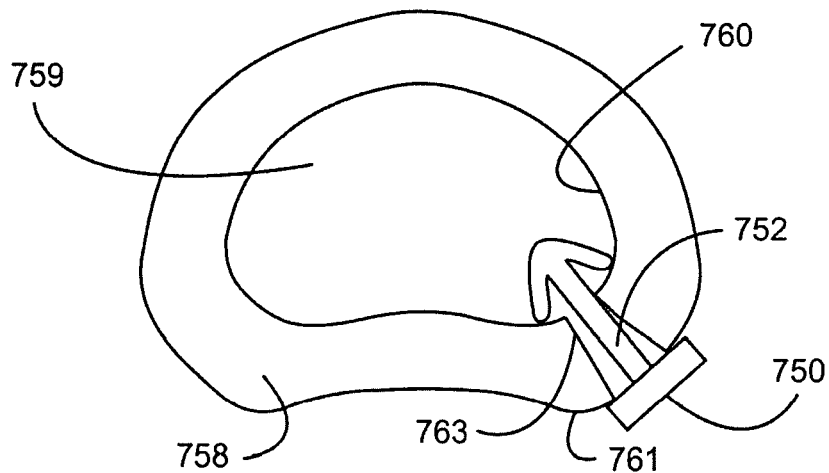
FIG. 27 is a schematic representation of the plug of FIG. 26 inserted into an annulus opening.
Figure 28:
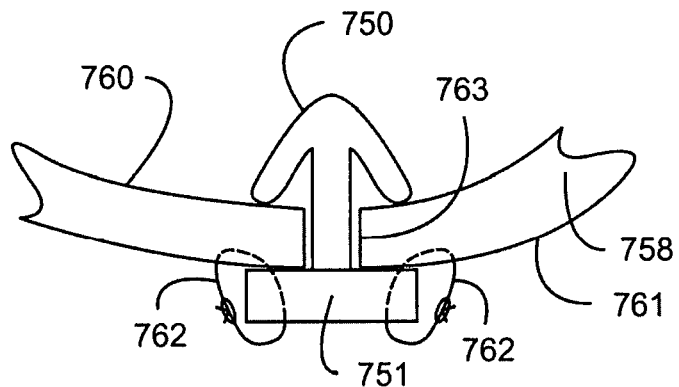
FIG. 28 is a schematic representation of the plug of FIG. 26 inserted into an annulus opening and sutured to the annulus.

Referring to FIGS. 26-28, another embodiment of the soft tissue repair system of the present invention using a plug is illustrated. In this embodiment, the plug 750 includes a base 751 having a disc shape, a stem 752 extending from the base and an anchoring structure 753 extending from an end of the stem 752 opposite the base 751. In one embodiment, the disc-shaped base 751 has a diameter 757 that is greater than the size of the opening 763 in the annulus 758 that is to be repaired. In one embodiment, the anchoring structure 753 includes at least two or alternatively a plurality of arms 754 arranged as diametrically opposed pairs and extending out from the stem 752 and back along the stem 752 toward the base 751. The arms 754 extend out from the stem 752 a distance 755 that is greater than the size of the opening 763 in the annulus 758 that is to be repaired by the plug 750. The arms 754 are flexible and can bend toward the stem 752. In addition to being formed as a plurality of independent arms, the anchoring structure 753 can be formed as a continuous flange of material that extends back toward the base and away from the stem to form a cone. In one embodiment, the base 751, stem 752 and anchoring structure 753 are molded as a single unitary structure. Suitable materials for the plug 750 include, but are not limited to, PCU.

The anchoring structure 753 forms a wedge shape to facilitate insertion of the plug 750 through the opening 763 in the annulus 758. In addition, the arms 754 of the anchoring structure 753 flex or compress to ease insertion through the opening 763. The plug 750 is inserted through the opening 763 until the anchoring structure 753 is completely disposed within the interior 759 of the annulus 758. The arms 754 can then return or expand to their natural or resting position. In this position, the arms 754 engage the interior surface 760 of the annulus 758. The stem 752 is formed of a length such that the distance 756 between the anchoring system 753 and the base 751 allows the anchoring system 753 to engage the interior surface 760 of the annulus 758 while the base 751 engages the exterior surface 761 of the annulus 758. In one embodiment, this distance 756 is selected to be slightly less than the thickness of the annulus 758 or depth of the opening 763 to provide a slight pressure or force in opposite directions on the base 751 and the anchoring structure 753. This assists in holding the plug 750 in the opening 763. Referring to FIG. 28, in one embodiment, sutures 762 are placed through the base 751 and annulus 758 to further anchor the plug 750 in the opening 763. In one embodiment, the plug 750 is used in combination with a second flowable plug material. For example, at least one of the anchoring structure 753 and a stem 752 is coated with or covered with a cap of flowable plug material. As the plug 750 is inserted into the opening, the flowable plug material conforms to the shape of the interior contours of the opening.

Figure 29:
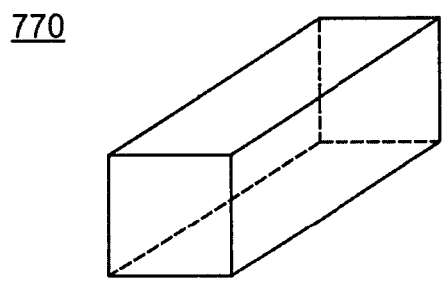
FIG. 29 is a representation of another embodiment of a flexible plug in accordance with the present invention.
Figure 30:
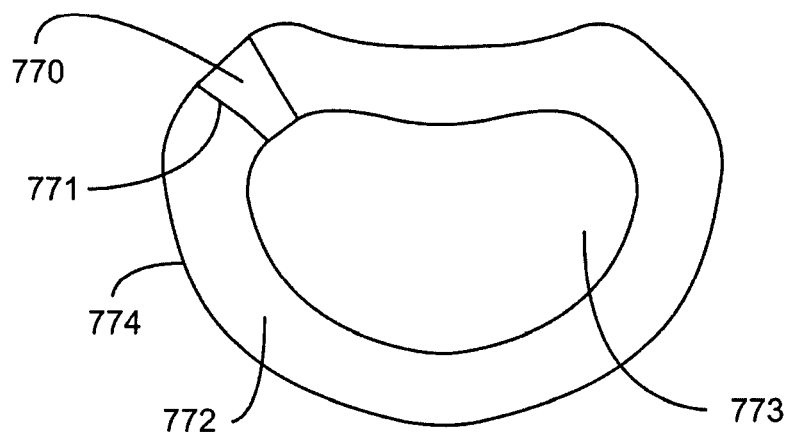
FIG. 30 is a schematic representation of the plug of FIG. 29 disposed in an annulus opening.

Referring to FIGS. 29-30, another embodiment of the soft tissue repair system of the present invention using a plug is illustrated. In this embodiment, the plug 770 is a single block of flexible material. Suitable flexible materials include, but are not limited to, fabric, woven material, PCU and/or collagen. The material may be soaked in tissue growth promoting agents. The plug 770 has an elongated shape, and the cross section of the plug 770 can be any desired geometric shape including, circular, square, rectangular or square. In one embodiment, the plug 770 is formed or molded into the desired shape and length and then is inserted into an appropriate opening in an annulus. The opening in the annulus can be cut to the appropriate size and shaped for the plug. Alternatively, the plug 770 is formed as a standard sized block of material that is custom cut or fitted prior to insertion. Therefore, the plug 770 is custom fit to the size and shape of the opening 771 in the annulus 772 (FIG. 30), taking into account, for example, a narrowing of the opening 711 as the plug extends towards the interior 773 of the annulus 772. In addition, the plug can be trimmed following insertion into the opening 771, for example to be flush or level with the exterior surface 774 of the annulus 772. In one embodiment, the plug 770 is constructed of a material that has cushioning and support properties that mimic those properties from the annulus 772. This plug can also be used in conjunction with the second flowable plug material to fill gaps between the plug 770 and the opening 771 and to assist in anchoring or securing the plug 770 in the opening.

Figure 31:
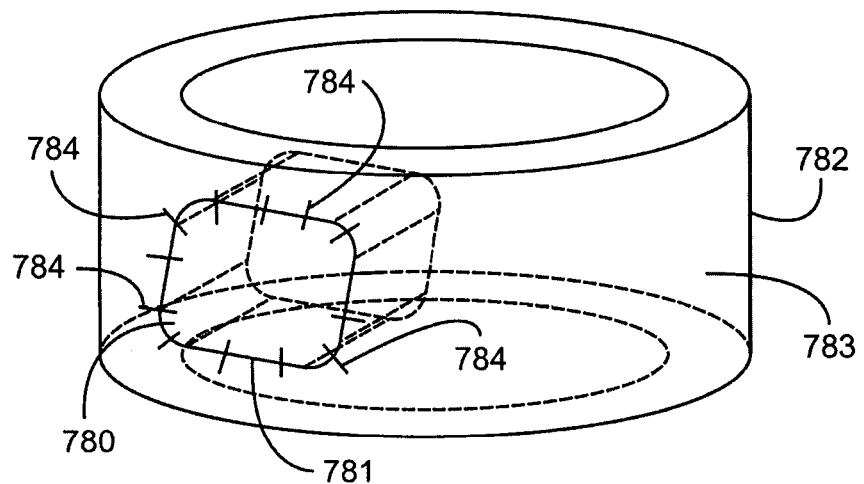
FIG. 31 is a schematic representation of another embodiment of a flexible plug disposed in an annulus opening and sutured to the annulus.
Figure 32:
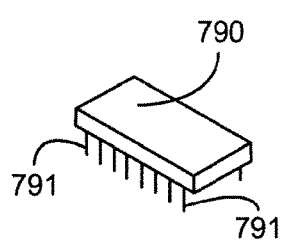
FIG. 32 is a representation of an embodiment of a cover-type plug in accordance with the present invention.
Figure 33:
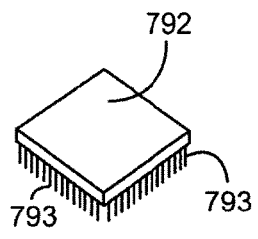
FIG. 33 is a representation of another embodiment of a cover-type plug in accordance with the present invention.
Figure 34:
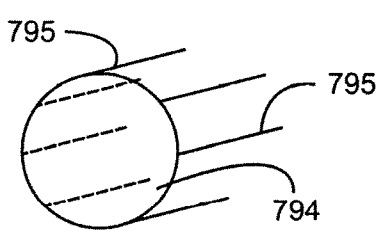
FIG. 34 is a representation of another embodiment of a cover-type plug in accordance with the present invention.

Referring to FIG. 31, in another embodiment, the plug 780 formed from a flexible material is cut to conform to the size and shape of the opening 781 in the annulus 782 and to fill the opening completely. A plurality of stitching elements or sutures 784 are used on the exterior surface 783 of the annulus 782 to secure the plug 780 in the opening 781. Although these plugs have been shown as being inserted into and substantially filling the opening, other plugs can be used that attach to the exterior surface of an annulus and close the opening without extending into the opening. In one embodiment, a cap of covering type plug 790 (FIG. 32) is illustrated that has a rectangular shape that covers an opening and extends around a portion of the exterior of the annulus. This plug 790 also includes a plurality of tangs or prongs 791 extending from one side. These prongs 791 are pressed into the annulus to hold the plug 790 in place. Other embodiments include a square cap type plug 792 with a plurality of prongs 793 (FIG. 33) and a circular cap type plug 794 with a plurality of prongs 795 (FIG. 34). These cap-type plugs can be used with other flexible plugs or a second flowable plug material that fill the opening. In addition, sutures can also be used to anchor the cap-type plugs to the annulus. Suitable materials for the cap like plugs include, but are not limited to, PCU. The prongs can be made of titanium or polymers.

Figure 35:
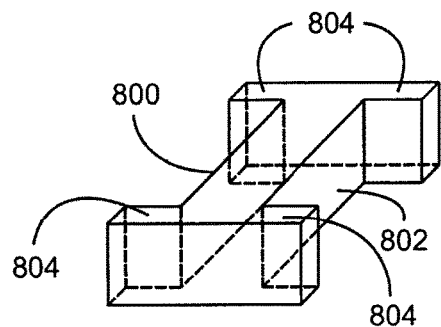
FIG. 35 is a representation of another embodiment of a flexible plug in accordance with the present invention.

Referring to FIG. 35, the plug 800 is formed or cut from a flexible material such as PCU or collagen. The plug has an elongated central body 802 and a pair of opposing flexible extensions 804 on either end of the central body. The central body 802 has a length that is sufficient enough to extend through an opening in an annulus. The area of each end as defined by the flexible extensions 804 and the end of the central body 802 is larger than the opening in the annulus. In addition, the flexible extensions 804 can be sufficiently bent or deformed to fit through the opening in the annulus. In one embodiment, the natural or resting position of each extension 804 extends generally perpendicular to the long axis of the central body 802. The extensions 804 could also extend at an angle or be curved to accommodate the associated curvature of the annulus.

Figure 36:
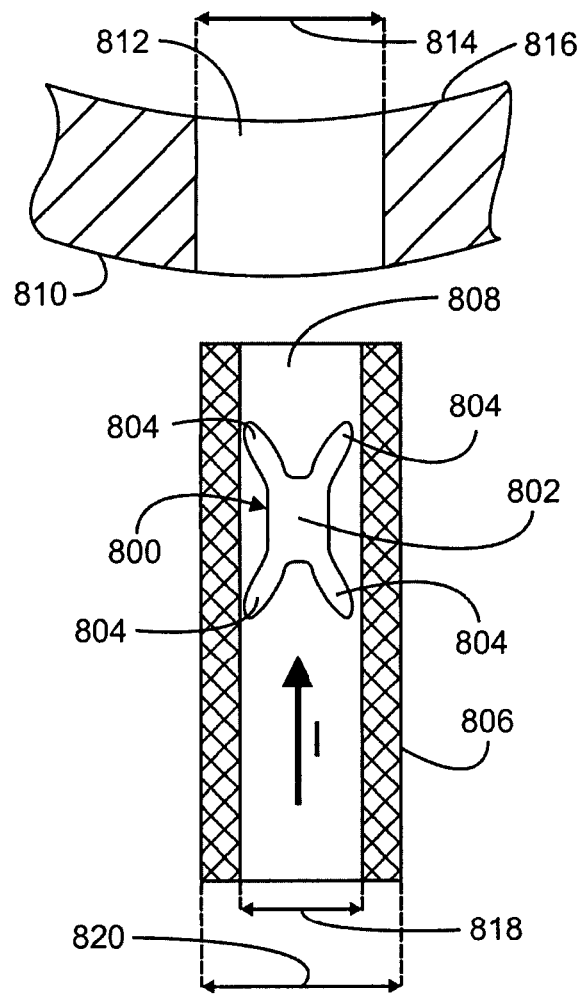
FIG. 36 is a schematic representation of the flexible plug of FIG. 35 disposed in a cannula for insertion into the annulus opening.
Figure 37:
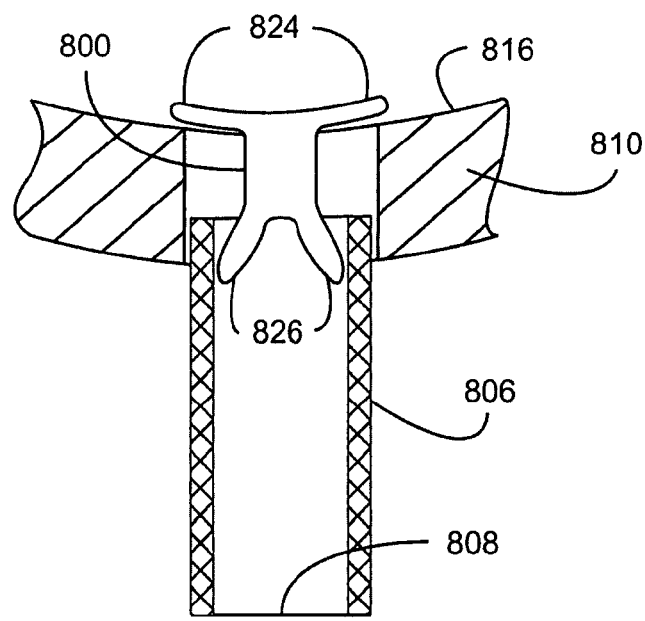
FIG. 37 is a schematic representation of the flexible plug of FIG. 35 disposed in the cannula and partially inserted into the annulus opening.
Figure 38:
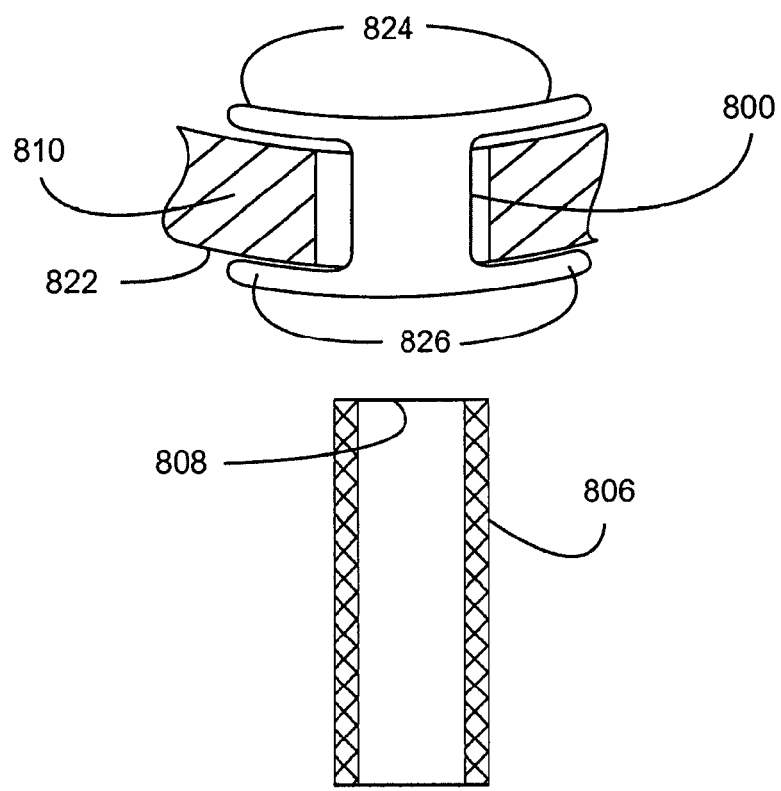
FIG. 38 is a schematic representation of the flexible plug of FIG. 35 and the cannula following insertion into the annulus opening.

Referring to FIGS. 36-38, the plug 800 is placed in the central bore 808 of a cannula or endoscopic tool 806. The diameter 818 of the central bore 808 is selected so that the extensions 804 have to bend to fit. In one embodiment, the diameter 818 of the central bore is less than or substantially equal to the size 814 of the opening 812 in the annulus 810. Therefore, the plug 800 can easily pass from the central bore 808 through the opening 812, and the opening 812 holds the extensions 804 in the folded position until the extensions pass the interior surface 816 of the annulus 810. In another embodiment, the diameter 820 of the cannula is less than the size 814 of the central bore 808. Therefore, the cannula can be inserted fully through the opening 812 to the interior surface 816 of the annulus 810, and the central bore 808 holds the extensions 804 in the folded position until the extensions pass the interior surface 816 of the annulus 810. The opening 812 can be cut or formed to be of a desired size and shape to accept the plug 800 and the cannula 806.

The plug 800 is advanced through the central bore 808 in the direction of arrow I, and the cannula 806 is brought adjacent the annulus 810. The plug 800 is pushed out from the central bore 808 until a leading pair of extensions 824 emerge from the opening, return to their natural state and engage an interior surface 816 of the annulus 810 (FIG. 37). These extensions 824, being made of flexible and resilient material, may bend slightly in accordance with the curvature of the interior surface 816. The cannula 806 is then pulled away from the annulus 810, pulling the plug 800 from the central bore 808. The trailing extensions 826, after emerging from the central bore 808, return to their natural state and engage an exterior surface 822 of the annulus 810 (FIG. 38). These extensions 826, being made of flexible and resilient material, may bend slightly in accordance with the curvature of the interior surface 822. The length of the main body 802 is selected such that the leading and trailing extensions remain in contact with the interior and exterior surfaces of the annulus, holding the plug in the desired position. The extensions may also be stitched or sutured to the annulus, and a second flowable plug material can also be used in combination with this plug 800.

Figure 39:
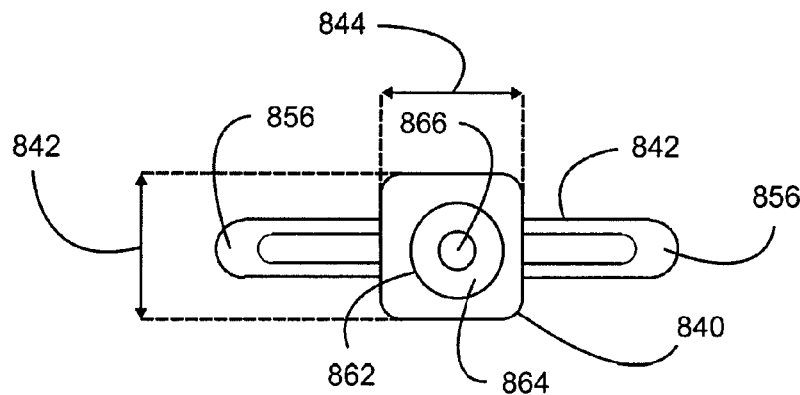
FIG. 39 is a representation of another embodiment of a flexible plug and an anchor plate in accordance with the present invention.
Figure 40:
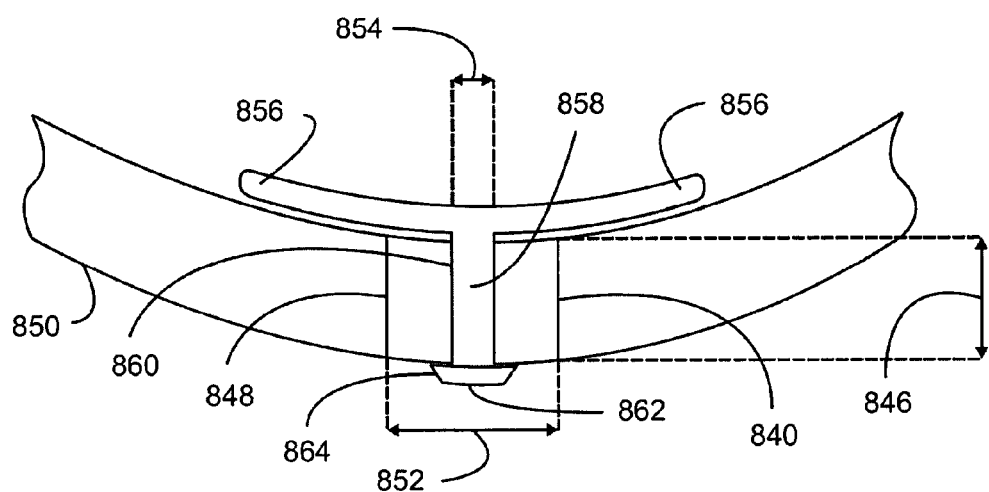
FIG. 40 is a schematic representation of the plug and anchor plate of FIG. 39 disposed in an annulus opening.

Referring to FIGS. 39-40, another embodiment of the soft tissue repair system of the present invention using a plug is illustrated. In this embodiment, a plug 840 is constructed of PCU or collagen Type I. The plug preferably has a square profile with equal height 842 and width 844. The depth 846 is selected based on the thickness of the opening 848 in the annulus 850 that is to be repaired. In one embodiment, a plurality of plugs 840 is provided, each one having one of a plurality of square dimensions, for example 2 mm×2 mm, 4 mm×4 mm, 6 mm×6 mm and 8 mm×8 mm, among others. The specific size of the plug is selected based on the width 852 of the opening 848. In one embodiment, the opening 848 is cut to a known size that corresponds to one of the available sizes of the plug 840. In order to repair the opening 848, the appropriately sized plug 840 is inserted into the opening 848.

Although the plug 840 can be sewn to the annulus 850 to secure it in the opening, preferably an interior patch or anchor 842 is used to anchor the plug 840 in the opening 848. In one embodiment, the interior patch 842 is formed from a resorbable material. The interior patch 842 includes a pair of opposing arms 856, a stem portion 858 extending perpendicularly from the opposing arms 856 and a collar 862 on an end of the stem portion 858 opposite the opposing arms. The distance between the opposing arms 856 and collar 862 is set based on the depth 846 of the plug 840. The plug 840 includes a central hole 860 that is of sufficient width 854 to accommodate the stem 858 of the interior patch 842. The interior patch 842 is passed through the opening 848 in the annulus 850 until the opposing arms 856 are disposed in the interior of the annulus 850. The stem portion 858 extends back through the opening 848, and the appropriately sized plug 840 is pushed over the collar 862, into the opening 848 and onto the stem 858. The collar includes a beveled leading edge 864 to assist in the insertion of the stem portion 858 into the hole 860 in the plug 840. The force between the plug 840 and the opening 848 in combination with the opposing arms 856 anchors the plug 840 in the opening 848. In one embodiment, the stem 858 is sized larger than the size 854 of the hole 860 in the plug 840, causing the plug 840 to expand slightly and increasing the frictional force between the plug 840 and the opening 848. In addition, the plug 840 can be stitched or sewn to the annulus. In one embodiment, this plug 840 is used in combination with a second flowable plug material, and the flowable plug material can be passed through a central opening 866 in the stem 862 to the interior of the annulus 850.

Figure 41:
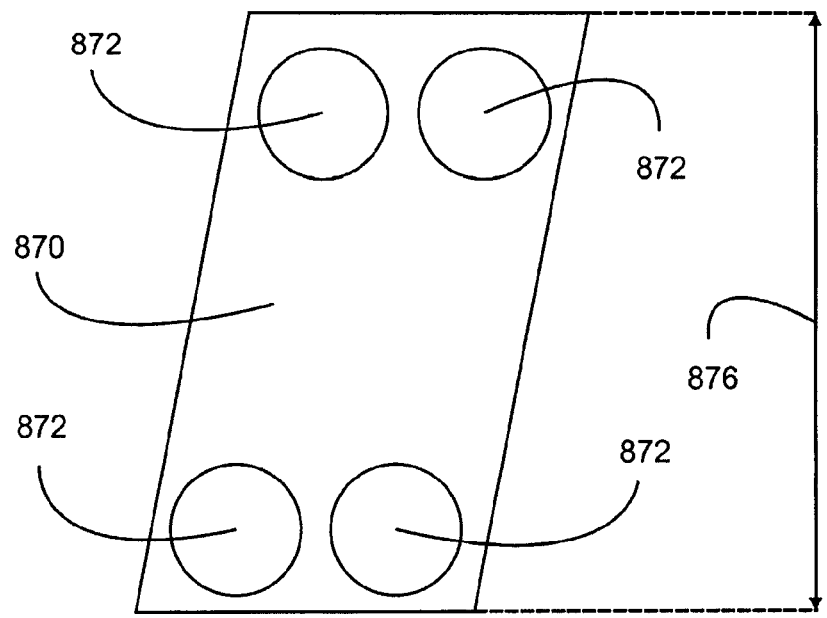
FIG. 41 is a representation of an embodiment of a plate for use with embodiments of plugs in accordance with the present invention.
Figure 42:
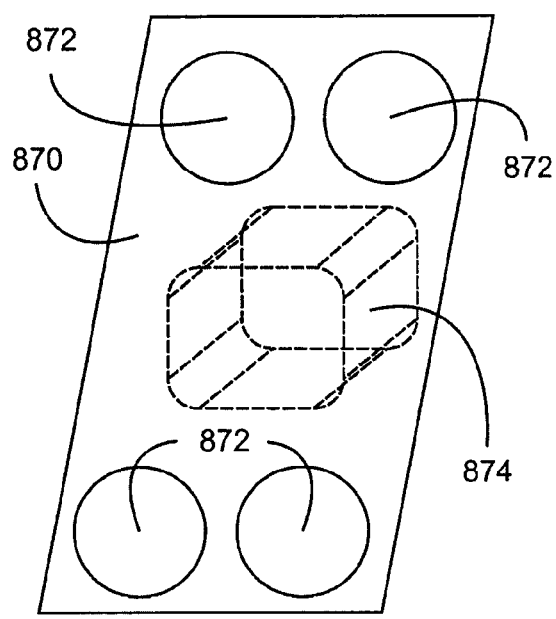
FIG. 42 is a representation of the plate of FIG. 41 in combination with an embodiment of a flexible plug.
Figure 43:
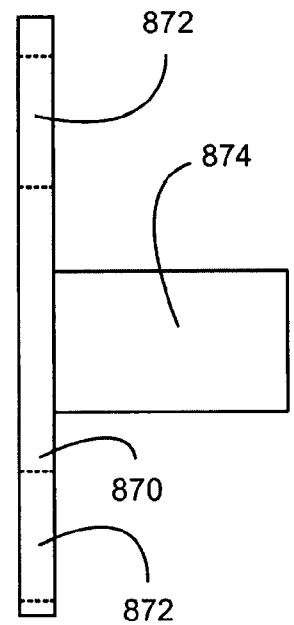
FIG. 43 is a representation of a side view of the flexible plug and plate of FIG. 42.
Figure 44A:
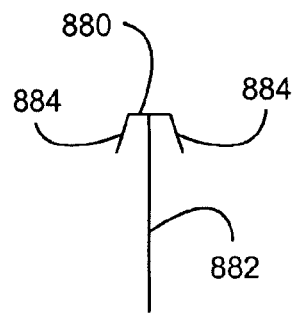
FIG. 44*a* is a schematic representation of another embodiment of a cover-type plug in accordance with the present invention in a folded position.
Figure 44B:
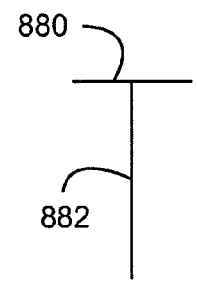
FIG. 44*b* is a schematic representation of the cover-type plug of FIG. 44*a* in an unfolded position.

Referring to FIGS. 41-43, another embodiment of the soft tissue repair system of the present invention using a plug is illustrated. In this embodiment, a plate 870, i.e., a cover-type plug, is used in combination with a plug 864. The plate can be used in combination with any of the plug embodiments described herein. As illustrated, an elongated plug 874 having a generally rectangular cross-section is attached to one side of the plate 870. Alternatively, the plate can be independent of the plug, and the plug is inserted in the annulus opening separate from the plate. Suitable materials for the plate include titanium, elastomers and polymers. In one embodiment, the plate 870 is a rectangular plate and includes a plurality of holes 872 passing completely through the plate 870. These holes accommodate fasteners such as titanium screws and polymer screws. Although the plate can be attached to the annulus, preferably, the plate is secured by screws to the superior and inferior vertebral body of the annulus being repaired. In order to accommodate attachment to the vertebral body, the plate 870 has a length 876 that is sufficient to span the annulus and to extend sufficiently over the vertebral body. This prevents expulsion of the plug from the annulus. Therefore, the plug is placed in the annulus opening, and the plate, positioned over the plug, is fastened to the adjacent vertebral body.

Referring to FIGS. 44a, 44b, 45a and 45b, another embodiment of the soft tissue repair system of the present invention using a plug is illustrated. In this embodiment, two cap-type or covering-type plugs are used to cover the interior and exterior of the opening in the annulus. The interior cap-type plug 880 includes a pair of opposing wings 884 that can be bent or flexed so that the plug 880 can be passed through a cannula and through the opening in the annulus. An inserter rod 882 is attached to the plug 880. Suitable attachment mechanisms include, but are not limited to frangible attachments and releasable attachments such as threaded attachments. In one embodiment, the inserter rod 882 is fixedly and non-releasably attached to the plug 880. Once the plug 880 is passed through an opening in the annulus and into the interior of the annulus, the wings 884 extend outward (FIG. 44b), for example under the force of their inherent resiliency, and engage an interior surface of the annulus. The wings 884 can also be forced open using a push rod or push collar associated with the inserter rod 880.

Figure 45A:
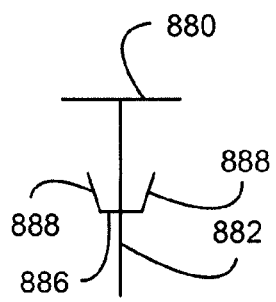
FIG. 45*a* is a schematic representation of another embodiment of a cover-type plug in a folded position in combination with the cover-type plug of FIG. 44*a*.
Figure 45B:
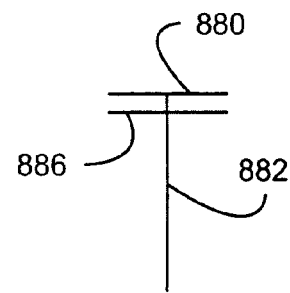
FIG. 45b is a schematic representation of the combination of cover-type plugs of FIG. 45a with both plugs in an unfolded position.

An exterior cap-type plug 886 having a pair of opposing wings 888 is then passed along the inserter rod 882 (FIG. 45a). The exterior plug 886 includes a center hole to accommodate the inserter rod 882. The opposing wings 888 are bend forward toward the annulus. Therefore, as the exterior plug 886 is brought into contact with the annulus, the opposing wings expand and contact the exterior surface of the annulus. Alternatively, the opposing wings 888 are held in the bent position by a cannula and expand to a natural position under the force of their inherent resiliency as they emerge from the cannula. Once both the interior and exterior plugs are in position (FIG. 45b), they sandwich the annulus, closing both sides of the opening. Both plugs can be sewn to the annulus. In one embodiment, the inserter rod passes from the interior plug 880 through the exterior plug 886, engaging the exterior plug in a locking arrangement. Therefore, the inserter rod can be clipped at the exterior plug, and the remaining portion of the inserter rod holds the interior and exterior plugs together.

Figure 46:
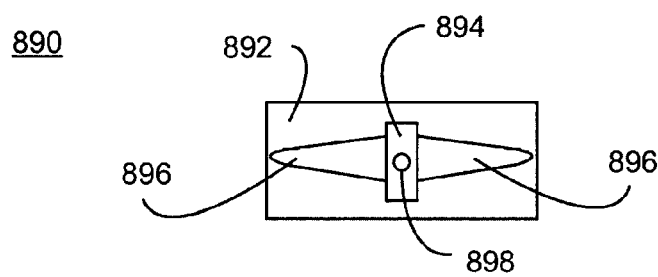
FIG. 46 is a representation of another embodiment of a plug in accordance with the present invention.

Referring to FIG. 46, an exemplary embodiment of a plug 890 that can be used as either an interior or exterior cap-type plug is illustrated. The plug includes a main body 892 formed as a small sheet of an elastomeric or polymeric material. In one embodiment, the main body 892 is formed of a material that can be sewn to the annulus. In general, the material of the main body 892 has sufficient strength to prevent the nucleus pulposus from being expelled through the opening and to prevent plug material within the opening from being expelled. The main body 892 is of a sufficient size to completely cover the opening and can be any desired shape including rectangular, square, circular, oblong or a custom shape.

At least one opposing pair of flexible resilient members 896 attached to the main body 892 extend from a central support member 894 that is also attached to the main body 892. In one embodiment, the two resilient members 896 are mirror images of each other and extend in opposite directions across the main body 892. In one embodiment, the pair of resilient members 896 has a resting or natural position that holds the main body in a flat position. When a flexing force is applied to the resilient members, the resilient members bend, causing the main body to bend accordingly. However, the resilient members 896 return to their natural position when the flexing force is no longer applied. Suitable materials for the resilient members 896 and the support member 894 include, but are not limited to, metals such as titanium. In one embodiment, a stem 898 extends from the support member 894 in a direction perpendicular to the support member 894 and the main body 892. The stem 898 is constructed from the same material as the main body 890. The stem 898 provides a point of attachment for an inserter rod and can include threads to provide a screw-type attachment. In another embodiment, the support member 894 includes a central hole in place of the stem. Therefore, an inserter rod can be passed through the central hole.

Figure 47:
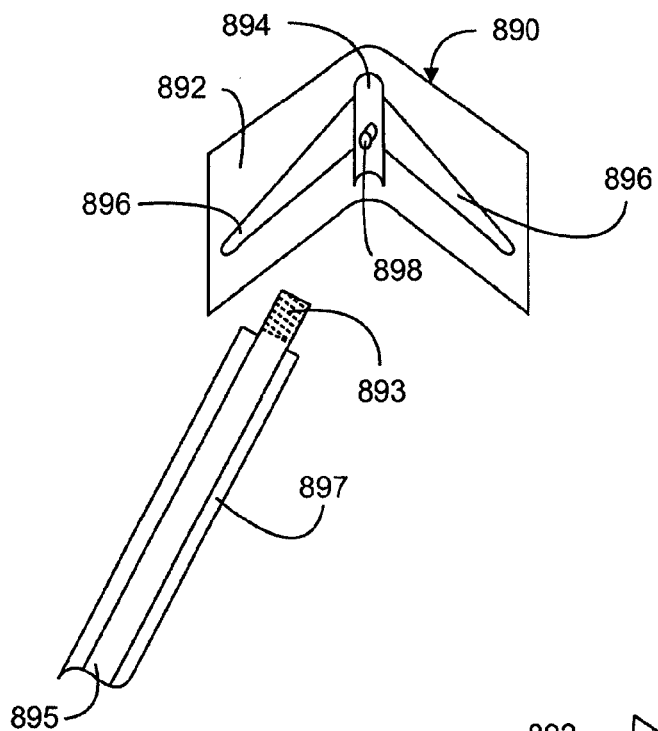
FIG. 47 is a representation of the plug of FIG. 46 with an embodiment of an inserter rod and cannula.
Figure 48:
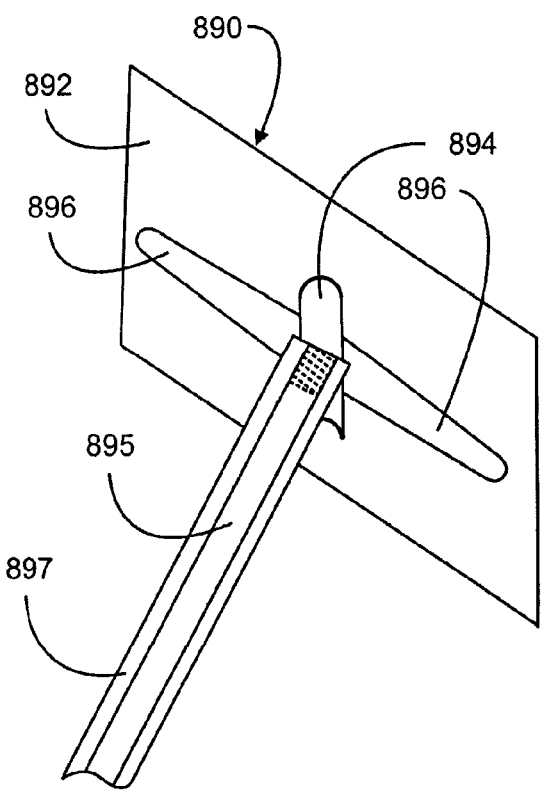
FIG. 48 is the representation of the plug, inserter rod and cannula of FIG. 47 with the inserter rod attached to the plug.

Referring to FIGS. 47 and 48, and embodiment of the plug 890 is illustrated where the resilient members 896 have a resting or natural position that is curved. In addition, the support member 894 can have a corresponding curvature. The main body 892 follows the resting curvature of the resilient members 896. An inserter rod 895 having a threaded end 893 is provided inside a hollow tube or cannula 897. The inserter rod 895 can move within the cannula 897. With the threaded end 893 of the inserter rod 895 extending from the cannula 897, the threaded end 893 is threaded onto the stem 898. The inserter rod 895 can then be used to position the plug 890 adjacent an annulus opening or to push the plug 890 through the annulus opening. By pushing the cannula toward the plug 890 and engaging the support member 894 and the resilient members 896 with the cannula, the plug 890 is moved to a flat position (FIG. 48) that is used to engage either the interior or exterior surface of the annulus.

Figure 49:
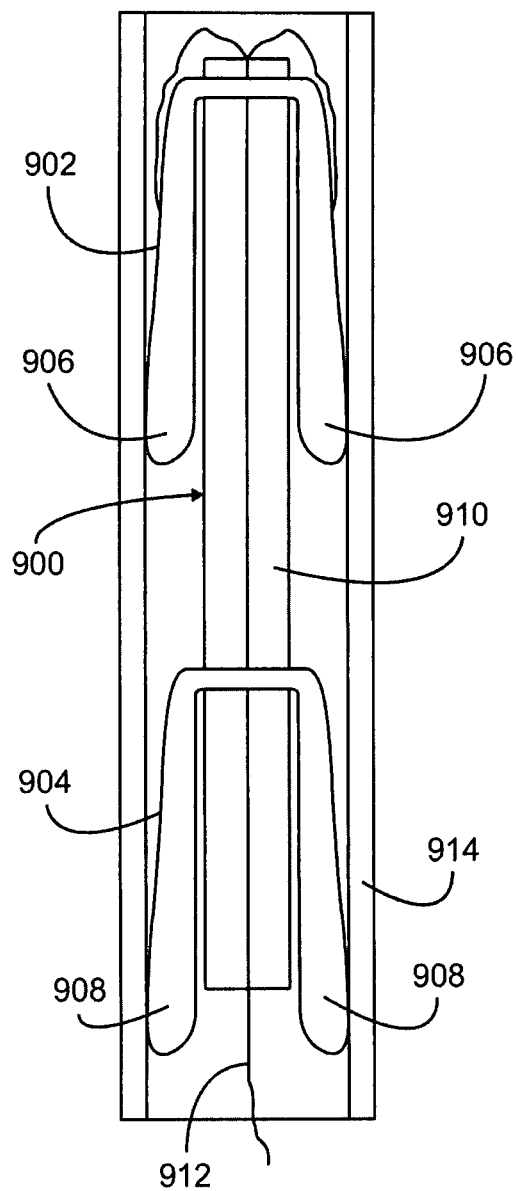
FIG. 49 is a representation of another embodiment of a flexible plug disposed within a cannula in accordance with the present invention.
Figure 50:
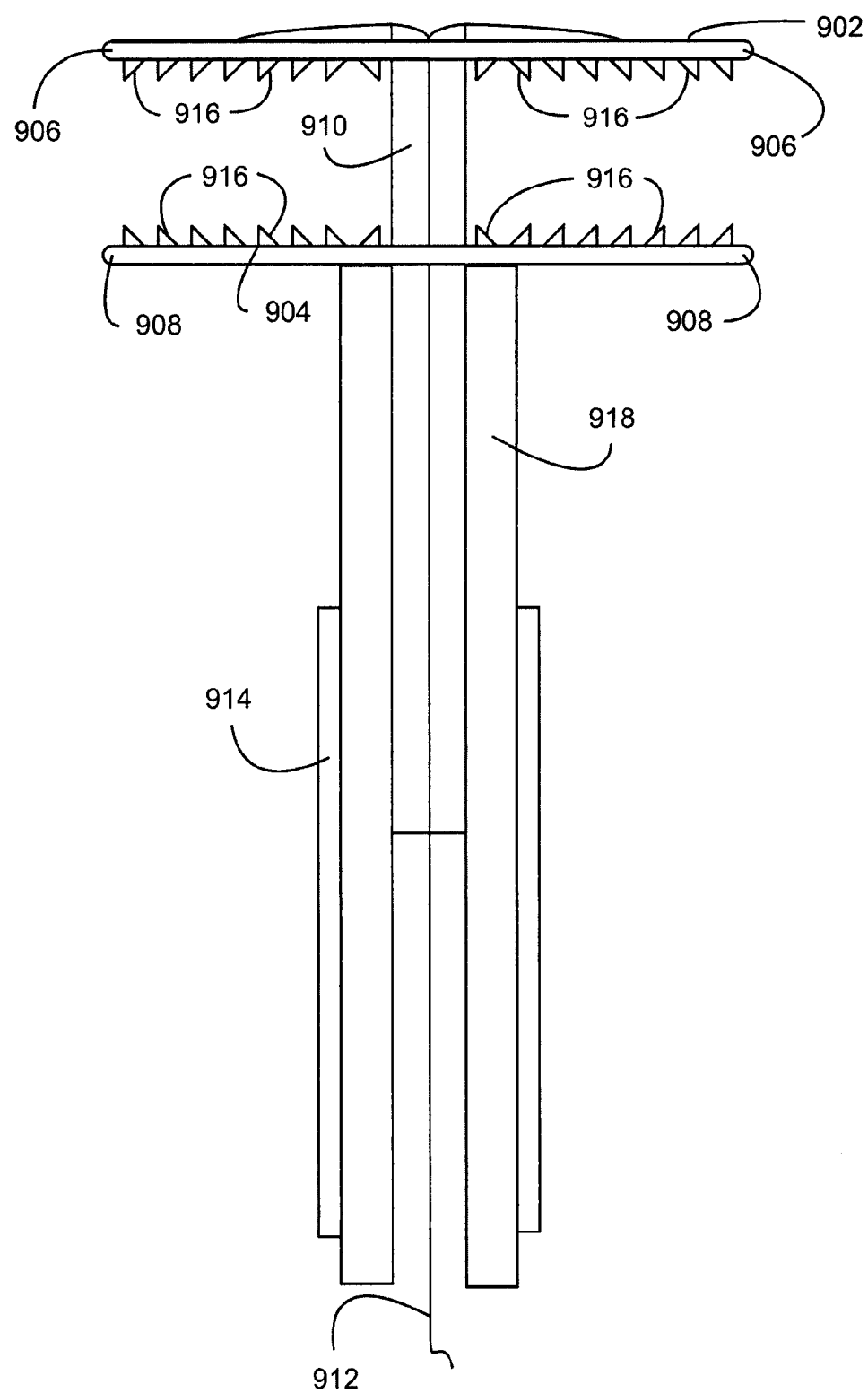
FIG. 50 is a representation of the flexible plug of FIG. 49 deployed out from the cannula.
Figure 51:
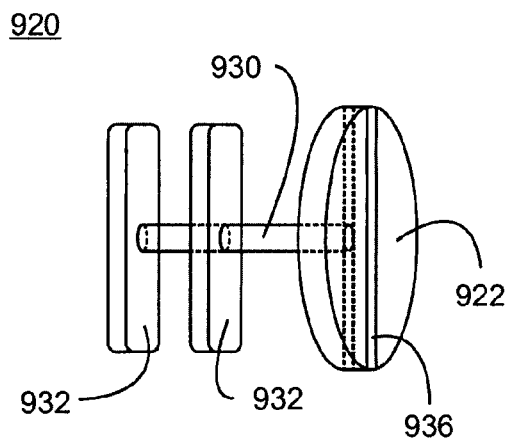
FIG. 51 is a representation of another embodiment of a plug in accordance with the present invention in an initial position for insertion into an annulus opening.

Referring to FIGS. 49-50, another embodiment of the soft tissue repair system of the present invention using a plug is illustrated. In this embodiment, cap-type plugs are used in combination with a clamping mechanism such that the opening in the annulus is disposed or clamped between two cap-type plugs disposed on the interior and exterior of the annulus opening. The system of this embodiment includes a first cap-type plug 902 having a pair of opposing, flexible and deployable wings 906. In one embodiment, the first cap-type plug 902 is fixed to a central shaft 910. The system also includes a second cap-type plug 904 having a pair of opposing, flexible and deployable wings 908. In one embodiment, the second cap-type plug 904 is attached to the central shaft 910 and can slide along the central shaft 910. The opposing wings can also be arranged as a flexible flange or collar that extends completely around the central shaft 910. A wire or thread 912 running through the central shaft 910 is as attached to both of the opposing wings 906 of the first plug 902. A cannula 914 is provided for deploying the system, and both plugs and the central shaft are initially located within the cannula 914. The opposing wings of both plugs are bent toward the central shaft in order to fit within the cannula. The thread 912 extends out from the cannula.

The central shaft is placed adjacent or inserted through an opening in an annulus, and the central shaft 910 and plugs are advanced through the cannula 914 until the first plug 902 emerges from the cannula 914 into the interior of an annulus. The first plug 902 becomes the interior plug. In one embodiment, the thread 912 is pulled to open the opposing wings 906. Alternatively, the opposing wings 906 spring to a natural or resting position that is generally perpendicular to the central shaft 910 as they emerge from the cannula 914. The central shaft 914 and second plug 904 continue to advance from the cannula 914 until the second plug emerges from the cannula 914 adjacent the annulus opening on the exterior of the annulus. The second plug 904 becomes the exterior plug. In one embodiment, the opposing wings 908 spring to a natural or resting position that is generally perpendicular to the central shaft 910 as they emerge from the cannula 914. Alternatively, the opposing wings 908 are pushed to an extended position using a pushing tool 918 that is inserted through the cannula 914 and over the central shaft 910.

To clamp the plugs over the opening, the pushing tool 918 is pushed out from the cannula 914 and the thread 912 is pulled back through the cannula 914, drawing the first plug 902 toward the second plug 904 and clamping the annulus there between. In one embodiment, the first and second plugs include spikes or stabilizers 916 along their opposing wings that anchor into the annulus and further stabilize and clamp the plugs to the annulus. The cannula is removed and the extra length of central shaft is removed. The thread is tied to hold the plugs in the clamped position. In addition, there can be a ratcheted mechanism between the central shaft 910 and the second plug 908 to hold the plugs in the clamped position as the second plug 908 slides or advances along the central shaft 910.

Figure 52:
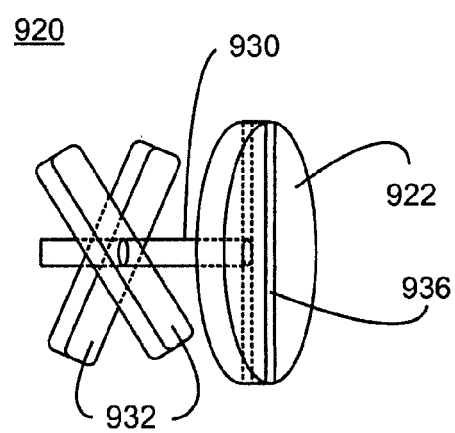
FIG. 52 is a representation of the plug of FIG. 51 in a second position for retention within the annulus opening.
Figure 53:
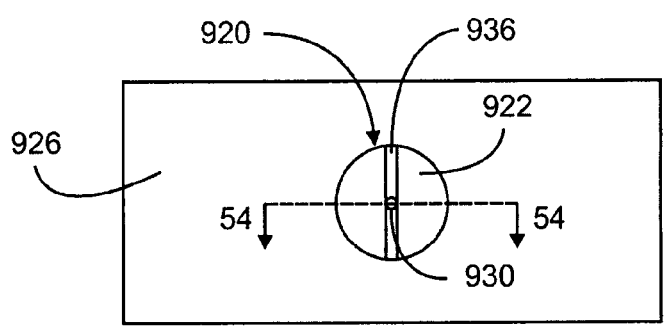
FIG. 53 is a representation of the plug of FIG. 51 disposed in an annulus opening as viewed from the exterior surface of the annulus.
Figure 54:
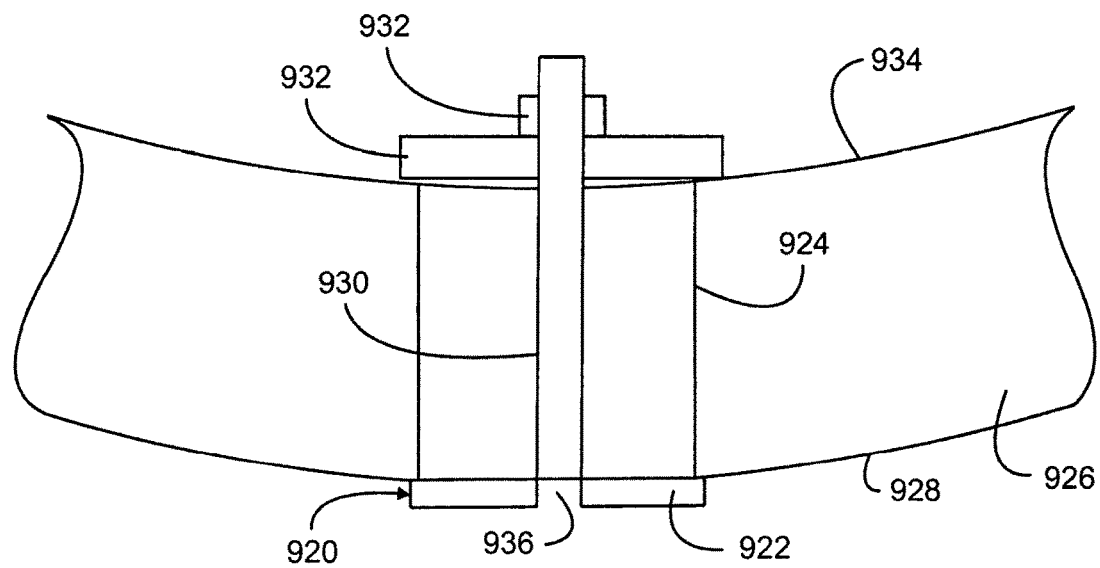
FIG. 54 is a view through line 54-54 of FIG. 53.

Referring to FIGS. 51-54, another embodiment of the soft tissue repair system of the present invention using a plug is illustrated. In this embodiment, a cover or cap-type plug is used in combination with a clamping mechanism such that the opening in the annulus is sealed with an exterior cap that is clamped to the annulus. In one embodiment, the clamping plug 920 includes a cap-type plug 922. The cap-type plug 922 is sized to cover an opening 924 in an annulus 926, and will be disposed on the exterior 928 of the annulus 924. In one embodiment, cap-type plug is circular or disc shaped. A shaft 930 extends from the cap-type plug 922. Attached to the shaft 930 and spaced from the cap-type plug 922 is a pair of anchor bars 932. The anchor bars 932 extend perpendicularly from the shaft 930 and are initially aligned with each other. In this aligned position, the anchor bars pass 932 pass through the opening 924. After passing through the opening 924, the cap-type plug 922 is rotated, which initially rotates the anchor bars 932 in opposite directions until the bars form an "X" (FIG. 52). In one embodiment, the anchor bars 932 are perpendicular to each other in the "X" position. In this position, the anchor bars 932 will not pass back through the opening 924.

In one embodiment, the anchor bars 932, following the initial rotation of the cap-type plug 922, lock in the "X" position. Continued rotation of the cap-type plug 922 draws the anchor plugs 932 toward the cap-type plug 922, clamping the annulus 926 between the two. In one embodiment, the shaft 930 extends through the anchor bars 932 and into the interior of the annulus 926. In one embodiment, the cap-type plug 922 includes a key hole or slot 936 to accept a tool (not shown) for rotating the cap-type plug 922.

Figure 55:
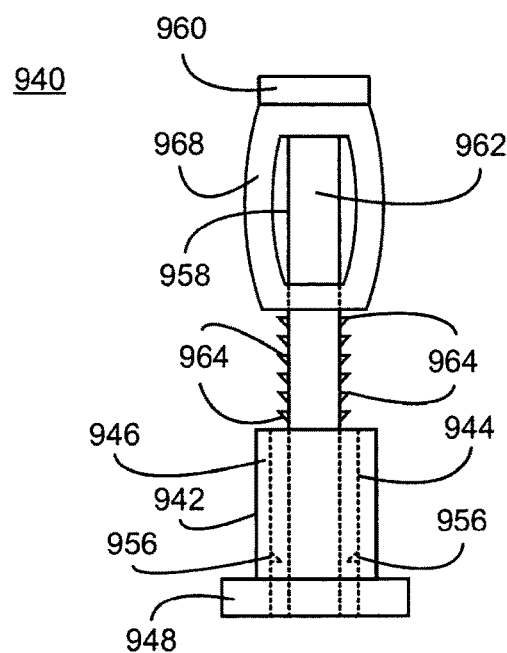
FIG. 55 is a representation of another embodiment of a plug with a clamping mechanism in accordance with the present invention in an initial position for insertion in an annulus opening.

Referring to FIGS. 55-57, another embodiment of the soft tissue repair system of the present invention using a plug is illustrated. In this embodiment, a plug and clamping mechanism 940 is used. The plug and clamping mechanism 940 includes a plug body 942 having an insert portion 946 sized and shaped to fit into the opening 950 in the annulus 952. The plug body 942 also includes an enlarged flange portion 948 that is attached to the insert portion 946 and that is of sufficient size to not pass through the opening. In one embodiment, the insert portion 946 is cylindrical and includes a hollow interior 944, and the flange portion 948 is a circular flange. The flange portion 948 engages the exterior surface 954 of the annulus 952. At least one and preferable a plurality of tangs 956 extend into the hollow interior 944.

The plug and clamping mechanism 940 also includes a clamping pin 958 having a head 960 and a body 962. The body 962 extends through the hollow interior 944 and includes a plurality of grooves or nubs 964 that engage the tangs 956 in the hollow interior 944. Therefore, as the body 962 is advanced through the hollow interior 944, the tangs 956 in the hollow interior 944 engage the nubs 964 on the body 962 and hold or lock the clamping pin 958 in the hollow interior 944. Disposed around the body 962 of the clamping pin 958 between the head 960 and the plug body 946 is a compression anchor 968. The compression anchor in an initial state (FIG. 55) is sized to pass through the opening 950 in the annulus 952. Once inside the annulus, the body 962 of the clamping pin 958 is pulled through the hollow interior 944, and the compression anchor 968 is squeezed between the head 960 and the plug body 946. This squeezing force moves the compression anchor 968 to an expanded state. In this expanded state, the compression anchor 968 is in contact with the interior surface 972 of the annulus 952 and has a size that is greater than the opening 950 in the annulus 952. This secures the plug and clamping mechanism 940 in the annulus opening.

Figure 59:
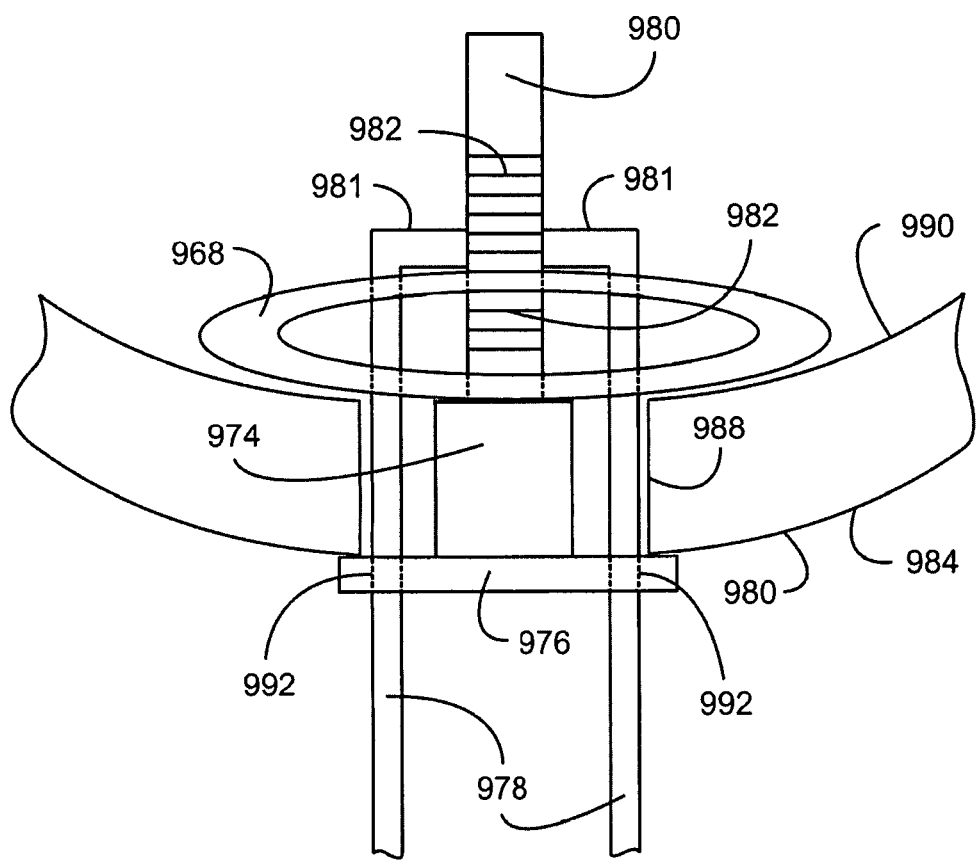
FIG. 59 is a schematic representation of the plug with clamping mechanism of FIG. 58 disposed in the annulus opening in a clamped position.

The compression anchor includes slots 970 on either side that facilitate the bending of the sides and the expansion of the compression anchor 968. In addition, these slots 970 facilitate the used of the compression anchor in another embodiment of the plug and clamping mechanism as illustrated in FIGS. 58 and 59. In this embodiment, the plug body 972 includes an insertion portion 974 with an enlarged flange portion 976 attached to one end and a ribbed extension 980 attached to the other end. Again, the flange portion 976 is sized and shaped to be larger than the opening 988 in the annulus 984 and to engage the exterior surface 986 of the annulus 984. The ribbed extension 980 includes a plurality a parallel ribs 982 running along the length of the extension 980.

A pair of compressing arms 978 passes through slots 992 in the flange portion and run along the body portion 974 and the extension 980. Each compressing arm 978 includes an end portion 981 that runs generally parallel to the flange portion 976 and contacts the extension 980. The compression anchor 968 is disposed between the body portion 974 and the end portions 981 of the compressing arms such that the extension 980 passes through the center of the compression anchor 968. The body portion 974, compressing arms 978 and compression anchor 968 are sized to pass through the opening 988 in the annulus 984 (FIG. 58).

Once the compression anchor 968 passes completely through the opening 988, the compressing arms 978 that extend through the flange portion 976 are pulled out through the flange portion 976. This pushes the end portions 981 on the compression anchor 968, compressing and expanding the compression fitting to a size greater than the opening 988. In this state, the compression anchor 968 is in contact with the interior surface 990 of the annulus 984 and the plug and clamping mechanism is anchored in the opening 988 of the annulus 984. The slots 970 in the compression anchor 968 accommodate the compressing arms 978 as the compression anchor 968 expands. Following expansion, the compressing arms 978 can be removed, for example by bending or rotating the arms to break a frangible connection and then removing the arms through the slots 992 in the flange portion 976. A second flowable plug material can also be used in combination with this embodiment, for example, by passing the flowable plug material through the slots 992 in the flange portion 976 after removal of the compressing arms.

Figure 61:
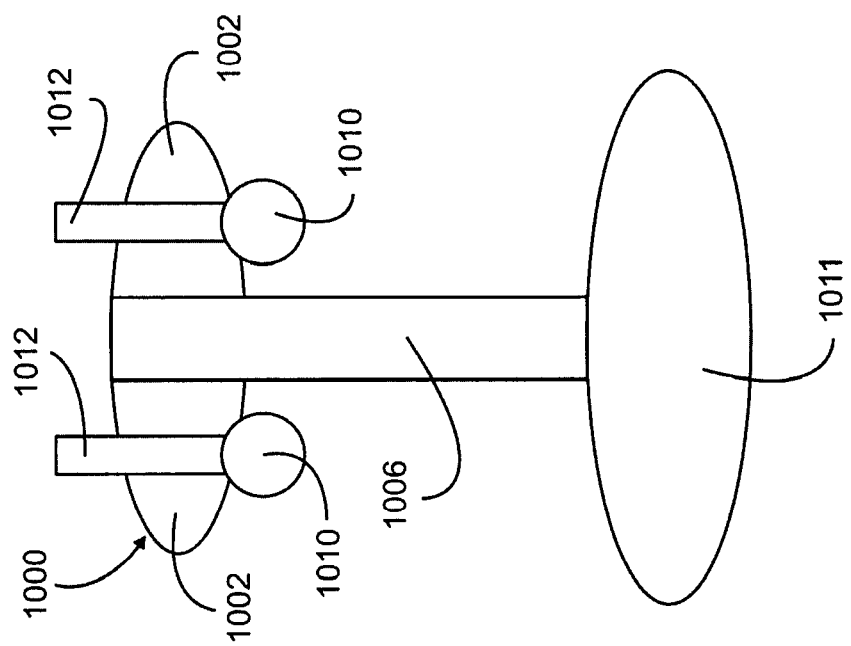
FIG. 61 is a representation of the plug of FIG. 60 in a second deployed position for retention in the annulus opening.
Figure 60:
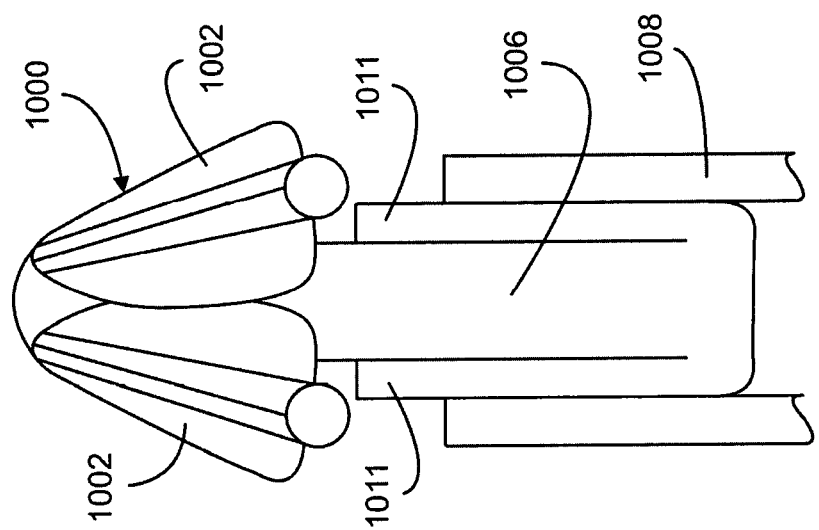
FIG. 60 is a representation of another embodiment of a flexible plug in accordance with the present invention in an initial position for insertion in an annulus opening.

Referring to FIGS. 60-61, another embodiment of the soft tissue repair system of the present invention using a plug is illustrated. In this embodiment, the plug 1000 includes an elongated stem or body 1006 having one or more opposing pairs of flexible extensions 1002 on one end. These pairs have a natural extended position (FIG. 61) and include rollers or wheels 1010 attached to rods 1012 mounted to each flexible extension 1002. An outer cap or seal 1011 is positioned on the opposite end of the body 1006. The seal 1011 is larger than the annulus opening that is being repaired. The seal 1011 and extensions 1002 can be folded against the body 1006 so that the plug 1000 can be passed through a cannula 1008. The cannula 1008 is passed through of brought adjacent to the annulus opening, and the plug is passes through the opening until the extensions pass into the interior of the annulus. The extensions 1002 spring to their natural position and the wheels rolls along the interior surface of the annulus. The seal 1011 passes out from the cannula 1008, expands, contacts the exterior surface of the annulus and seals the opening. Suitable materials for the plug 1000 include flexible and resilient materials.

Figure 62:
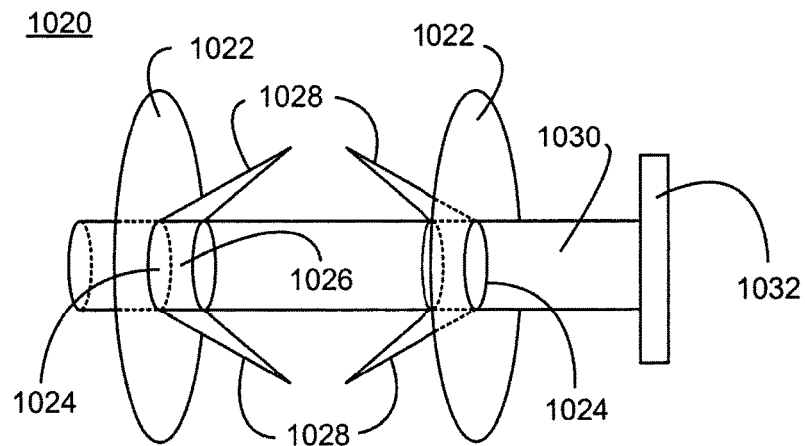
FIG. 62 is a representation an another embodiment of a plug with clamping mechanism and anchor barbs in accordance with the present invention.

Referring to FIG. 62, another embodiment of the soft tissue repair system of the present invention using a plug is illustrated. In this embodiment, cover or cap-type plugs are used in combination with a clamping mechanism and anchoring barbs such that the opening in the annulus is disposed or clamped between two cap-type plugs disposed on the interior and exterior of the annulus opening. The clamp and plug device 1020 of this embodiment includes a pair of cap-type plugs 1022. In one embodiment, each cap-type plug 1022 is disc-shaped and includes a central through hole 1024. The disc-shaped plug 1022 is of sufficient size to cover the opening in the annulus that is to be repaired. Surrounding each central through hole 1024 and extending from the plug 1022 is a collar 1026. At least one pair of barbs 1028 extend at an angle from each collar 1026. In one embodiment, each barb extends from its collar at an angle greater than 0 degrees and less than 90 degrees from the associated plug. Extending through the collar and central hole of each plug is a shaft 1030 having a handle 1032 at one end that facilitates turning of the shaft 1030. Preferably, the shaft 1030 is a threaded shaft, and the collars 1026 include internal threads. The internal threads in the collars 1026 have the appropriate left and right thread orientation so that rotation of the shaft handle 1032 draws the disc-shaped plugs 1022 together. As the plugs 1022 are drawn together, the barbs 1028 anchor into the annulus.

Figure 63:
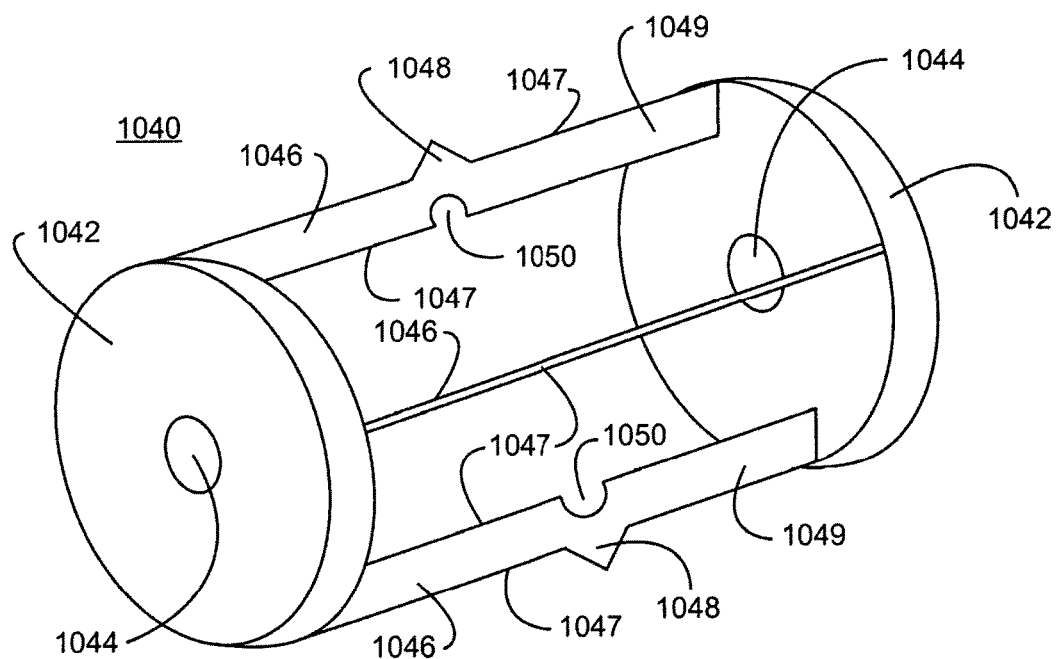
FIG. 63 is a representation of another embodiment of a plug as a collapsible cage in accordance with the present invention.
Figure 64:
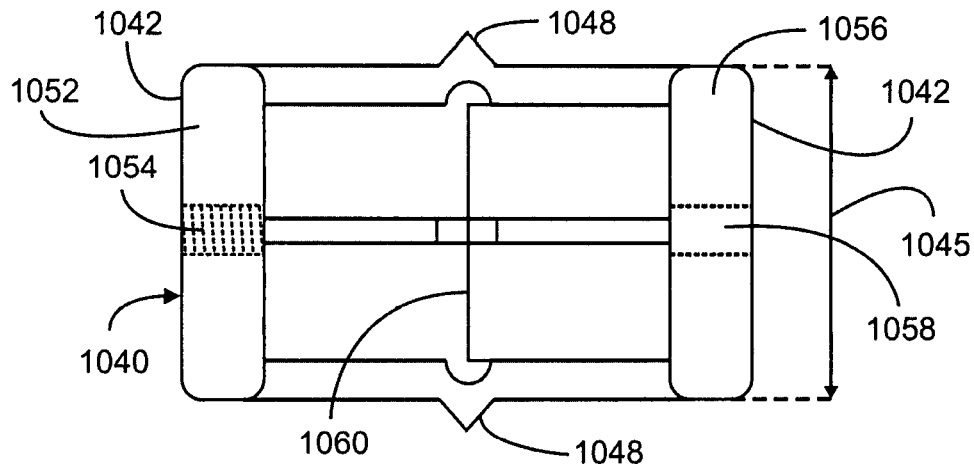
FIG. 64 is a representation of the plug of FIG. 63 in combination with an embodiment of a flowable plug material.
Figure 65:
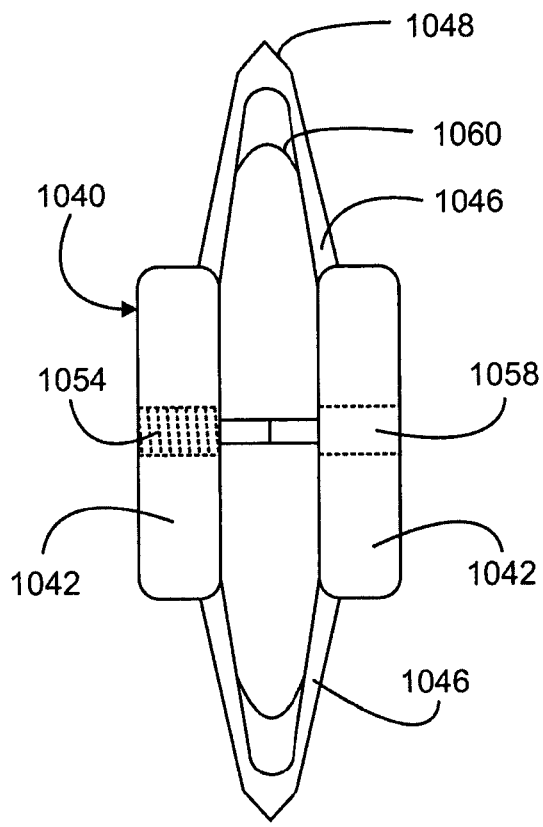
FIG. 65 is a representation of the plug and flowable plug material of FIG. 64 in a collapsed position.

Referring to FIGS. 63-65, another embodiment of the soft tissue repair system of the present invention using a plug is illustrated. In this embodiment, a plug 1040 is used to fill the opening in the annulus. The plug 1040 is configured as a collapsible cage and includes a pair of opposing ends 1042. Suitable materials for the collapsible cage include, but are not limited to titanium. In one embodiment, each opposing end 1042 is configured as a disc having a central hole 1044 passing completely through the disc. In one embodiment, each opposing end 1042 has a diameter 1045 that is less than the size of the annulus that is to be repaired; therefore, each opposing end 1042 will pass through the opening in the annulus. In one embodiment, the diameter is about 6 mm.

A plurality of arms 1046 extend between the opposing ends 1042 and are fixedly secured to the opposing ends. The plurality of arms 1046 are arranged as opposing pairs, and in one embodiment, the plug 1040 includes two opposing pairs of arms. Each arm is preferably a generally flat arm having opposing thin edges 1047 and opposing flat faces 1049. Each arm 1046 is positioned so that one of the thin edges 1047 runs along the outside of the plug 1040.

Along the length of each arm 1046 a spike 1048 extends out from the outside thin edge. Opposite each spike across the arm a notch 1050 extends inward from the inside thin edge. Preferably, the spike 1048 and notch 1050 are located about midway along the length of each arm. Each notch 1050 provides a breaking or bending point for its arm as the plug is compressed or collapsed (FIG. 65). As each arm bends outward at the notch when the plug is compressed, the spike 1048 forms a point, and this point can penetrate the annulus to anchor the plug 1040 in the annulus opening.

In one embodiment, the plug 1040 is compressed by drawing the two opposing ends 1042 together. In order to draw the two opposing ends together, a first one of the opposing ends 1052 has a threaded central hole 1054, and a second one of the opposing ends 1056 has a central hole without threads 1058. A threaded rod or conventional threaded bolt (not shown) can be passed through the central hole without threads 1058 and into the threaded central hole 1058 where it engages the threads. After the plug 1040 is inserted into an annulus opening, the threaded rod is turned, drawing the opposing ends together (FIG. 65). At the same time, each arm 1046 bends outward, enlarging the size of the plug 1040 beyond the diameter 1045 of the opposing ends. The arms engage the annulus and anchor the plug in the annulus opening.

In one embodiment, the plug 1040 also includes a second flowable plug material 1060 (FIG. 64) or a second flexible plug that is disposed within the arms 1046 of the plug 1040. Suitable materials for the flowable plug 1060 include, but are not limited to, PCU. In one embodiment, the flowable plug material 1060 fills approximately half the volume within the arms and is initially in contact with one of the opposing ends 1042. The flowable plug material has an initial cylindrical shape with a central opening (not shown) to accommodate the threaded rod. When the opposing ends 1042 are drawn together (FIG. 65), the flowable plug material 1060 is squeezed by both opposing ends and emerges from the plug 1040 to fill the interior space of the annulus opening. In one embodiment, additional flowable plug material can be inserted through the central holes 1044 in the opposing ends 1042 following compression of the plug 1040 and removal of the threaded rod.

Figure 69:
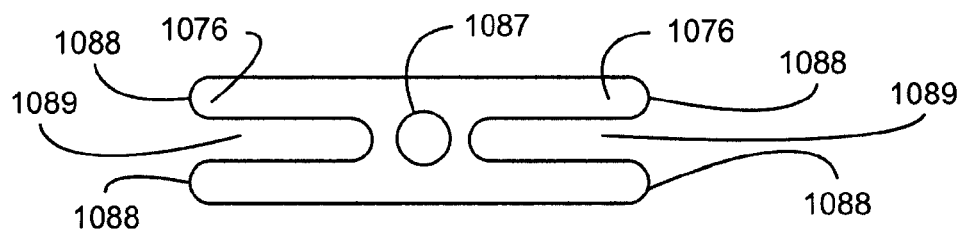
FIG. 69 is a representation of the plug and anchoring mechanism of FIG. 66 in an expanded position as viewed from an interior of an annulus.

Referring to FIG. 66-69, another embodiment of the soft tissue repair system of the present invention using a plug is illustrated. In this embodiment, the plug 1070 includes an expandable implant section 1072 and a separate keeper and expander section 1074. The implant section 1072 includes a neck 1075 having a central opening 1073 that passes completely through the neck 1075. The neck is sized to fit within an annulus opening. Extending from the neck 1075 and formed from a continuous band of material are a pair of expanding wings 1076. In one embodiment as illustrated in FIG. 69, each expanding wing 1076 is formed as a pair of separate wing prongs 1088 having a slot 1089 disposed between them. This provides for more flexibility in the exposing wings 1076, making expansion easier. Suitable materials for the implant section 1072 and the expander section 1074 include, but are not limited to, polyethylene, for example ultra high molecular weight polyethylene.

The keeper and expander section 1074 includes a head 1077 that is sized to be larger than the annulus opening that is to be repaired. In one embodiment, the head 1077 is a circular disc. Extending from the head 1077 is a keeper portion 1078 having a plurality of tangs or ridges 1082 running along its length. Extending from the keeper portion 1078 is an expander portion 1080. In one embodiment, the keeper portion 1078 and expander portion 1080 are both cylindrical, and the keeper portion 1078 is a larger cylinder than the expander portion 1080. This creates a shoulder 1079 at the transition between the keeper portion 1078 and the expander portion 1080.

An opening 1085 in an annulus 1083 is dilated, and the implant section 1072 in inserted through the opening 1085 until the expanding wings 1076 pass into the interior of the annulus 1083. The keeper and expander portion 1074 is passed through the central opening 1073 of the neck 1075, expanding the wings 1076 as described above. The expander portion 1074 is advanced until the head 1077 engages the exterior surface 1084 of the annulus, covering the opening, and the expanding wings 1076 engage the interior surface 1086 of the annulus 1083. The opening is sealed, and the plug 1070 is anchored in the opening 1085.

Referring to FIG. 67, the expander portion 1080 passes through the opening 1073 in the neck 1075 and a hole 1087 (FIG. 69) in the central portion 1081 between the expanding wings 1076. The expander portion 1080 is sized to pass completely through the hole 1087 in the central portion 1081, and the shoulder 1079 engages the central portion. Advancing the expander section 1074 further into the central opening 1073 moves the central portion 1081 in the direction of arrow J and the expanding wings 1076 in the direction of arrow P. As the keeper portion 1078 advances through the central opening 1073, the ridges 182 engage mating structures inside the central opening 1073, securing the keeper and expander section 1074 to the implant section 1072.

Figure 70:
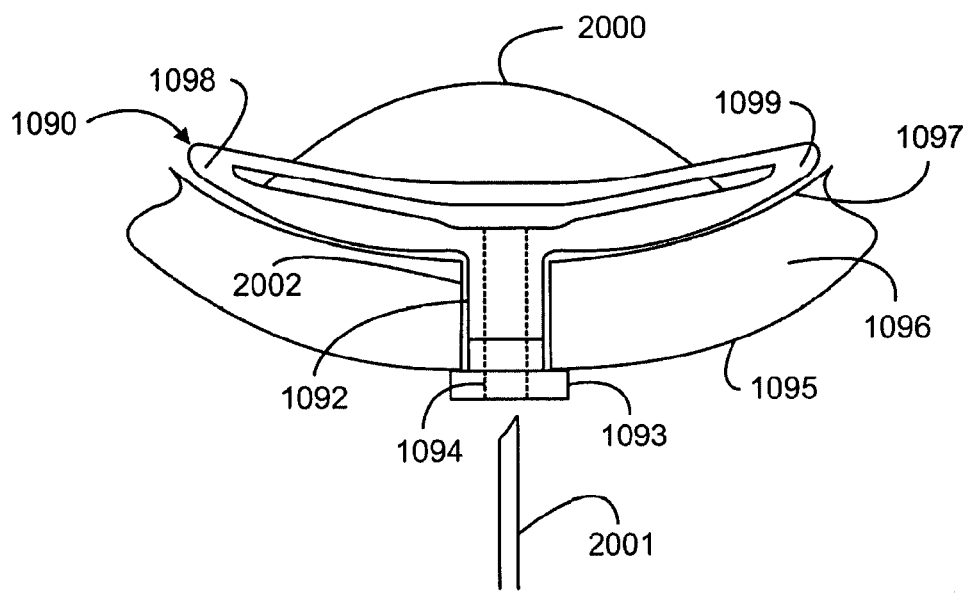
FIG. 70 is a representation of another embodiment of a plug and anchoring mechanism in combination with a flowable plug material and disposed in an annulus opening in accordance with the present invention.

In an alternative embodiment as illustrated in FIG. 70, a plug is used having an implant section 1090 with a neck 1092 sized to fit through the opening 2002 in the annulus 1096 and having a central hole 1094. The expanding wings 1098 extend from one end of the neck 1092, and an enlarged head 1093 is disposed on the other end of the neck 1092. The enlarged head 1093 has a size that is greater than the opening 2002 in the annulus 1096. Instead of the keeper and expander, a simple expander is used that does not engage or anchor itself within the central hole. Once the opening 2002 is dilated, the implant section 1090 is passed through the opening 2002 until the enlarged head 1093 engages the exterior surface 1095 of the annulus 1096. Then an expander is inserted through the central hole 1094 to move the expanding wings 1098 into contact with the interior surface 1097 of the annulus. The expander is removed, and a hollow tube or cannula 2001 is inserted through the central hole 1094 to introduce a flowable plug material 2000 that fills the voids between the plug and the opening as well as voids within the interior of the annulus.

Referring to FIGS. 71-75, another embodiment of the soft tissue repair system of the present invention using a plug is illustrated. In this embodiment, a flexible cover-type plug 2010 is used. The plug 2010 has a size and shape sufficient to cover an annulus opening, preferably from the interior of the annulus. Suitable shapes include, but are not limited to, circular, oval and rectangular. This cover-type plug 2010 is constructed from a sheet of flexible material 2011. The flexible material can be constructed as a thin sheet of mesh material, a thin sheet of woven material, a thin sheet of non-woven material (for example a thin sheet of biocompatible implant material similar to Tyvek® which is commercially available from E.I. du Pont de Nemours and Company of Wilmington, Del. and combinations thereof). In general, the flexible material is a plastic or polymer material.

Attached along the edge or perimeter of the flexible material 2011 is a resilient and flexible band 2012. The flexible band 2012 can be attached to the flexible material using fasteners or adhesives. In one embodiment, a small portion of the flexible material 2011 is folded over the flexible band 2012, covering the flexible band 2012 in the flexible material 2011. The overlapping flexible material 2011 is then sewn together to secure the flexible band 2012 within the folded flexible band 2012. The flexible band 2012 is formed in the desired shape of the plug 2010 and has sufficient resiliency to maintain the plug 2010 in that shape and sufficient flexibility to be twisted and bent. In one embodiment, the flexible band 2012 is titanium.

Figure 71:
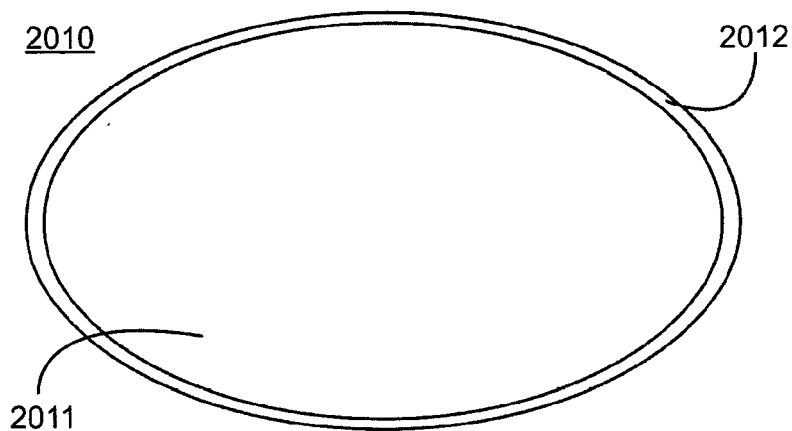
FIG. 71 is a representation of another embodiment of a cover-type plug in an expanded position in accordance with the present invention.
Figure 72:
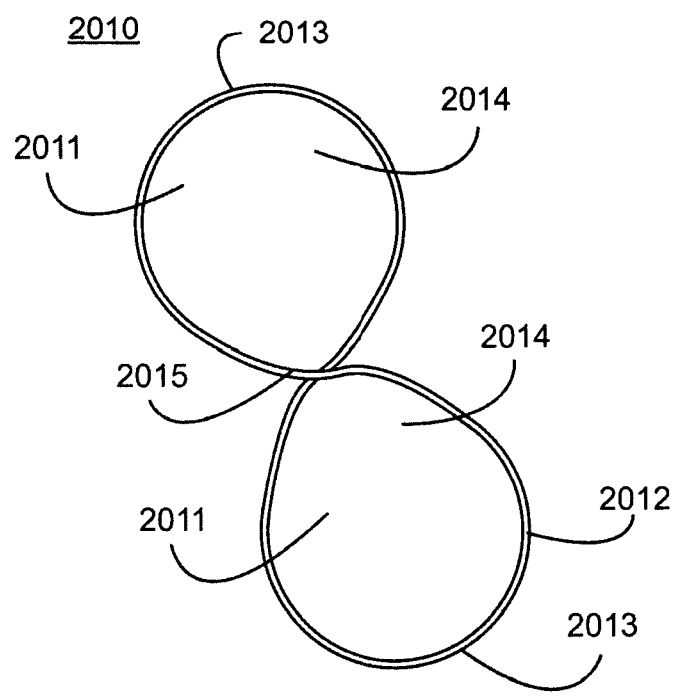
FIG. 72 is a representation of the cover-type plug of FIG. 71 in a partially folded position.
Figure 73:
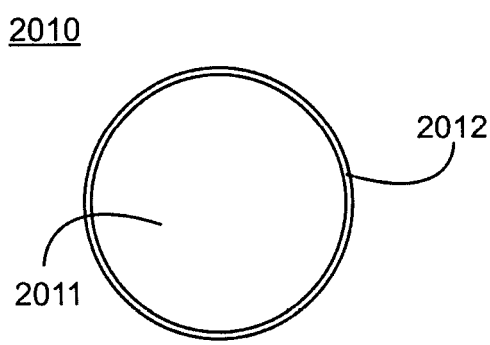
FIG. 73 is a representation of the cover-type plug of FIG. 71 in a partially fully position.

The plug 2010 has an expanded shape that is illustrated in FIG. 71. In this expanded shape, the plug 2010 is sized to cover an annulus opening. The plug 2010 will be located in the interior of the annulus in this expanded state; however, to insert the plug through the annulus opening to the annulus interior, the size of the plug 2010 is reduced by taking advantage of the flexibility of the plug 2010. As show in FIG. 72, opposite ends 2013 of the plug are grip and rotated in opposite directions to cross the flexible band 2012 in the middle. The two plug sections 2014 that are defined by the twisting action are folded onto each other about the point 2015 where the flexible band 2012 crosses itself. This results in a collapsed state (FIG. 73) for the plug 2010. Even in the collapsed state, the plug 2010 is flexible and can be twisted and rolled.

Figure 74:
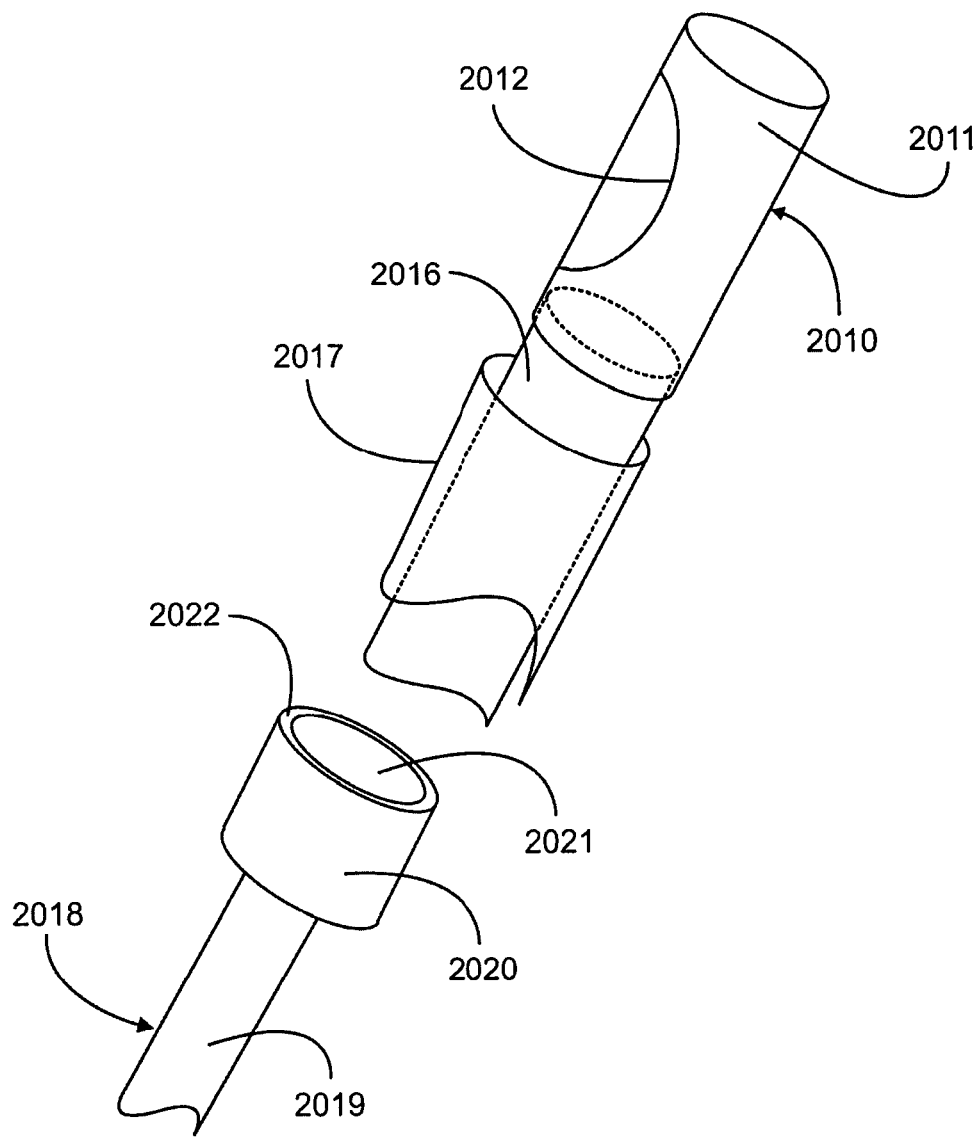
FIG. 74 is a representation of the cover-type plug of FIG. 71 folded, rolled and attached to an insertion mechanism.

As illustrated in FIG. 74, the plug 2010 in its collapsed state is rolled around a cylindrical installation shaft 2016. The rolled plug 2010 can slide along the length of the installation shaft 2016. In order to hold the plug 2010 in the rolled position, a cylindrical sheath 2017 is passed over the shaft 2016 and rolled plug 2010. The sheath 2017 houses the rolled plug 2010 and has a size small enough to pass through an annulus opening. In order to remove the rolled plug 2010 from the sheath 2017 and the installation shaft 2016, a pusher tool 2018 is provided. The pusher tool 2018 includes a cylindrical body 2019 that is aligned coaxial with the sheath 2017 and installation shaft 2016. Attached to an end of the cylindrical body 2019 is a cylindrical head 2020 having a circular opening 2010 with a diameter sufficient to facilitate passage of the installation shaft 2016 into the head 2020. The head 2020 passes between the installation shaft 2016 and the sheath 2017 until the leading edge 2022 of the head 2020 engages the rolled plug 2010, pushing the plug 2010 off of the installation shaft 2016.

Figure 75:
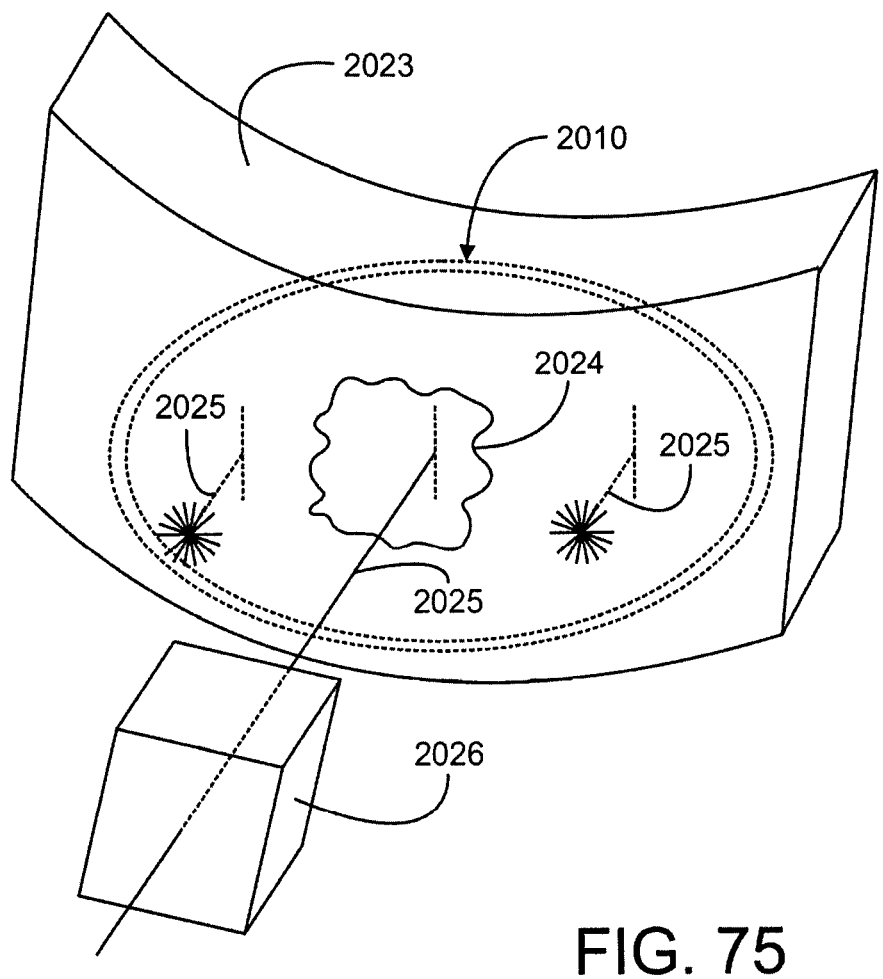
FIG. 75 is a representation of the cover-type plug of FIG. 71 expanded, inserted into the interior of an annulus and anchored to the annulus using sutures.

As shown in FIG. 75, once the plug 2010 is inserted through the opening 2024 in the annulus 2023, pushed from the installation shaft into the interior of the annulus 2023 and allowed to unroll and to return to its expanded resting state, the plug is positioned 2010 to cover the interior of the opening 2024. In one embodiment, the plug 2010 is then anchored to the annulus using a plurality of sutures 2025 that are tied to the plug 2010 at a plurality of locations, passed through the annulus 2023 and tied on the exterior of the annulus 2023. One suture passes through the opening 2025. This suture is passed through an extra block of plug material 2026 that is pushed into the opening 2024, and the suture is tied to hold the plug material 2026 in the opening. As an alternative to sutures or in combination with the sutures, darts or pins can be used. These darts or pins are passed through the annulus and anchored in the flexible material of the plug.

Figure 76:
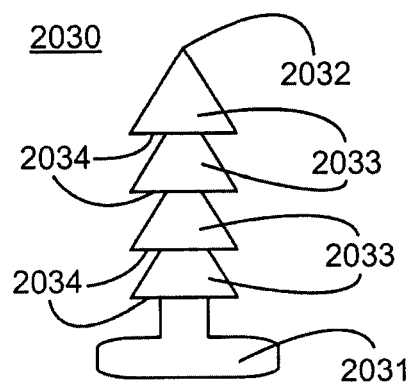
FIG. 76 is a representation of an embodiment of a dart to be used in anchoring the cover-type plug of FIG. 71 into an annulus.

Referring to FIG. 76, one embodiment of a pin 2030 for anchoring the flexible plug 2010 to the annulus 2023 is illustrated. The pin 2030 has an enlarged disc-like head 2031 on its proximal end. In one embodiment, the head 2031 is of sufficient size to not pass through the opening 2024 but to engage the exterior of the annulus and cover the opening. The pin 2030 is sized, with the exception of the head, to pass through the annulus opening. The distal end of the pin 2030 includes a point 2032 that can pierce the flexible material of the flexible plug 2010. A plurality of wedge-shaped portions 2033 run along the length of the pin 2030. These wedge-shaped portions 2033 allow the pin to pass through the flexible material and define a plurality of shoulders 2034 running around the pin 2030 that can engage and hold the flexible material.

Figure 77:
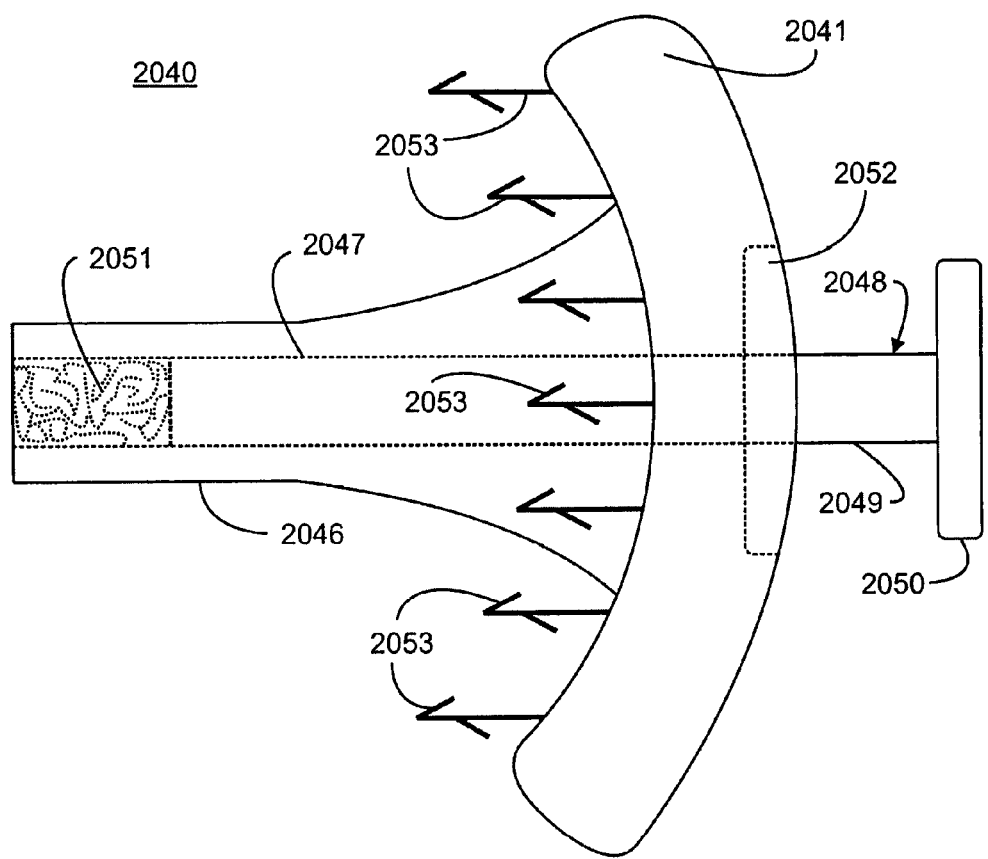
FIG. 77 is a representation of another embodiment of a plug with flowable plug material in a portion to be inserted into an annulus opening.
Figure 78:
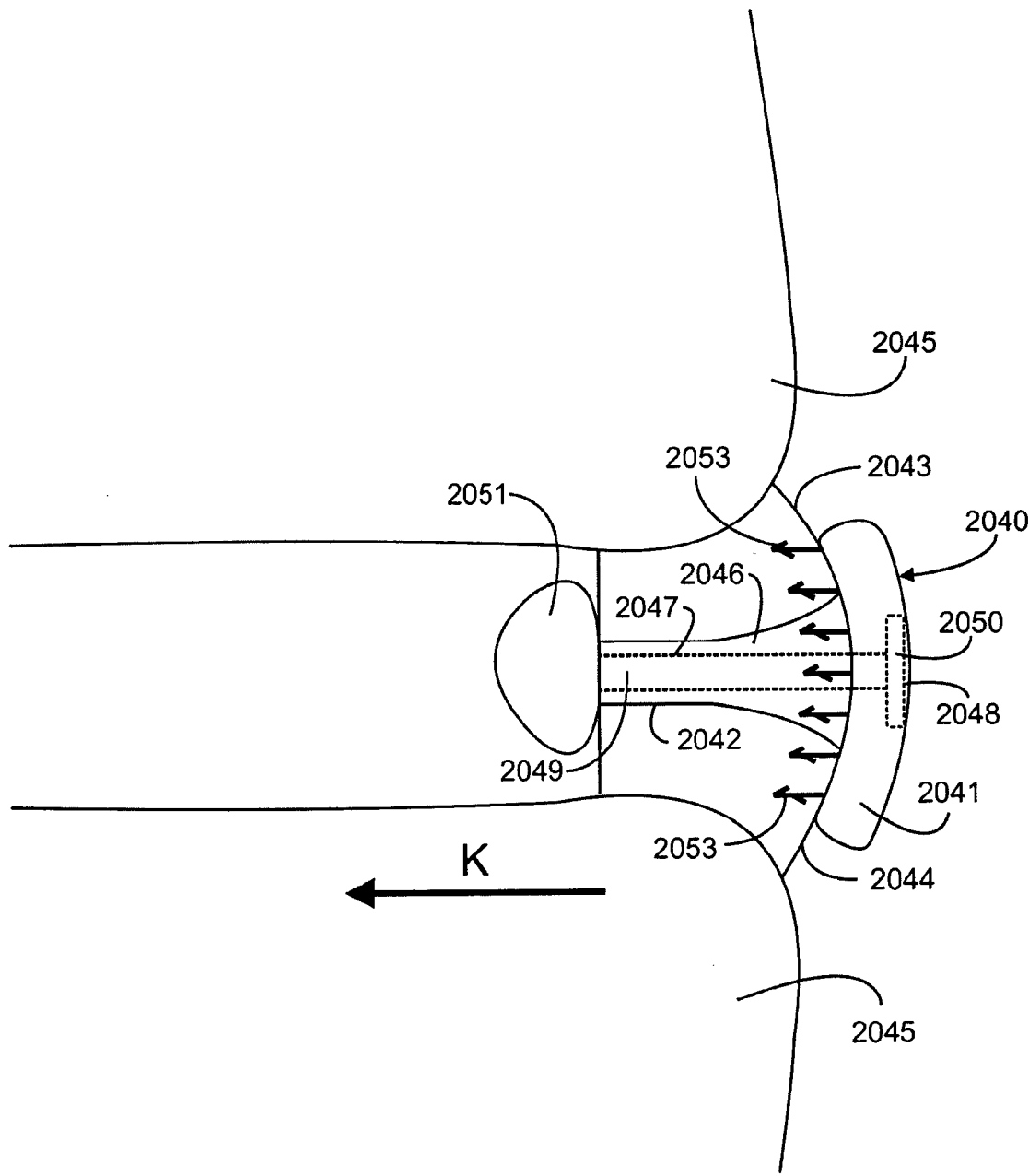
FIG. 78 is a representation of the plug of FIG. 77 disposed in an annulus opening with the flowable plug material expelled from the plug.

Referring to FIGS. 77-78, another embodiment of the soft tissue repair system of the present invention using a plug is illustrated. In this embodiment, a plug 2040 is provided that has a head portion 2041 sized to be larger than the opening 2042 in the annulus 2043 between two vertebral bodies 2045. The head portion 2041 is formed with a curvature that compliments and mates with the curvature of the exterior surface 2044 of the annulus 2043. A plurality of barbs 2053 are attached to and extend from the head portion 2041. The plug 2040 also includes a tapered body 2046 attached to and extending from the head 2041. The tapered body 2046 extends a sufficient distance from the head so that it passes completely through the opening 2042 in the annulus 2043. The tapered body is larger or wider adjacent the head and narrows as it extends from the head.

A central cylindrical shaft 2047 extends completely through the head 2041 and the tapered body 2046. A push rod 2048 having a disc-shaped end 2050 and a rod portion 2049 attached to and extending from the end 2050 is disposed in the cylindrical shaft 2047. The head portion 2041 includes a pocket 2052 sized and shaped to accommodate the disc-shaped end 2050 of the push rod 2048. Initially, the rod portion 2049 is only partially inserted through the cylindrical shaft 2047 starting from the head portion 2041 of the plug 2040 (FIG. 77). In one embodiment, the length of the cylindrical shaft 2047 into which the rot portion 2049 does not extend if filled with a flowable plug material 2051.

In use, the tapered body 2046 is inserted into the opening 2042 in the annulus 2043 and the barbs 2053 extend into the annulus 2043 until the head portion 2041 contacts the exterior surface 2044 of the annulus 2043. The push rod 2048 is advanced in the direction of arrow K until the end 2050 is located within the pocket 2053 of the head portion 2041 (FIG. 78). The rod portion 2049 pushes the flowable plug material 2051 from the cylindrical shaft 2047. The flowable plug material plugs the interior of the opening 2042 and anchors the plug 2040 from being expelled out from the opening.

Figure 79:
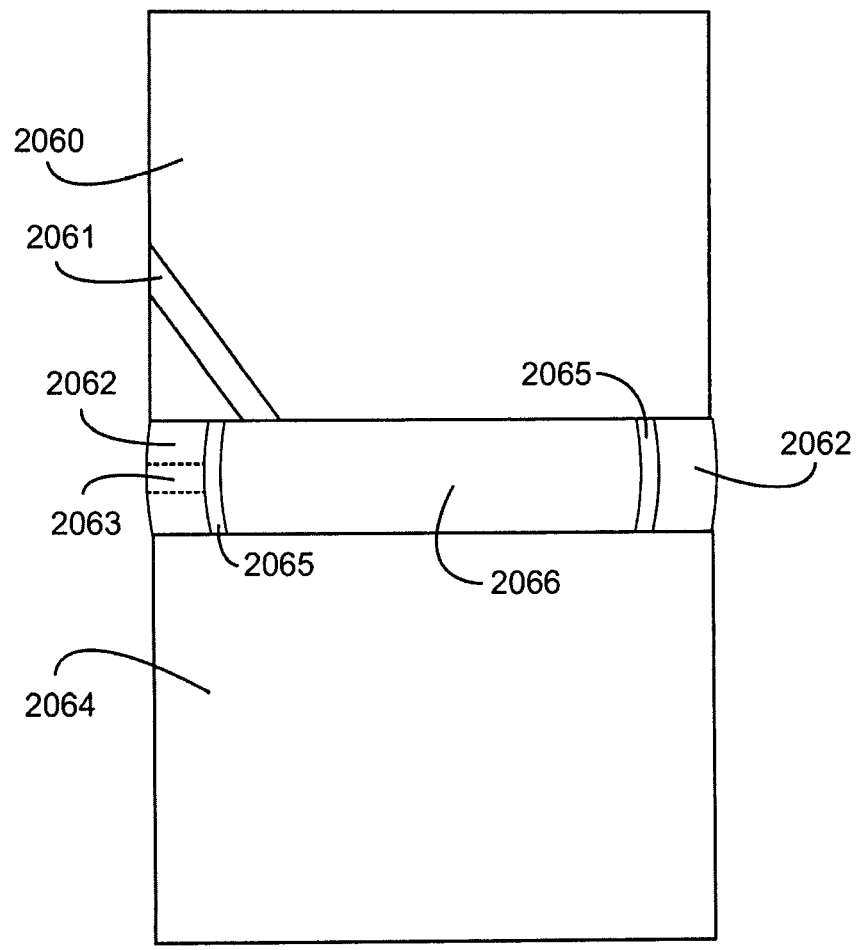
FIG. 79 is a schematic representation illustrating insertion of a cover-type plug into the interior of a disc.
Figure 80:
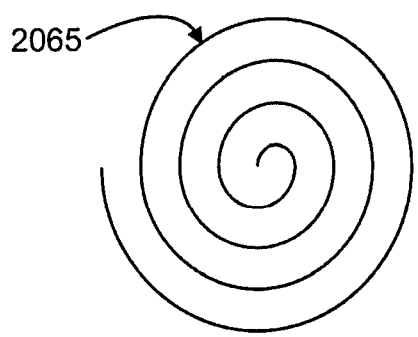
FIG. 80 is a representation of another embodiment of a cover-type plug in a coiled position for insertion into an annulus.

Referring to FIGS. 79-80, another embodiment of the soft tissue repair system of the present invention using a plug is illustrated. In this embodiment, a cover-type plug 2065 is used to cover the opening 2063 in the annulus 2062 at the interior surface of the annulus. In one embodiment, the plug 2065 is a deployable sheath that can be constructed from metal such as titanium, a polymer or combinations thereof. In one embodiment, the plug is a polymer covered metal. The plug 2065 has a natural or resting shape that is generally circular and is sufficiently flexible and resilient that it can be folded or wound into a smaller spiral shape.

In order to deploy the plug 2065, a hole 2061 is drilled through either the superior vertebral body 2060 or the inferior vertebral body 2064 into the interior of the disc 2066 without touching the annulus 2062. The plug 2065 is rolled or folded to a size small enough to pass through the hole 2061 and is introduced through the hole 2061 into the interior of the disc 2066. The plug 2065 is allowed to return to its resting position, where it unfolds or unrolls and contacts the interior surface of the annulus 2062. This covers the annulus opening 2063 and internal disc pressure holds the plug 2065 against the annulus 2062. In one embodiment, a flowable or formable plug material can also be used to fill the opening 2063 from the exterior of the opening. The hole 2061 is closed, for example, using a small screw made of a resorbable material.

Figure 81:
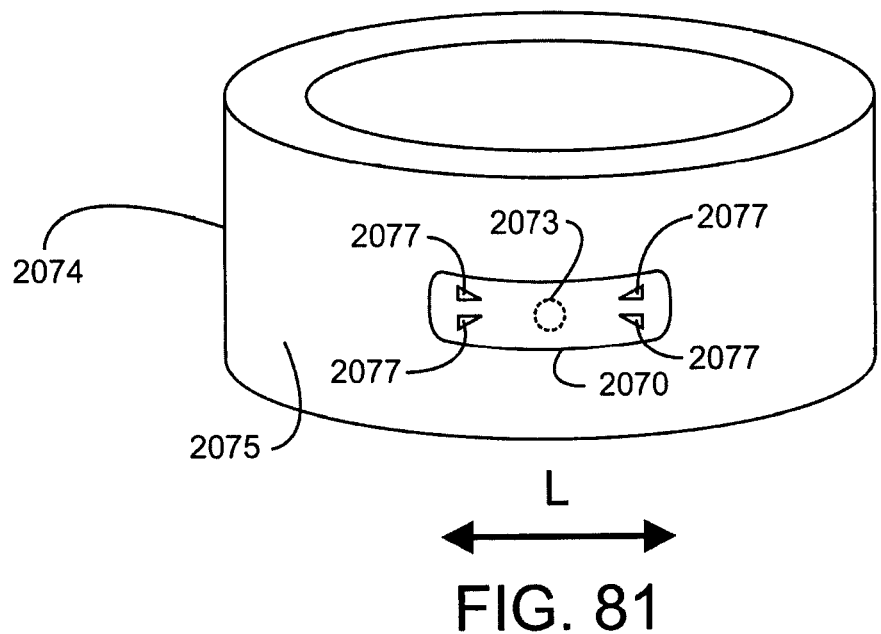
FIG. 81 is a representation of another embodiment of a cover-type plug applied over an annulus opening.
Figure 82:
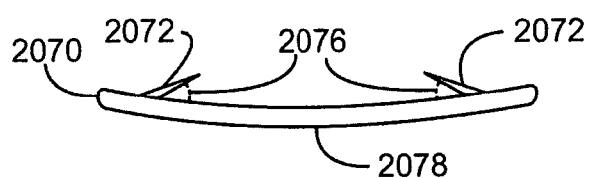
FIG. 82 is a representation of the side view of the cover-type plug shown in FIG. 81.

Referring to FIGS. 81-82, another embodiment of the soft tissue repair system of the present invention using a plug is illustrated. In this embodiment, a cover-type plug 2070 is used to cover and close the opening 2073 in the annulus 2074. The plug 2070 is attached to the exterior surface 2075 of the annulus 2074. Suitable materials include metals such as titanium and polymers such as PCU. The plug 2070 is provided with a curvature that accommodates the curvature of the exterior surface 2075 of the annulus 2074. The plug 2070 includes a plurality of barbs 2072. In one embodiment, the plug 2070 includes four barbs 2072 arranged as opposing pairs and formed from cut-outs 2077 in the body of the plug 2070. The plug 2070 is placed over the opening, and the barbs 2072 are pushed into the annulus 2074. In one embodiment, each barb 2072 extends from the plug 2070 at an angle 2076 that is less than about 90°. In addition, all of the barbs 2072 extend from the plug 2070 toward a central region 2078 of the plug. When the plug 2070 is attached to the annulus 2074 such that a resultant stretching force exists around the circumference of the annulus between the annulus and the plug as indicated by arrow L, this stretching force drives the barbs, which face in directions that oppose this force, into the annulus. This works to secure or hold the plug to the annulus.

Figure 83:
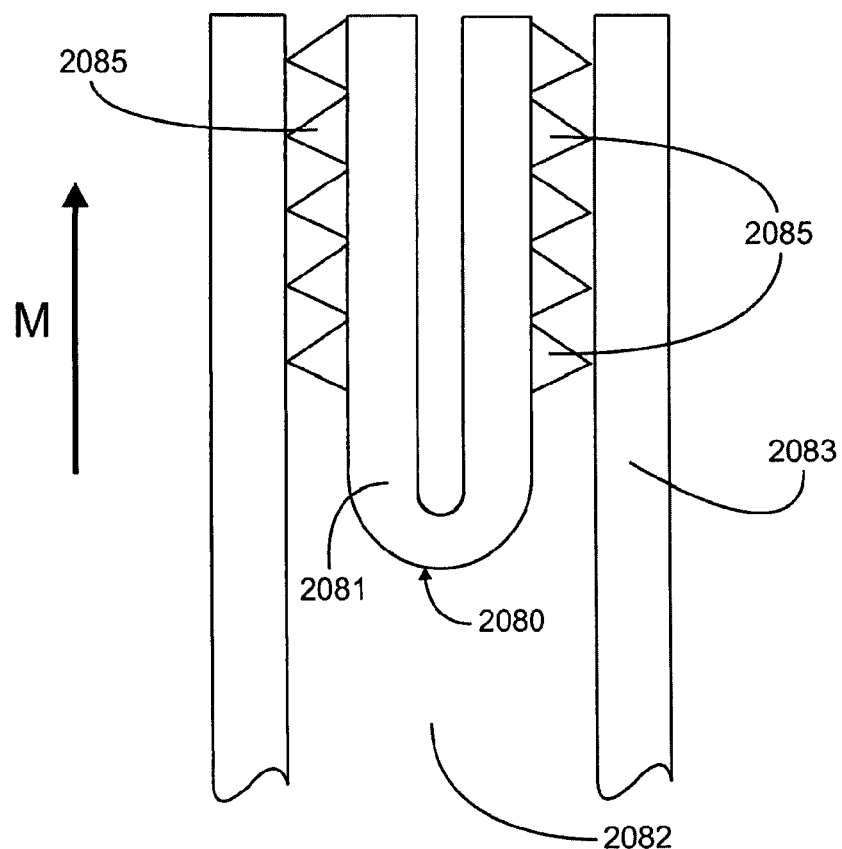
FIG. 83 is a representation of another embodiment of a plug disposed in a cannula.
Figure 84:
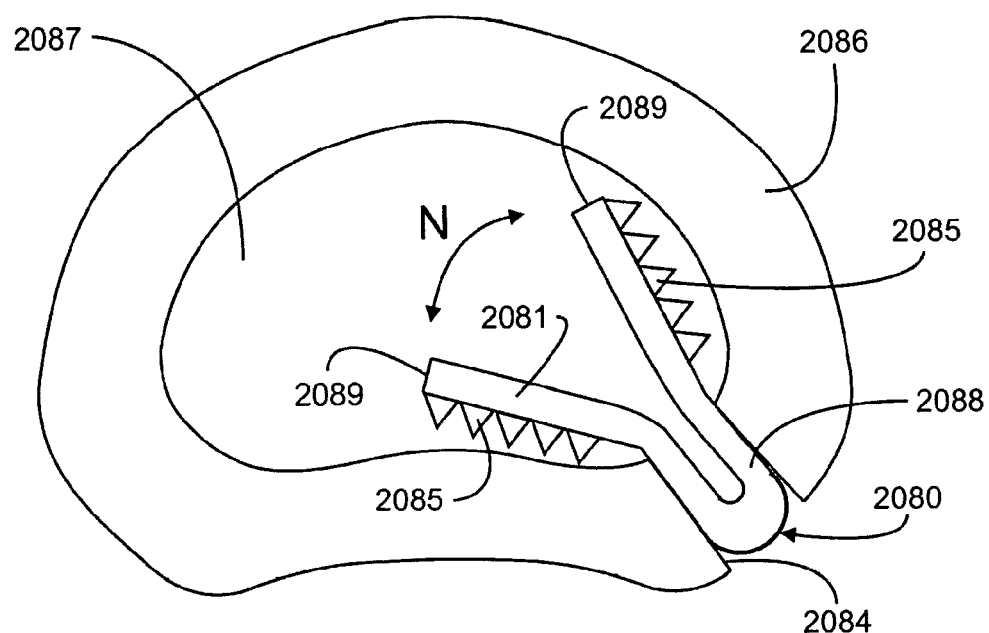
FIG. 84 is a representation of the plug of FIG. 83 disposed in an annulus opening.

Referring to FIGS. 83-84, another embodiment of the soft tissue repair system of the present invention using a plug is illustrated. In this embodiment, the plug 2080 is formed as either a living hinge or a mechanical hinge. As illustrated, the plug 2080 is formed of a bar or block of material 2081 that has a resting or natural position that is flat. Suitable materials for the block of material include, but are not limited to, metals such as titanium and polymers, for example PCU. The block of material is bent into a "U" shape and placed in the interior 2082 of a cannula 2083. The interior is sized to be smaller than the opening 2084 of the annulus 2086 that is to be repaired. The cannula holds the block of material in the "U" shape. A plurality of pointed teeth 2085 extends from the block of material.

The plug 2080 is advanced from the cannula 2083 in the direction of arrow M until the plug exits the cannula and passes through the opening 2084 in the annulus 2086. The portion of the plug containing the teeth 2085 passes into the interior 2087 of the disc. A hinge portion 2088 of the plug 2080 remains in the opening 2084. The opposing legs 2089 of the plug 2080 are biased away from each other as indicated by arrow N. This biasing force drives the teeth 2085 into the interior surface of the annulus and forces the hinge portion 2088 into the walls of the opening 2084. This anchors the plug 2080 in the opening. A second flowable plug material can also be used in conjunction with the plug 2080 to fill in gaps between the plug 2080 and the annulus 2086. In another embodiment, the hinge portion contains a mechanical hinge, for example a spring loaded hinge, that biases the opposing legs 2089 of the plug 2080 away from each other. Suitable mechanical hinges are known and available in the art.

Referring to FIGS. 85-88, another embodiment of the soft tissue repair system of the present invention using a plug is illustrated. In this embodiment, the plug 2090 includes an integrated anchoring mechanism that is activated after the plug is inserted into the opening 2091 in the annulus 2092 that is being repaired. The plug 2090 includes a plurality of independent and separate segmented arms 2093. Each segmented arm 2093 includes a plurality of segments. In one embodiment, this plurality of segments includes a primary segment 2094, a first intermediate segment 2095 attached to one end of the primary segment, a second intermediate segment 2096 attached to the first intermediate segment and an end segment 2097 attached to the second intermediate segment. The first intermediate segment 2095 is disposed between the primary segment and the second intermediate segment, and the second intermediate segment 2096 is disposed between the first intermediate segment and the end segment. In one embodiment, the adjacent segments overlap, and a pivot pin 2099 passes through this overlapped section so that the adjacent segments are attached at a pivot point or joint. Alternatively, all of the segments are formed as a single piece of material with a notch or bend formed in the material at the transition between each segment. Therefore, the single piece of material will bend at these points to define the various segments. Suitable materials for the segments and pivot pins include, but are not limited to, metals such as titanium and plastics or polymers such as PCU.

Initially, the primary segment 2094 and first and second intermediate segments are arranged in a first straight line. The end segment 2097 is located along a second line that is separate from and parallel to the first line. In one embodiment, the end segment touches at least one of the first and second intermediate segments along their length. In order to provide for this initial offset alignment between the first and segment intermediate segments and the end segment, the end segment 2097 has an "L" shape. The second intermediate segment, on the end that is pivotally attached to the end segment, has a rounded edge 2098. This facilitates passage of the plug 2090 through the opening 2091 in the annulus 2092.

Each primary segment 2094 includes a distal end that is pivotally attached to the first intermediate segment 2095. The proximal end 3000 of the primary segment 2094 opposite the distal end is enlarged and includes a hook portion 3002. The hook portion 3002 engages the exterior surface of the annulus adjacent the opening. The length 3004 of the primary segment from approximately the hook portion 3002 to the pivot pin 2099 between the primary segment and the first intermediate segment 2095 is varied depending on the thickness of the annulus and is selected such that the primary segment will pass completely through the opening until the pivot pin 2099 emerges in the interior of the disc.

In one embodiment, the plurality of segmented arms is arranged around a common axis to form the general shape of a cylindrical plug with an enlarged head. Cross members (not shown) can be provided between the primary segments of each segmented arm to hold the plurality of segmented arms together. All of the proximal ends 3000 of the segmented arms 2093 yield an enlarged head having an overall diameter 3006 that is larger than the opening 2091 in the annulus 2092. In one embodiment, the plug 2090 includes an even number of segmented arms arranged as opposing pairs. Preferably, this even number of segmented arms is four arms.

The plug 2090 also includes a threaded set screw 3008 that runs through the center of the cylindrical shape created by the plurality of segmented arms along and concentric with the common axis of the segmented arms. Suitable materials for the set screw include, but are not limited to, metals such as titanium. The set screw has an enlarged head 3010 at its proximal end and is threaded 3014 on its distal end. The enlarged head 3010 includes a slot 3012 for accepting a tool such as a flathead screwdriver for turning the set screw 3008. The enlarged end 3000 of each segmented arm includes a curved pocket 3016 to accept the enlarged head 3010 of the set screw. The curved pocket allows the set screw to turn while holding the set screw within the plug 2090. The threaded distal end 3014 of the set screw is in contact with each end segment 2097 of the segmented arms. Each end segment includes a notch 3018 to accommodate the threaded distal end 3014. The notch can have complementary threads or the end segment can be formed of a material that is sufficiently soft to be gripped by the threads.

Figure 85:
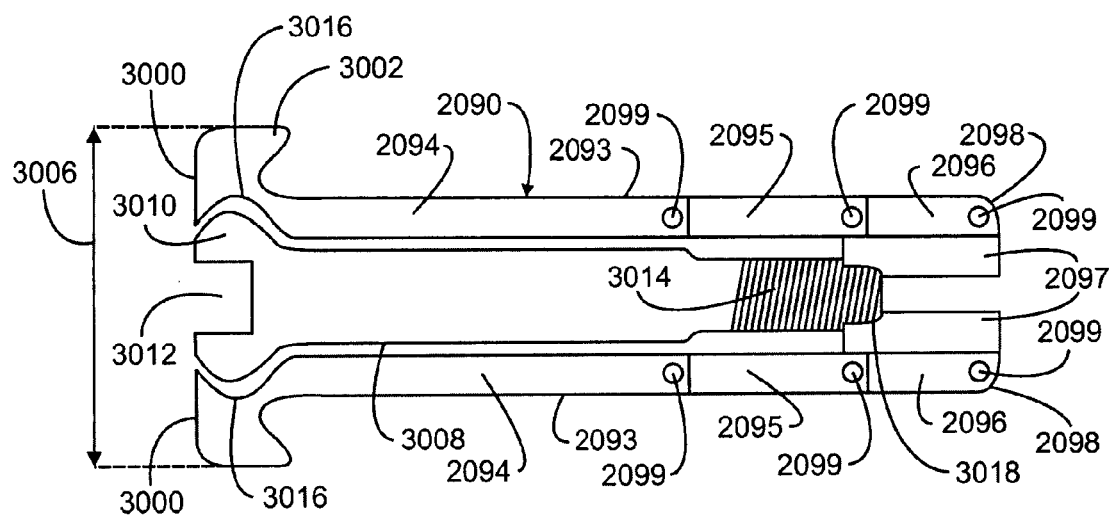
FIG. 85 is a representation of another embodiment of a plug in combination with a clamping mechanism in accordance with the present invention.
Figure 86:
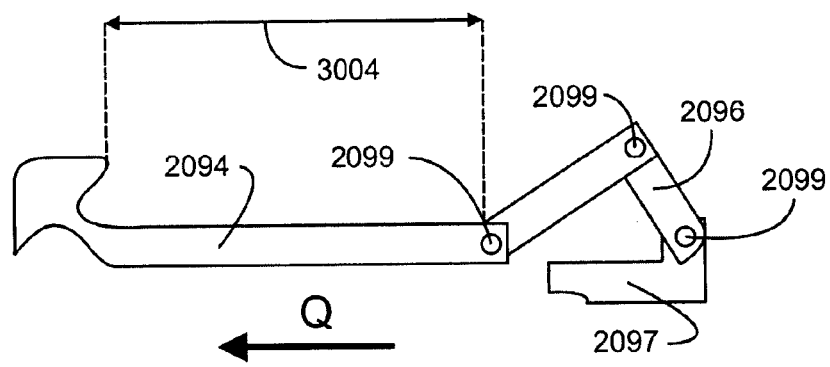
FIG. 86 is a representation of one of the segmented arms of the plug of FIG. 85.
Figure 87:
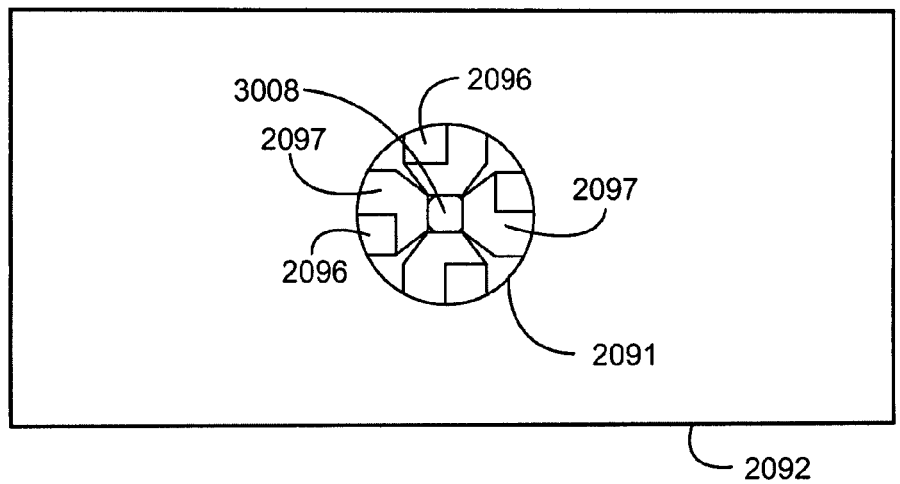
FIG. 87 is a representation of the plug of FIG. 85 inserted into an annulus opening as viewed from the interior of the annulus.
Figure 88:
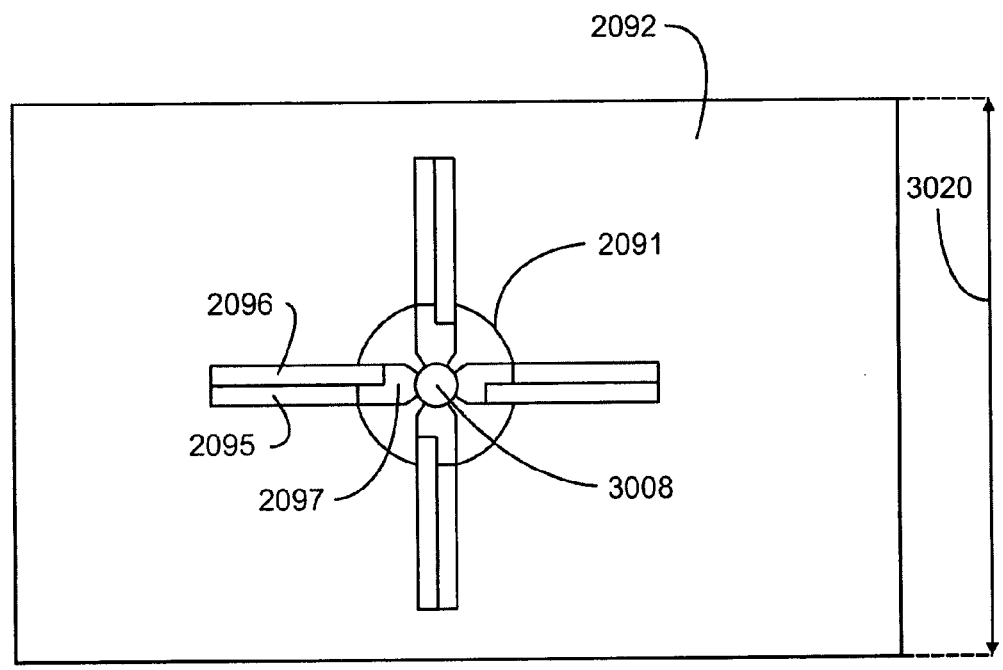
FIG. 88 is a representation of the plug of FIG. 85 inserted into an annulus and moved to an expanded position as viewed from the interior of the annulus.

In the initial state as illustrated in FIG. 85, the plug is inserted through the opening 2091 in the annulus 2092 (FIG. 87). As the set screw is turned in accordance with either a left-hand or right-hand thread, the relative rotational motion between the threaded distal end 3014 and the notch 3018 draws the end segment 2097 in the direction of arrow N parallel to the primary segment toward the distal end of the set screw (FIG. 86). All of the segments begin to rotate relative to each other about the pivot pins 2099. This forces the first and second intermediate segments out of alignment with the primary segment and toward a position that is perpendicular to the primary segment. The first and second intermediate segments contact the interior surface of the annulus, pulling the enlarged ends 3000 toward the exterior surface of the annulus and forcing the hook portions 3002 into the annulus. This anchors and holds the plug 2090 in the opening 2091. As viewed from the inside of the disc in FIG. 88, the segmented arm 2093 expands but does not exceed the thickness 3020 of the annulus.

Referring to FIGS. 89-90, another embodiment of the soft tissue repair system of the present invention using a plug is illustrated. In this embodiment, a cover-type plug 3050 is used that is provided in the form of a ribbon of material that is wrapped around the exterior surface of the annulus 3052. Suitable materials for the plug include, but are not limited to, polymers including polytetrafluoroethylene (PTFE), which is commercially available under the tradename Teflon from E.I. du Pont de Nemours and Company of Wilmington, Del. The plug 3050 is provided in the length that is at least as long as the outer circumference of the annulus 3052 and a width that is sufficient to cover the opening 3054 in the annulus.

In order to install the plug 3050, the plug 3050 is attached to the end of a flexible hook 3056 that has a natural position that is curved. In one embodiment, the flexible hook is a nitinol (nickel titanium) hook. The flexible hook and attached plug are placed in a cannula 3058 or other suitable insertion tube (FIG. 90). In this retracted state, the cannula is placed adjacent the annulus, and the flexible hook and plug are extended from the cannula. Given the natural curved position of the flexible hook, the flexible hook and plug extend around the exterior surface of the annulus. The flexible plug is then attached to the exterior surface of the annulus at a given point 3060 using any suitable attachment mechanism, for example sutures. The flexible hook is then retracted into the cannula, leaving the plug 3050 extending around the annulus. The plug extends sufficiently around the annulus to completely cover the opening 3054 and in one embodiment extends completely around the annulus. The plug is cut or trimmed after it has been extended a sufficient distance around the annulus, and the plug is attached to the annulus at this second position after it is extended around the exterior of the annulus. The flexible hook is then retracted inside the annulus. In one embodiment, the opening is also filled with a flowable plug material that is placed in the opening before the plug 3050 is extended around the annulus.

Figure 91:
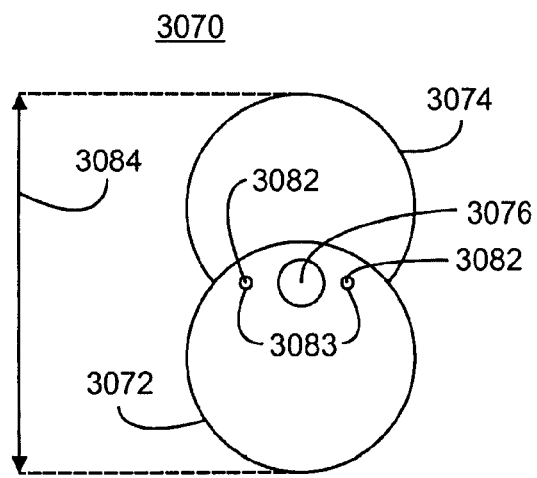
FIG. 91 is a representation of another embodiment of a plug in an expanded state.
Figure 92:
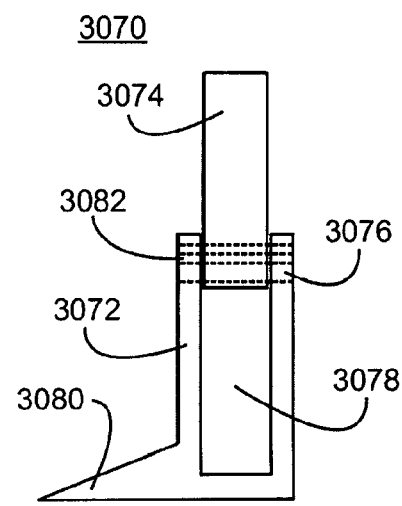
FIG. 92 is a representation from the side of the plug of FIG. 91.

Referring to FIGS. 91-92, another embodiment of the soft tissue repair system of the present invention using a plug is illustrated. In this embodiment, a cover-type plug 3070 is provided. Suitable materials for the plug 3070 include, but are not limited to, metals such as titanium and polymers such as PCU. The plug 3070 includes a first outer component 3072 and a second inner component 3074. In one embodiment, the first and second components are generally circular, although the components can be provided in any desired geometric shape. The first component 3072 includes a slot 3078 sized to hold the second component 3074. The second component 3074 can be completely stored within the slot 3078.

The first and second components are both rotatable about a common eccentric shaft 3076 that passes completely through the first and second components. Therefore, the second component 3074 rotates around the shaft 3076 into and out of the slot 3078. The second component 3074 is moved from a position where it is completely contained within the slot 3078 and the plug 3070 has its minimum size to a position where it is outside (as illustrated) the slot 3078 opposite its position within the slot and the plug 3070 achieves is maximum size 3084 or height. A plurality of pins 3082 are inserted through holes 3083 in both the first and second components that align when the second component 3074 is rotated to the position yielding the maximum plug size. This locks that plug in this position.

The plug 3070 is used to cover openings in the annulus from either the interior or exterior of the annulus. In one embodiment, the plug is passed through the annulus opening with the second component located within the slot 3078. The second component is then rotated to the maximum plug size position and locked in that position. Therefore, the plug 3070 covers the entire annulus opening. The plug 3070 also includes at least one barb 3080 that is attached to or formed integral with the first component. The barb 3080 anchors the plug 3070 to the annulus adjacent the opening. In one embodiment, the plug 3070 is used in combination with a flexible or flowable plug material that is used to fill the annulus opening.

Figure 93:
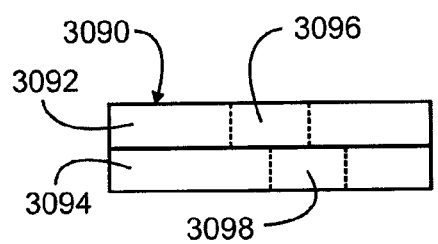
FIG. 93 is a representation of an embodiment of an anchor plate for use in an embodiment of a plug.
Figure 94:
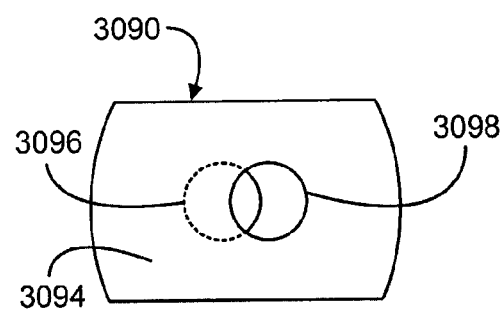
FIG. 94 is another representation of the anchor plate of FIG. 93.
Figure 95:
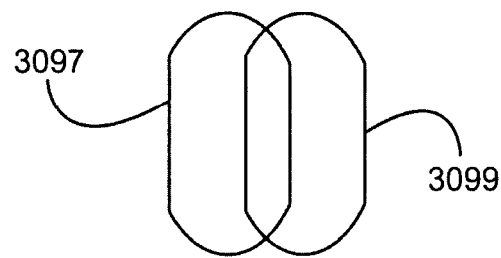
FIG. 95 is a representation of another embodiment for the shape of the holes in the anchor plate of FIG. 93.

Referring to FIGS. 93-99, another embodiment of the soft tissue repair system of the present invention using a plug is illustrated. Referring to FIGS. 93-94, the plug in this embodiment utilizes an anchor plate 3090. The anchor plate 3090 is part of a plug assembly and is passed through the annulus opening to the interior of the disc and makes contact with the interior surface of the annulus to anchor the plug assembly to the annulus. The anchor plate 3090 is constructed from a front plate 3094 having a front plate opening 3098 and a back plate 3092 having a back plate opening 3096. In an initial or rest position as illustrated, the front plate 3094 is aligned with the back plate 3092, while the front plate opening 3098 is not aligned with the back plate opening 3096. The two openings are offset, and there is a biasing member (not shown) disposed between the two plates that biases the plates toward the rest position. In one embodiment, the two openings are circular. Alternatively as illustrated in FIG. 95, the front plate opening 3099 and the back plate opening 3097 have an elongated shape. The shape of the openings is selected based upon the shape of the plug insert that is being used in conjunction with the anchor plate.

Figure 96:
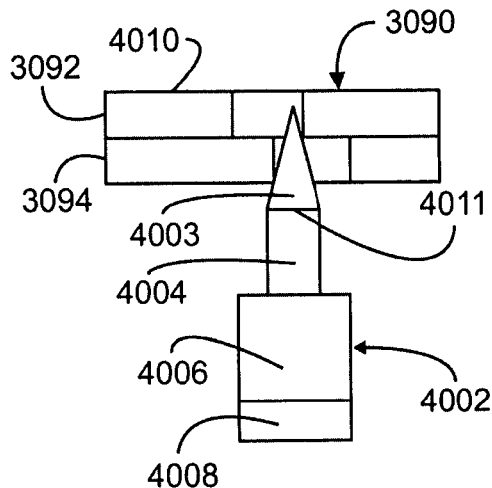
FIG. 96 is a representation of the plug and anchor plate embodiment of FIG. 93 with the plug partially inserted into the anchor plate.
Figure 97:
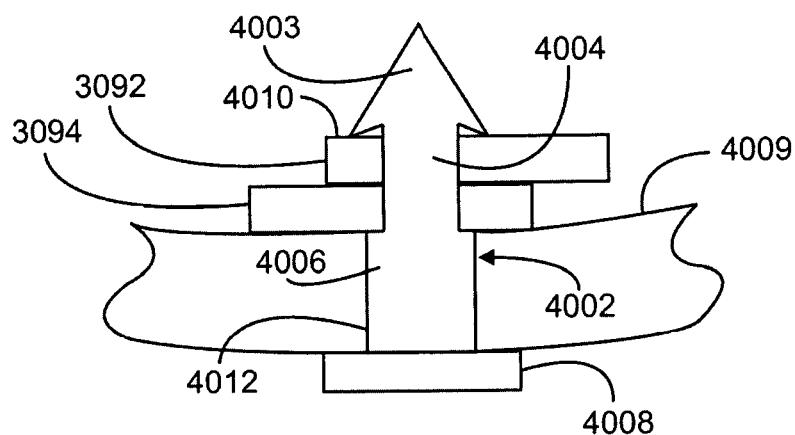
FIG. 97 is a representation of the plug and anchor plate embodiment of FIG. 93 disposed in an annulus opening with the plug partially fully into the anchor plate.

Referring to FIGS. 96 and 97, the plug insert portion 4002 of the plug includes a tapered portion 4003, an anchor plate portion 4004 extending back from the tapered portion, a plug portion 4006 extending from the anchor plate portion and an enlarged head portion 4008 extending from the plug portion. The tapered portion 4003 is shaped to pass through the openings in the anchor plate 3090 and to move the first and second plates from their rest position toward a position where the openings are aligned. A ridge or edge 2011 between the tapered portion and the anchor plate portion 4004 contacts with a side 4010 of the back plate 3092 after the tapered portion passes completely through the anchor plate 3090. When this ridge 2011 is circular and extends completely around the plug insert portion, circular openings are used. When the ridge extends out from the plug insert portion in two opposite directions (FIG. 97), elongated openings are used. The anchor plate portion is preferably cylindrical and has a diameter equal to the diameter or width of the openings. Therefore, as the tapered portion passes through the openings, the anchor plate portion engages the openings.

The plug portion is sized to substantially fill the opening 4012 in the annulus 4009. The enlarged head portion 4008 is larger than that opening 4012 and engages the exterior surface of the annulus 4009. Initially, the anchor plate 3090 is passed through the opening, and the openings in the anchor plate are aligned with the opening in the annulus. The plug insert portion is passed through the opening in the annulus and the openings in the anchor plate until the tapered portion is passed completely through the anchor plate openings. For elongated anchor plate openings, the plug insert portion is then rotated 90° so that the tapered portion engages the side of the back plate. The anchor plate is in contact with the interior surface of the annulus, and the enlarged head portion is in contact with the exterior surface of the annulus, anchoring the plug in the opening.

Figure 98:
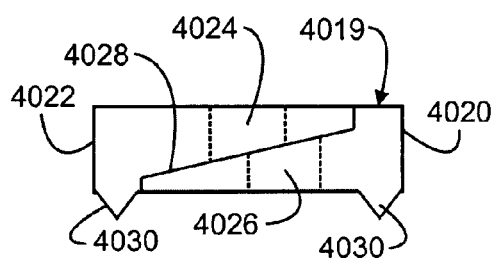
FIG. 98 is a representation of another embodiment of an anchor plate for use in an embodiment of a plug.
Figure 99:
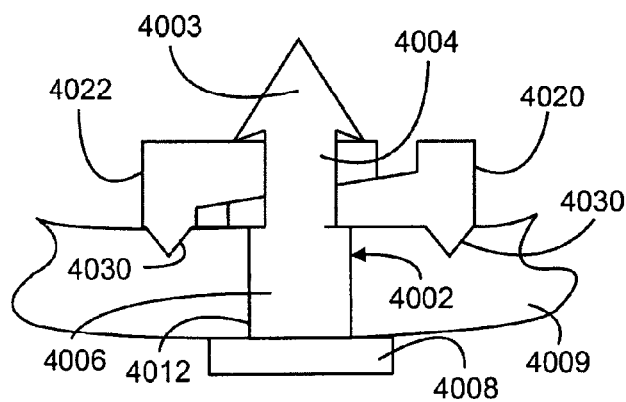
FIG. 99 is a representation of the plug and anchor plate embodiment of FIG. 98 disposed in an annulus opening with the plug partially fully into the anchor plate.

In an alternative embodiment as illustrated in FIG. 98-99, an alternate anchor plate 4019 is used in which the back plate 4022 having a back plate opening 4024 and the front plate 4020 having a front plate opening meet along a sloped face 4028. Each plate does not extend across the entire width of the anchor plate 4019. In addition, each plate includes a barb 4030 on one end, and this barb engages the annulus 4009 when the plug assembly is inserted into the opening 4012 (FIG. 99).

Figure 100:
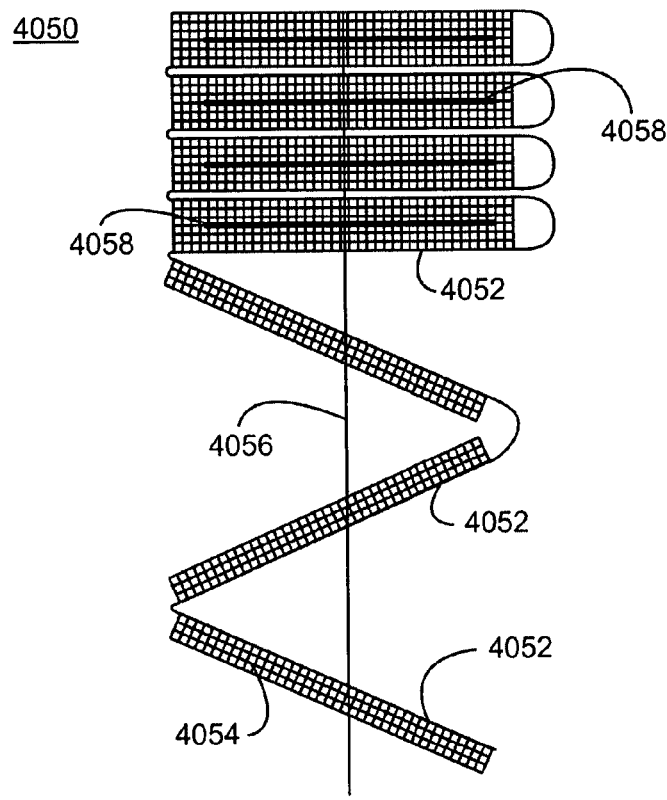
FIG. 100 is a representation of another embodiment of a plug in a partially folded position in accordance with the present invention.
Figure 101:
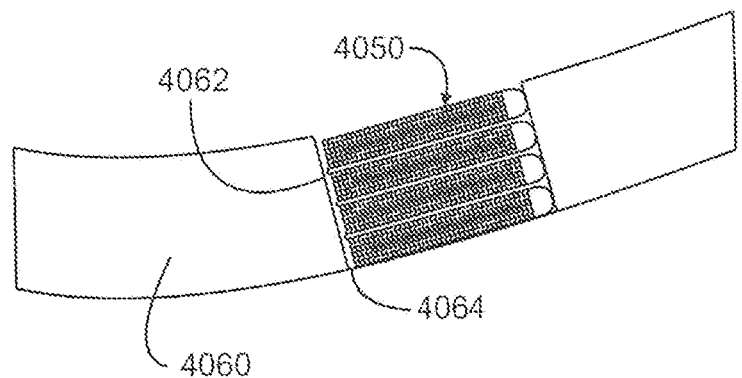
FIG. 101 is a representation of the plug of FIG. 100 in a fully folded position disposed in an annulus opening.

Referring to FIGS. 100-101, another embodiment of the soft tissue repair system of the present invention using a plug is illustrated. In this embodiment, the plug 4050 is formed from a layer of collagen 4052 attached to a mesh 4054. Suitable materials for the mesh include, but are not limited to, decellularised extracelluar matrices (ECM) and small intestine submucosa (SIS) mesh, which is commercially available from Cook Medical of Bloomington, Ind. Alternatively, the plug can be formed of a synthetic polymer. The mesh and collagen material is folded and stack accordion style into a plurality of layers. The number of layers and the size of each fold is selected based upon the size of the opening 4062 in the annulus that is to be repaired.

Cells 4058 are injected between each layer. In one embodiment, a mixture of cells and growth factors (GFs) is injected between each layer. As illustrated, the cells 4058 are injected between opposing mesh 4056 layers. Alternatively, the cells can be provided between opposing collagen 4052 layers or between both opposing mesh and opposing collagen layers. In order to facilitate the folding of the layers and to hold the folded plug in the folded position, a guide fiber 4056 is anchored to the first folded layer, passed through each of the folded layers and secured or tied to the final folded layer. The plug 4050 is then inserted into the annulus opening 4062 such that the folds run from the interior of the opening to the exterior of the opening. In order to secure the plug in the opening, a glue or adhesive 4064 is applied over the opening and the plug on the exterior surface of the annulus 4060.

Figure 102:
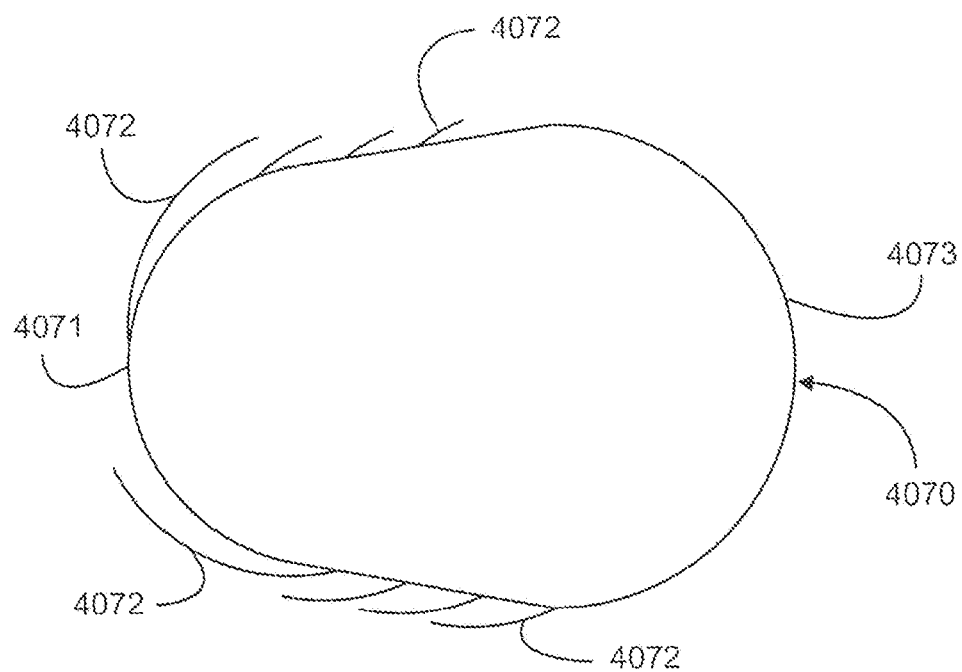
FIG. 102 is a representation of another embodiment of a plug in accordance with the present invention.

Referring to FIG. 102, another embodiment of the soft tissue repair system of the present invention using a plug is illustrated. In this embodiment, a plug 4070 is provided having a narrow end 4071 and a wide end 4073. In three dimensions, the plug is substantially egg-shaped. Suitable materials for the plug include, but are not limited to, polymers and plastics such as PCU. The plug also includes a plurality of curved spines that extend from the sides and narrow end 4071 of the plug. Suitable materials for the spines include, but are not limited to, polymers, plastics and metals, for example titanium.

In one embodiment, all of the spines curve around the plug in the same direction. Alternatively, the spines curve around the plug in two different directions. The plug is inserted through an annulus opening narrow end first until the wide end is located substantially even with the exterior surface of the annulus. The spines extend into the interior walls of the opening, preventing the plug from being drawn farther into or being expelled from the opening. In one embodiment, the spines are retractable or spring loaded and extend into the sides of the opening after the plug has been inserted into the opening. In one embodiment, the plug is used in combination with a flowable plug material to fill the gaps between the plug and the opening in the annulus.

Referring to FIGS. 103-104, another embodiment of the soft tissue repair system of the present invention using a plug is illustrated. In this embodiment, the plug 4080 is arranged as a "pop-rivet" type plug. Suitable materials for this plug 4080 include, but are not limited to, metals such as titanium. The plug 4080 includes a rivet portion 4083 sized to pass through an opening 4087 in an annulus 4088. One end of the rivet portion 4083 is formed as an enlarged head 4084 that is size large enough to not pass through the annulus opening 4087 but to engage the exterior surface of the annulus 4088. The opposite end of the rivet portion 4083 has an opening that passes completely through the rivet portion. Extending through this opening is a shaft 4085 that extends sufficiently through the enlarged head to provide sufficient gripping surface for a tool that will compress the plug 4080. One end of the shaft 4085 includes a ball that is sized larger than the opening in the rivet portion. The ball is still small enough to pass through the annulus opening.

The ball and rivet portion is passed completely through the opening until the enlarged head touches the annulus. A tool is used to grip the shaft. The tool also engages the enlarged head. The tool pushed on the enlarged head and draws the shaft through the rivet portion. This moves the ball toward the enlarged head, compressing the rivet portion. The rivet portion is deformed into a compressed portion 4086 on the interior of the disc that is larger than the annulus opening. This compressed portion is in contact with the interior surface of the annulus. Having achieved the desired compression, the tool clips that shaft at a point that is substantially even with the enlarged head. The opening is thus sealed and the plug is secured in the annulus opening. In one embodiment, this plug is used in combination with a flowable plug material that fills gaps and voids between the plug and the annulus opening.

Figure 106:
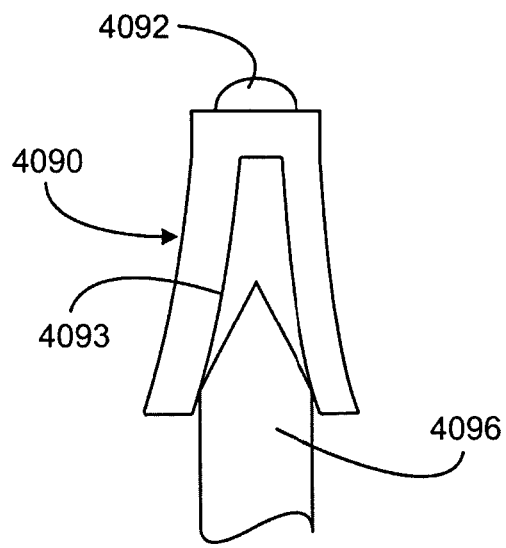
FIG. 106 is a representation of the plug and clamping mechanism of FIG. 105 with the clamping mechanism partially expanded.
Figure 107:
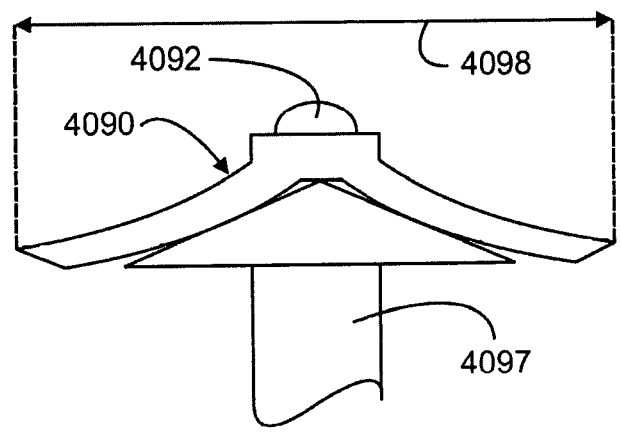
FIG. 107 is a representation of the plug and clamping mechanism of FIG. 105 with the clamping mechanism fully expanded.
Figure 109:
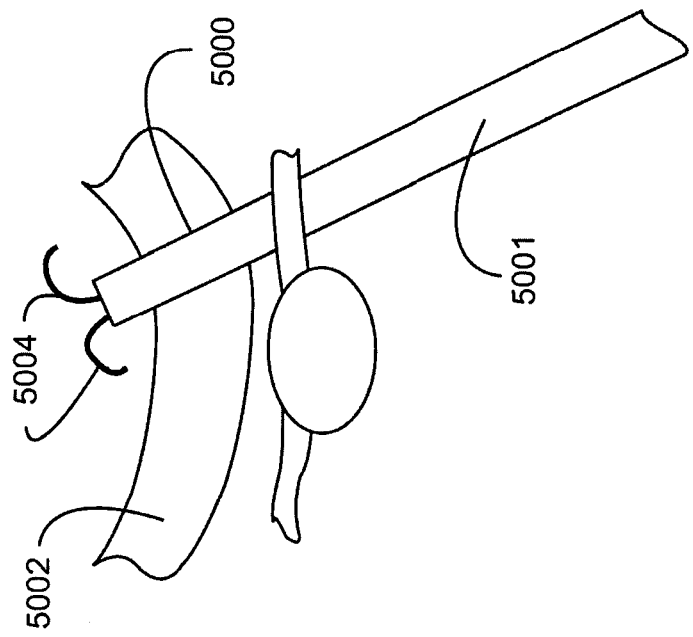
FIG. 109 is a representation of the plug of FIG. 108 with curved needles partially extended from the inserter tool.
Figure 108:
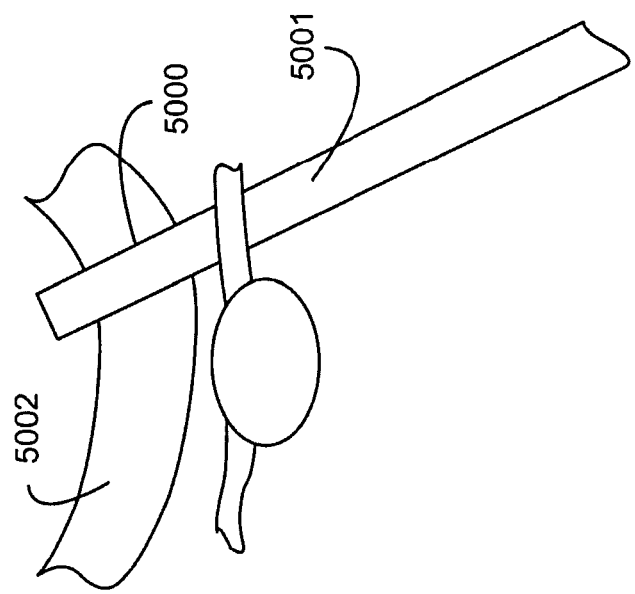
FIG. 108 is a representation of another embodiment of a plug with an inserter tool inserted through an annulus opening.
Figure 111:
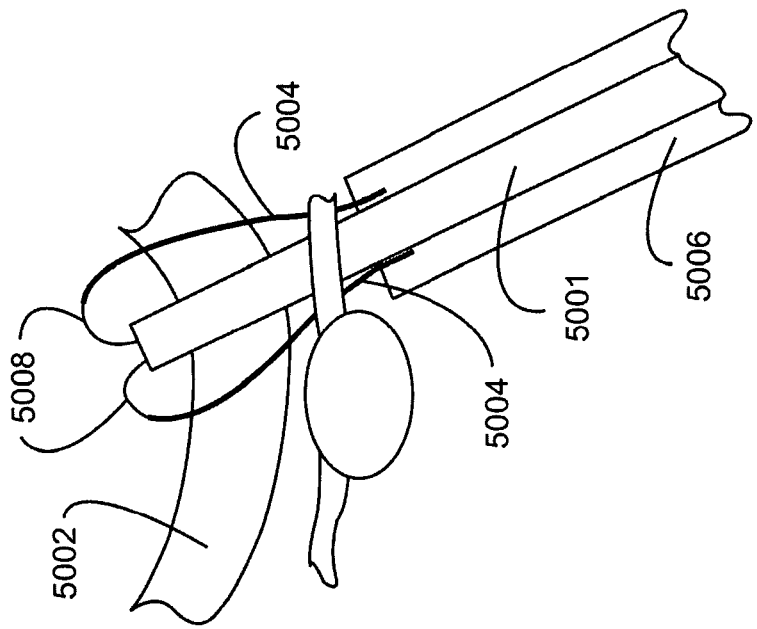
FIG. 111 is a representation of the plug of FIG. 108 with curved needles further partially extended from the inserter tool through the annulus and into a grip tool exposing sutures.
Figure 110:
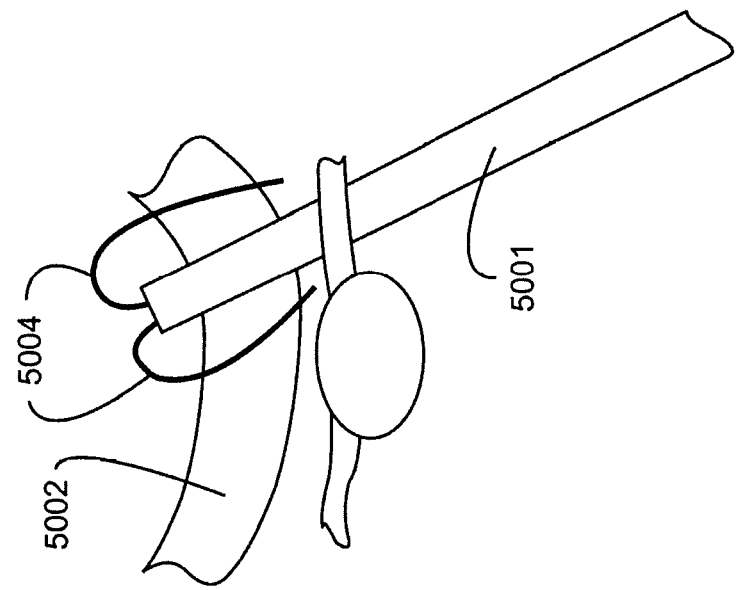
FIG. 110 is a representation of the plug of FIG. 108 with curved needles further partially extended from the inserter tool through the annulus.
Figure 113:
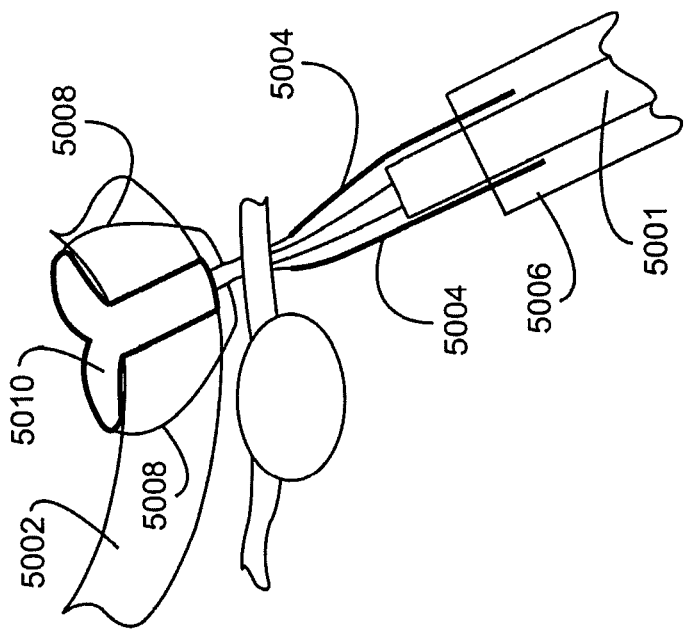
FIG. 113 is a representation of the plug of FIG. 108 with the inserter tool and grip tool withdrawn leaving the plug in the annulus opening and the sutures secured at the exterior of the annulus.
Figure 112:
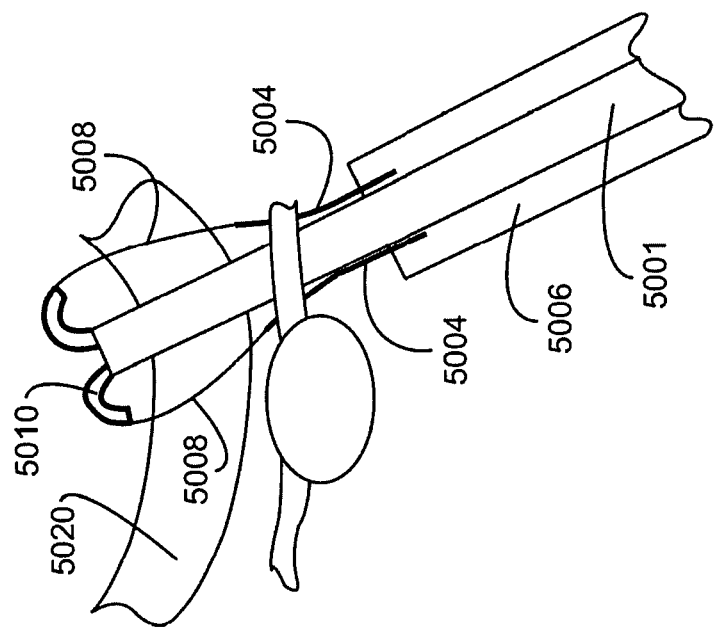
FIG. 112 is a representation of the plug of FIG. 108 with curved needles in a grip tool that is partially withdrawn drawing sutures through the annulus and exposing the plug.

Referring to FIGS. 105-107, another embodiment of the soft tissue repair system of the present invention using a plug is illustrated. In this embodiment, the plug 4090 is formed as an elongated box or cylinder having an initial width 4095 that is less than the size of the annulus opening. The leading end of the plug includes a ball or portion of a ball to aid in inserting the plug into the opening. The plug 4090 also includes a central cavity 4093, and an inserting pusher 4094 is inserted into the cavity. The pusher 4094 is used to insert the plug into the annulus opening. Having inserted the plug into the annulus opening, the pusher is removed from the cavity 4093. A first spreader 4096 that is sized larger than the cavity is passed through the cavity to expand the plug. The first spreader is removed, and a second, larger spreader 4097 is passed through the cavity. This expands the plug 4090 to a final size 4098 that is larger than the annulus opening. This plug can also be used in combination with a flowable plug material.

Referring to FIGS. 108-113, another embodiment of the soft tissue repair system of the present invention using a plug is illustrated. In this embodiment, a cannula or insertion tool 5001 is passed through the opening 5000 in the annulus 5002. A pair of bent wires or needles 5004 having a hooked-shaped natural position is passed out the end of the cannula 5001 into the interior of the disc. The wires 5004 continue to extend out from the cannula 5001, through the annulus 5002 adjacent the opening to the exterior of the annulus. A suture clamp and grip tool 5006 is passed over the cannula 5001 (FIG. 111), and the wires 5004 are extended until they are anchored or embedded in the clamp and grip tool 5006. Thread or suture material 5008 attached to the wires emerges from the cannula on the interior of the disc.

The clamp and grip tool 5006 is then pulled back from the cannula 5001 (FIG. 112), drawing additional sutures 5008 and the plug 5010 from the cannula. The cannula 5001 is then pulled out from the opening (FIG. 113), leaving the plug 5010 in the opening and exposing additional sutures 5011 attached to the other end of the plug 5010 on the exterior of the annulus. The sutures are then tied together, and the excess is cut. Suitable materials for the plug 5010 include flexible plug materials including polymers or plastics such as PCU.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s) and steps or elements from methods in accordance with the present invention can be executed or performed in any suitable order. Therefore, it will be understood that the appended claims are intended to cover all such modifications and embodiments, which would come within the spirit and scope of the present invention.

What is claimed is:

1. A soft tissue repair system for an intervertebral disc having an annulus and a nucleus pulposus, the system comprising:
a first flexible plug configured to conform to contours of the annulus and an opening in the annulus and to close the opening that passes through the annulus from an exterior surface of the annulus to an interior surface of the annulus by being positioned in at least one of within the opening, over the opening at the exterior surface and over the opening at the interior surface; and
a second plug separate from the first plug and configured to close the opening by being positioned in at least one of within the opening, over the opening at the exterior surface and over the opening at the interior surface, the second plug comprising a flowable plug material,
wherein the first flexible plug comprises an extension that extends into the opening between the exterior surface of the annulus and the interior surface of the annulus and a single central through hole that extends through the extension, the single central through hole configured to allow passage of the flowable plug material from the exterior surface to the interior surface and configured to be sealed by the flowable plug material, and
wherein a portion of the flowable plug material seals the outside of the opening proximal the exterior surface of the annulus and seals the single central through hole, wherein the portion of the flowable plug material that seals the outside of the opening is external to the extension of the first flexible plug,
wherein a portion of the flowable plug material is disposed inside the annulus adjacent the flexible plug such that the flowable plug material only partially fills the nucleus pulposus,
wherein a hollow tube is positioned within the single central through hole such that the hollow tube extends from a first proximal end of the flexible plug past a second distal end of the flexible plug, and is configured to allow the flowable plug material to flow through the single central through hole.

2. The soft tissue repair system of claim 1, wherein the flowable plug material comprises an adhesive material.

3. The soft tissue repair system of claim 1, wherein the flowable plug material comprises a material that hardens to a flexible plug material.

4. The soft tissue repair system of claim 1, wherein the first plug is disposed within the opening and the second plug is disposed between portions of the first plug and walls within the opening.

5. The soft tissue repair system of claim 1, wherein the first plug is disposed within the opening and the second plug covers the opening at the interior surface or exterior surface of the annulus.

6. The soft tissue repair system of claim 1, wherein the first plug comprises a cover-type plug configured to cover the opening at the interior surface or exterior surface of the annulus.

7. The soft tissue repair system of claim 6, wherein the second plug is disposed within the opening.

8. The soft tissue repair system of claim 1, wherein: the first plug comprises: a head portion configured to be larger than the opening at the exterior surface of the annulus; a tapered body attached to and extending from the head, the tapered body narrowing as it extends from the head; and a central cylindrical shaft extending completely through the head and the tapered body; and the second plug is disposed in the central cylindrical shaft.

9. The soft tissue repair system of claim 1, wherein the extension of the first flexible plug terminates at a free distal end.

10. The soft tissue repair system of claim 9, wherein the extension has a diameter smaller than the opening in the annulus.

11. The soft tissue repair system of claim 10, wherein the flowable plug material of the second plug fills the space between an outer surface of the extension and the opening in the annulus.

12. The soft tissue repair system of claim 1, wherein the first flexible plug has a y-shaped configuration.

* * * * *